US011322688B2

(12) United States Patent
Shibuya et al.

(10) Patent No.: US 11,322,688 B2
(45) Date of Patent: May 3, 2022

(54) N-TYPE SEMICONDUCTOR COMPOSITION, AND THIN FILM, ORGANIC PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Hiromasa Shibuya, Suwon-si (KR); Chul Baik, Suwon-si (KR); Yutaka Matsuo, Tokyo (JP); Sung Young Yun, Suwon-si (KR); Seon-Jeong Lim, Yongin-si (KR); Ji Soo Shin, Suwon-si (KR); Gae Hwang Lee, Seongnam-si (KR); Yeong Suk Choi, Suwon-si (KR); Taejin Choi, Suwon-si (KR); Hye Rim Hong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 174 days.

(21) Appl. No.: 16/875,168

(22) Filed: May 15, 2020

(65) Prior Publication Data

US 2020/0365807 A1 Nov. 19, 2020

(30) Foreign Application Priority Data

May 15, 2019 (KR) ........................ 10-2019-0057222

(51) Int. Cl.
*H01L 51/00* (2006.01)
*C07D 209/56* (2006.01)
(Continued)

(52) U.S. Cl.
CPC ........ *H01L 51/0047* (2013.01); *C07D 209/56* (2013.01); *H01L 51/0046* (2013.01); *H01L 27/307* (2013.01); *H01L 51/4253* (2013.01)

(58) Field of Classification Search
CPC ............. H01L 51/0072; H01L 51/0056; H01L 51/0046; H01L 51/0053; H01L 51/0047;
(Continued)

(56) References Cited

U.S. PATENT DOCUMENTS 6,300,612 B1 10/2001 Yu
7,129,466 B2 10/2006 Iwasaki
(Continued)

FOREIGN PATENT DOCUMENTS

CN 107141243 A 9/2017
JP 2012089725 A 5/2012
(Continued)

OTHER PUBLICATIONS

Extended European Search Report dated Sep. 25, 2020, issued in corresponding European Patent Application No. 20174990.0.
(Continued)

*Primary Examiner* — Dung A. Le
(74) *Attorney, Agent, or Firm* — Harness, Dickey & Pierce, P.L.C.

(57) ABSTRACT

Disclosed are an N-type semiconductor composition including fullerene or a fullerene derivative; and fullerene subunit derivative represented by Chemical Formula 1, and a thin film, an organic photoelectric device, an image sensor and an electronic device including the same.
(Continued)

[Chemical Formula 1]

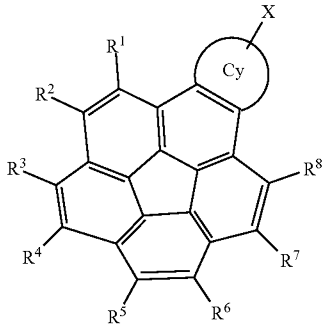

In Chemical Formula 1, X, Cy and $R^1$ to $R^8$ are the same as defined in the detailed description.

24 Claims, 9 Drawing Sheets

(51) Int. Cl.
*H01L 27/30* (2006.01)
*H01L 51/42* (2006.01)

(58) Field of Classification Search
CPC .. H01L 27/307; H01L 51/4253; Y02E 10/549
See application file for complete search history.

(56) References Cited

U.S. PATENT DOCUMENTS

| | | | |
|---|---|---|---|
| 7,566,943 | B2 | 7/2009 | Yokoyama |
| 7,794,854 | B2 | 9/2010 | Yamada et al. |
| 7,969,646 | B2 | 6/2011 | Miteva et al. |
| 7,973,307 | B2 | 7/2011 | Rand et al. |
| 8,035,708 | B2 | 10/2011 | Takizawa et al. |
| 8,426,727 | B2 | 4/2013 | Pfeiffer et al. |
| 8,592,931 | B2 | 11/2013 | Hayashi et al. |
| 8,625,016 | B2 | 1/2014 | Fossum et al. |
| 8,704,213 | B2 | 4/2014 | Suzuki |
| 8,907,352 | B2 | 12/2014 | Naito |
| 9,114,377 | B2 | 8/2015 | Swager et al. |
| 9,231,214 | B2 | 1/2016 | Tolbert et al. |
| 10,256,414 | B2 | 4/2019 | Lim et al. |
| 10,505,146 | B2 | 12/2019 | Heo et al. |
| 2007/0012955 | A1 | 1/2007 | Ihama |
| 2008/0142792 | A1 | 6/2008 | Park et al. |
| 2010/0297009 | A1 | 11/2010 | Olson et al. |
| 2012/0313088 | A1 | 12/2012 | Yofu et al. |
| 2013/0154040 | A1 | 6/2013 | Huh et al. |
| 2014/0209173 | A1 | 7/2014 | Momose |
| 2016/0013248 | A1 | 1/2016 | Sawaki |
| 2017/0069690 | A1 | 3/2017 | Sakurai et al. |
| 2017/0331050 | A1 | 11/2017 | Yagi et al. |
| 2018/0006090 | A1 | 1/2018 | Leem et al. |
| 2018/0062112 | A1 | 3/2018 | Heo et al. |
| 2018/0114935 | A1 | 4/2018 | Liang et al. |
| 2018/0123050 | A1 | 5/2018 | Rosselli et al. |
| 2019/0081251 | A1 | 3/2019 | Obana et al. |
| 2019/0363206 | A1* | 11/2019 | Fukuda ............... H01L 51/0097 |
| 2021/0043846 | A1* | 2/2021 | Arai .................... H01L 51/0046 |

FOREIGN PATENT DOCUMENTS

| | | | |
|---|---|---|---|
| JP | 2012248766 | A | 12/2012 |
| JP | 5227511 | B2 | 7/2013 |
| JP | 5323025 | B2 | 10/2013 |
| JP | 2017218381 | A | 12/2017 |
| JP | 2018513558 | A | 5/2018 |
| JP | 2018090684 | A | 6/2018 |
| KR | 20120131866 | A | 12/2012 |
| KR | 20130070892 | A | 6/2013 |
| KR | 20150066616 | A | 6/2015 |
| KR | 101709941 | B1 | 2/2017 |
| KR | 20180002272 | A | 1/2018 |
| KR | 20180024296 | A | 3/2018 |
| WO | WO-2017159025 | A1 | 9/2017 |

OTHER PUBLICATIONS

Extended European Search Report dated Sep. 25, 2020, issued in corresponding European Patent Application No. 20174222.8.

E.M. Cabaleiro-Lago et al., A theoretical study of complexes between fullerenes and concave receptors with interest in photovoltaics *Phys. Chem. Chem. Phys*, vol. 19, 2017, pp. 26787-26798.

Ru-Qiang Lu et al., 'Cocrystallization of Imide-Fused Corannulene Derivatives and $C_{60}$: Guest-Induced Conformational Switching and 1:1 Segregated Packing' *Chemistry: An Asian Journal*, vol. 13, 2018, pp. 2934-2938.

C. Mejuto et al., 'Self-Assembly of Di-N-Heterocyclic Carbene-Gold-Adorned Corannulenes on $C_{60}$' *Chemistry: A European Journal*, vol. 23, 2017, pp. 10644-10651.

R. Chen et al., 'Corannulene derivatives for organic electronic: From molecular engineering to applications' *Chinese Chemical Letters*, vol. 27, 2016, pp. 1175-1183.

Y. Kim et al., 'Benzocyclobutene-fullerene bisadducts as novel electron acceptors for enhancing open-circuit voltage in polymer solar cells' *Solar Energy Materials & Solar Cells*, vol. 141, May 2015, pp. 87-92.

M. J. Frisch, et al., Gaussian 09, Revision D.01; Gaussian, Inc.: Wallingford, CT 2009.

Juha Alakarhu, 'Image Sensors and Image Quality in Mobile Phones' *International Image Sensor Workshop*, Jun. 2007, pp. 1-4.

Y. Bando et al., 'Corannulene-Fused Anion-Responsive p-Conjugated Molecules that Form Self-Assemblies with Unique Electronic Properties' *Chemistry—An Asian Journal*, vol. 8, 2013, pp. 2088-2095.

K. G. Upul R. Kumarasinghe et al., 'Bis-corannulenoanthracene: An Angularly Fused Pentacene as a Precursor for Barrelene-Tethered Receptors for Fullerenes' *Organic Letters*, vol. 18, No. 3, 2016, pp. 3054-3057.

D. Josa et al., 'Ring-annelated corannulenes as fullerene receptors. A DFT-D study' *RSC Advances*, vol. 4, 2014, pp. 29826-29833.

R. Chen et al., 'Corannulene derivatives for organic electronics: From molecular engineering to applications' *Chinese Chemical Letters*, vol. 27, 2016, pp. 1175-1183.

B. M. Schmidt et al., 'Electron-poor N-substituted imide-fused corannulenes' *Chem. Communications*, vol. 48, 2012, pp. 6520-6522.

L. Meng et al., 'Thiophene-Fused π␣Systems from Diarylacetylenes and Elemental Sulfur' *Journal of the American Chemistry Society*, vol. 138, 2016, pp. 10351-10355.

C. Lin et al., 'High Photoelectric Conversion Efficiency of Metal Phthalocyanine/Fullerene Heterojunction Photovoltaic Device' *International Journal of Molecular Sciences*, vol. 12, 2011, pp. 476-505.

M.D. Iosip et al., 'New dithieno[3,2-b:2',3'-d]thiophene oligomers as promising materials for organic field-effect transistor applications' *Synthetic Metals*, vol. 146, 2004, pp. 251-257.

D.V. Konarev et al. "Donor-acceptor interaction of fullerence $C_{60}$ with triptycene in molecular complex TPC·$C_{60}$" J. Mol. Struct. vol. 526, 2000, pp. 25-29. dated Dec. 10, 1999.

Keita Sakakibara et al., "Chiroptical properties of an alternatingly functionalized cellotriose bearing two porphyrin groups" Chem. Commun., vol. 48, 2012, pp. 7672-7674. dated Mar. 21, 2012.

Tobias Hahn et al., "Role of Intrinsic Photogeneration in Single Layer and Bilayer Solar Cells with $C_{60}$ and PCBM" J. Phys. Chem. C, vol. 120, 2016, pp. 25083-25091. published Oct. 12, 2013.

S.J. Kim et al., 'Organic-on-silicon complementary metal-oxide-semiconductor colour image sensors' Scientific Reports 5:7708, Jan. 2015.

V. Rodin et al., 'Generalized effective-medium model for the carrier mobility in amorphous organic semiconductors' Physical Review B, 91, 155203, 2015.

(56) References Cited

OTHER PUBLICATIONS

F. Suzuki et al., 'Effects of Structural and Energetic Disorders on Charge Transports in Crystal and Amorphous Organic Layers' Scientific Reports, 8:5203, Mar. 2018.
Yuchuan Shao et al., "Origin and elimination of photocurrent hysteresis by fullerene passivation in $CH_3NH_3PbI_3$ planar heterojunction solar cells" Nature Communications pp. 1-7 published Dec. 15, 2014.

* cited by examiner

N-TYPE SEMICONDUCTOR COMPOSITION, AND THIN FILM, ORGANIC PHOTOELECTRIC DEVICE, IMAGE SENSOR, AND ELECTRONIC DEVICE INCLUDING THE SAME

CROSS-REFERENCE TO RELATED APPLICATION

This application claims priority to and the benefit of Korean Patent Application No. 10-2019-0057222 filed in the Korean Intellectual Property Office on May 15, 2019, the entire contents of which are incorporated herein by reference.

BACKGROUND

1. Field

Example embodiments provide an N-type semiconductor composition and a thin film, an organic photoelectric device, an image sensor, and an electronic device including the same.

2. Description of the Related Art

Fullerene is a closed-cage molecule made of carbon and is used in various fields because of its stable structure and good electrical properties.

An organic photoelectric device is a device that converts light into an electrical signal using a photoelectric effect. The organic photoelectric device includes a photodiode and a phototransistor, and may be applied to an electronic device such as an image sensor. The organic photoelectric device may include fullerene in the active layer having high light absorption properties and good electrical properties.

However, fullerene may absorb light in a blue region and reduce color clarity of the organic photoelectric device to which the fullerene is applied.

Therefore, a method for controlling blue region absorption of fullerene may be desired.

SUMMARY

Example embodiments provide an N-type semiconductor composition capable of improving color clarity of an organic photoelectric device.

Example embodiments also provide an organic photoelectric device including the N-type semiconductor composition.

Example embodiments also provide an image sensor and an electronic device including the organic photoelectric device.

According to example embodiments, an N-type semiconductor composition includes fullerene or a fullerene derivative; and a fullerene subunit derivative represented by Chemical Formula 1.

[Chemical Formula 1]

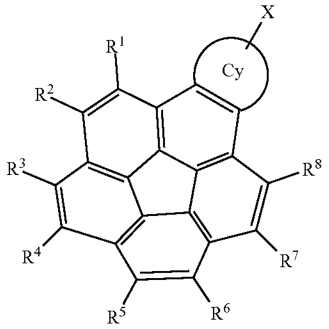

In Chemical Formula 1,

Cy is a cyclic hydrocarbon group selected from a C3 to C20 alicyclic hydrocarbon group and a C6 to C20 aromatic hydrocarbon group or a fused cyclic group of two or more cyclic hydrocarbon groups, X is at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, and $R^1$ to $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided at least one of $R^1$ to $R^8$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

In some embodiments, in Chemical Formula 1, at least one of $R^1$ to $R^3$ and at least one of $R^6$ to $R^8$ may be the same or different, and at least one of $R^1$ to $R^3$ and at least one of $R^6$ to $R^8$ may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

In some embodiments, in Chemical Formula 1, at least one bulky substituent of $R^1$ to $R^3$ and at least one bulky substituent of $R^6$ to $R^8$ may be present symmetrically with respect to an axis through Cy.

In some embodiments, in Chemical Formula 1, at least one of $R^1$ and $R^2$ and at least one of $R^7$ and $R^8$ may be the same or different, and may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

In some embodiments, in Chemical Formula 1, $R^2$ and $R^7$ may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof. And $R^1$, $R^3$, $R^4$, $R^5$, $R^6$, and $R^8$ may be hydrogen, deuterium, a halogen, a cyano group, a C1 to C20 linear alkyl group, or a combination thereof.

In some embodiments, in Chemical Formula 1, two adjacent substituents of $R^1$ to $R^3$ and two adjacent substituents of $R^6$ to $R^8$ may be linked to each other to provide a C3 to C20 alicyclic hydrocarbon group.

In some embodiments, in Chemical Formula 1, $R^2$ and $R^3$ may be linked to each other to provide a C3 to C20 alicyclic hydrocarbon group, and $R^6$ and $R^7$ may be linked to each other to provide a C3 to C20 alicyclic hydrocarbon group.

In some embodiments, the fullerene subunit derivative represented by Chemical Formula 1 may be a compound represented by Chemical Formula 1A.

[Chemical Formula 1A]

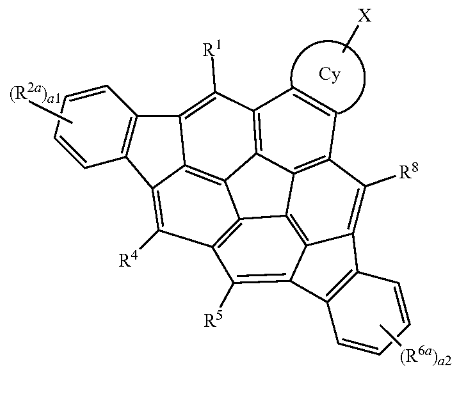

In Chemical Formula 1A,

Cy may be a cyclic hydrocarbon group selected from a C3 to C20 alicyclic hydrocarbon group and a C6 to C20 aromatic hydrocarbon group, or a fused cyclic group of two or more cyclic hydrocarbon groups, X may be at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, $R^1$, $R^{2a}$, $R^4$, $R^5$, $R^{6a}$, and $R^8$ independently may be hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, and a1 and a2 independently may be integers of 1 to 4.

In some embodiments, the cyclic hydrocarbon group in Cy may be a heterocyclic group including at least one functional group selected from —N═, —NR—, —O—, —S—, —Se—, —Te—, —C(═O)—, —C(═S)—, —C(═Se)—, —C(═Te)—, —C(═C(CN)$_2$)—, and —C(═NR)— wherein R may be a C1 to C10 alkyl group.

In some embodiments, in Chemical Formula 1, Cy may be pyrrole, furan, pyrroline, pyrrolidinedione, cyclopentanediene, cyclopentanedione, pyrrolo imidazole, pyrrolo imidazole including ketone (C═O) group in the ring, pyridine, pyrimidine, indole, phthalimide, benzimidazole, benzothiazole, or a fused ring of these rings and benzene rings.

In some embodiments, in Chemical Formula 1, Cy may be selected from moieties represented by Chemical Formulae 2A to 2C.

[Chemical Formula 2A]

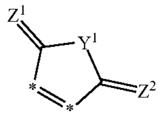

In Chemical Formula 2A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $Z^1$ and $Z^2$ are O, S, Se, Te, $C(CN)_2$, or $NR^d$, wherein $R^d$ is a C1 to C10 alkyl group or is linked to $Y^1$ of Chemical Formula 2A to provides a fused ring, and

*=* is a linking portion with Chemical Formula 1.

[Chemical Formula 2B]

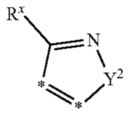

In Chemical Formula 2B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 2C]

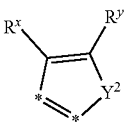

In Chemical Formula 2C, $Y^2$ is $CR^aR^b$, $NR^c$, O, S, Se, or Te, wherein $R^c$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

In Chemical Formula 1, Cy may be selected from moieties represented by Chemical Formulae 3A to 3D.

[Chemical Formula 3A]

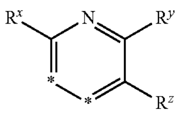

In Chemical Formula 3A, $R^x$, $R^y$, and $R^z$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$, $R^y$, and $R^z$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3B]

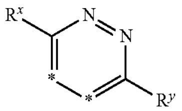

In Chemical Formula 3B, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3C]

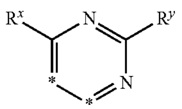

In Chemical Formula 3C, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3D]

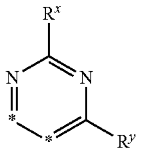

In Chemical Formula 3D, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

In some embodiments, in Chemical Formula 1, Cy may be selected from moieties represented by Chemical Formulae 4A to 4C.

[Chemical Formula 4A]

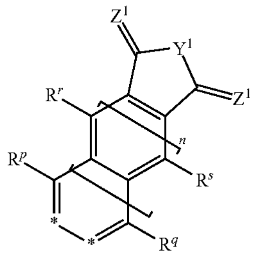

In Chemical Formula 4A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$, $R^q$, $R^r$, and $R^s$ are independently hydrogen, deuterium, or a C1 to C10 alkyl group, n is an integer of 0 to 2, $Z^1$ and $Z^2$ are O, S, Se, Te, $C(CN)_2$, or $NR^d$, wherein $R^d$ is a C1 to C10 alkyl group or is linked to $Y^1$ of Chemical Formula 4A to provides a fused ring, and

*=* is a linking portion with Chemical Formula 1.

[Chemical Formula 4B]

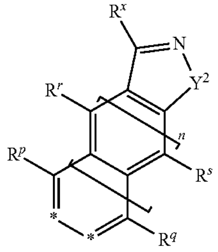

In Chemical Formula 4B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^p$, $R^q$, $R^r$, and $R^s$ are independently hydrogen, deuterium, or a C1 to C10 alkyl group, n is an integer of 0 to 2, and

*=* is a linking portion with Chemical Formula 1.

[Chemical Formula 4C]

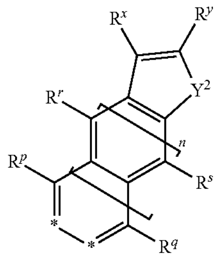

In Chemical Formula 4C, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$, $R^q$, $R^r$, and $R^s$ are independently hydrogen, deuterium, or a C1 to C10 alkyl group, n is an integer of 0 to 2, and

*=* is a linking portion with Chemical Formula 1.

In some embodiments, in Chemical Formula 1, at least one of $R^1$ to $R^8$ independently may be a group represented by Chemical Formula 5A.

[Chemical Formula 5A]

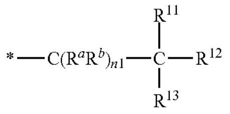

In Chemical Formula 5A, $R^a$ and $R^b$ are hydrogen, a halogen, a cyano group or a C1 to C6 alkyl group, n1 is an integer of 0 to 10, and $R^{11}$ to $R^{13}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

In some embodiments, at least one of $R^1$ to $R^8$ independently may be a group represented by Chemical Formula 5B,

[Chemical Formula 5B]

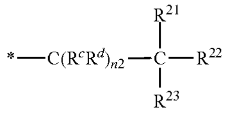

In Chemical Formula 5B, $R^c$ and $R^d$ are hydrogen, a halogen, a cyano group, a C1 to C6 alkyl group, a C1 to C6 alkoxy group, a C2 to C10 ether group, or a C2 to C10 ester group, n2 is an integer of 2 to 10, $-C(R^cR^d)-$ is replaced by a functional group selected from $-O-$, $-S-$, $-S(=O)-$, $-S(=O)_2-$, $-C(=O)-$, $-C(=O)O-$, $-OC(=O)-$, and a combination thereof, $R^{21}$ to $R^{23}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{21}$ to $R^{23}$ are a C1 to C10 alkyl group, a C1 to C10 alkoxy group, a C2 to C10 alkenyl group, or a C2 to C10 alkynyl group.

In some embodiments, in Chemical Formula 1, at least one of $R^1$ to $R^8$ independently may be a group represented by Chemical Formula 5C.

[Chemical Formula 5C]

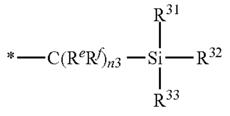

In Chemical Formula 5C, $R^e$ and $R^f$ are hydrogen, a halogen, a cyano group, or a C1 to C6 alkyl group, n3 is an integer of 0 to 10, and $R^{31}$ to $R^{33}$ are hydrogen, a halogen, a cyano group, a C1 to C10 alkyl group, a C1 to C10 alkoxy group, a C2 to C10 alkenyl group, a C2 to C10 alkynyl group, or a C1 to C10 alkylsilyl group, provided that at least two of $R^{31}$ to $R^{33}$ are a C1 to C10 alkyl group, a C1 to C10 alkoxy group, a C2 to C10 alkenyl group, or a C2 to C10 alkynyl group.

In some embodiments, in Chemical Formula 1, at least one of $R^1$ to $R^8$ independently may be an isopropyl group, a 1-methylpropyl group, an isobutyl group, a 1-methylbutyl group, a 1-ethylbutyl group, a 1-propylbutyl group, an isopentyl group, a 1-methylpentyl group, a 1-ethylpentyl group, a 1-propylpentyl group, a 2-methylpentyl group, a 2-ethylpentyl group, a 2-propylpentyl group, a 3-methylpentyl group, a 3-ethylpentyl group, a 3-propylpentyl group, an isohexyl group, a 1-methylhexyl group, a 1-ethylhexyl group, a 1-propylhexyl group, a 2-methylhexyl group, a 2-ethylhexyl group, a 2-propylhexyl group, a 3-methylhexyl group, a 3-ethylhexyl group, a 3-propylhexyl group, an isoheptyl group, a 1-methylheptyl group, a 1-ethylheptyl group, a 1-propylheptyl group, a 2-methylheptyl group, a 2-ethylheptyl group, a 2-propylheptyl group, a 3-methylheptyl group, a 3-ethylheptyl group, a 3-propylheptyl group, an isooctyl group, a 1-methyloctyl group, a 1-ethyloctyl group, a 1-propyloctyl group, a 2-methyloctyl group, a 2-ethyloctyl group, a 2-propyloctyl group, a 3-methyloctyl group, a 3-ethyloctyl group, a 3-propyloctyl group, a 1-methylnonyl group, a 1,1-dimethylnonyl group, a t-butyl group, a t-pentyl group, a t-hexyl group, a neopentyl group, or a neohexyl group.

In some embodiments, the fullerene subunit derivative may have an average distance of less than or equal to about 6 Å from a P-type semiconductor.

According to another embodiment, a thin film including the N-type semiconductor composition is provided.

In some embodiments, an absorption coefficient at a wavelength of about 450 nm of the thin film may be smaller than an absorption coefficient at a wavelength of about 450 nm of the thin film including unsubstituted C60 fullerene.

Another embodiment provides an organic photoelectric device including a first electrode and a second electrode facing each other, and an organic layer between the first electrode and the second electrode, wherein the organic layer includes the N-type semiconductor composition.

In some embodiments, an organic layer may include an active layer, and the active layer may include a P-type semiconductor and an N-type semiconductor forming a pn junction, and the N-type semiconductor may include the N-type semiconductor composition.

According to another embodiment, an image sensor including the organic photoelectric device is provided.

According to another embodiment, an electronic device including the organic photoelectric device is provided.

According to example embodiments, an N-type semiconductor composition includes fullerene or a fullerene derivative; and a fullerene subunit derivative represented by Chemical Formula 1.

[Chemical Formula 1]

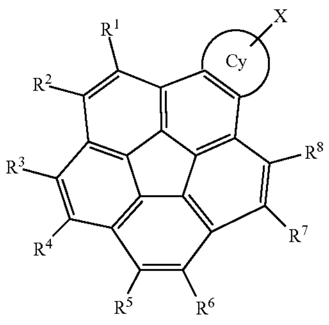

In Chemical Formula 1,

Cy includes a C3 to C20 alicyclic hydrocarbon group, a C6 to C20 aromatic hydrocarbon group, or a fused cyclic group of two or more cyclic hydrocarbon groups, X includes a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and $R^1$ to $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^1$ to $R^8$ includes a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof.

In some embodiments, the fullerene or the fullerene derivative may be the fullerene.

In some embodiments, the fullerene or the fullerene derivative may be the fullerene derivative.

In some embodiments, an organic photoelectric device may include first electrode and a second electrode facing each other, and an organic layer between the first electrode and the second electrode. The organic layer may include the N-type semiconductor composition.

In some embodiments, an image sensor may include organic photoelectric device.

The N-type semiconductor composition may improve color clarity of the organic photoelectric device by reducing absorption of the blue region of the fullerene or the fullerene derivative.

DETAILED DESCRIPTION

Figure 1:
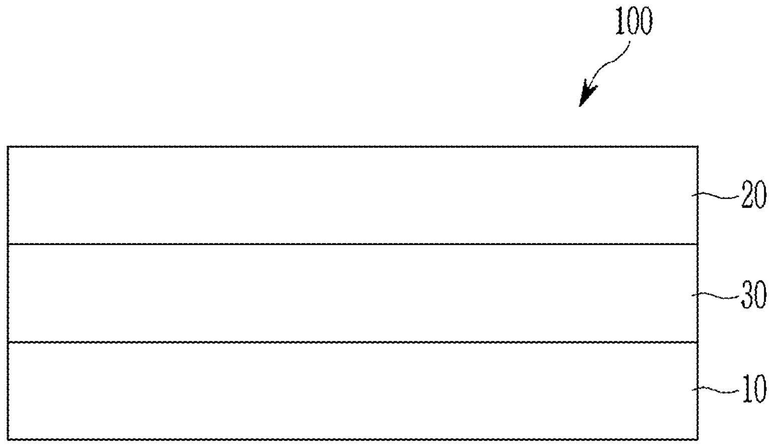
FIG. 1 is a cross-sectional view illustrating an organic photoelectric device according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "combination" includes two or more mixtures, intersubstitutions, and two or more stacked structures.

As used herein, when specific definition is not otherwise provided, "substituted" refers to replacement of a hydrogen of a compound, a functional group, or a moiety by a halogen atom (—F, —Cl, —Br, or —I), a hydroxyl group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C1 to C20 alkoxy group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, or a combination thereof (e.g., a C1 to C20 haloalkyl group such as a C1 to C20 trifluoroalkyl group).

As used herein, when a definition is not otherwise provided, "hetero" refers to one including one to three heteroatoms selected from N, O, S, P, Se, Te, and Si, and remaining carbons in a compound, a functional group, or a moiety.

As used herein, when a definition is not otherwise provided, "aryl group" refers to a group including at least one hydrocarbon aromatic moiety, for example all the elements of the hydrocarbon aromatic moiety having p-orbitals which form conjugation such as a phenyl group or a naphthyl group; two or more hydrocarbon aromatic moieties linked by a sigma bond such as a biphenyl group, a terphenyl group, or a quarterphenyl group; and two or more hydrocarbon aromatic moieties fused directly or indirectly to provide a non-aromatic fused ring such as a fluorenyl group.

As used herein, when a definition is not otherwise provided, "heterocyclic group" is a generic concept of a C2 to C30 (e.g., C2 to C20) heteroaryl group, a C2 to C30 (e.g., C2 to C20) heterocycloalkyl group, or a fused cyclic group thereof, and may include at least one (e.g., 1 to 3) heteroatom instead of carbon (C) in a ring such as an aryl group, a cycloalkyl group, a fused cyclic group thereof, or a combination thereof, wherein the heteroatom may be for example N, O, S, P, Se, Te, and/or Si, but is not limited thereto. When the heterocyclic group is a fused cyclic group, at least one (e.g., 1 to 3) heteroatom may be included in an entire ring or each ring of the heterocyclic group.

As used herein, when a definition is not otherwise provided, "heteroaryl group" refers to an aryl group including at least one heteroatom, wherein the heteroatom may be for example N, O, S, P, Se, Te, and/or Si, but is not limited thereto. At least two heteroaryl groups may be linked directly through a sigma bond or at least two heterocyclic groups may be fused with each other. When the heteroaryl group is a fused ring, each ring may include one to three heteroatoms.

As used herein, when a definition is not otherwise provided, "heteroalkyl group" refers to an alkyl group including at least one heteroatom in the main chain of the alkyl group and may be specifically an alkyl group in which at least one methylene group is replaced by —O—, —S—, —C(═O)—, —C(═S)—, —OC(═O)—, and —C(═O)O—.

As used herein, when a definition is not otherwise provided, "cyclic hydrocarbon group" refers to a C3 to C20 alicyclic hydrocarbon group, a C6 to C20 aromatic hydrocarbon group, a fused cyclic group of two or more cyclic hydrocarbon groups, or a heterocyclic group including a heteroatom therein.

As used herein, when a definition is not otherwise provided, "alicyclic hydrocarbon group" refers to at least one non-aromatic ring (alicyclic ring) or a fused ring in which these non-aromatic rings are fused to each other which is selected from a C3 to C30 cycloalkyl group, for example a C3 to C20 cycloalkyl group or a C3 to C10 cycloalkyl group; a C3 to C30 cycloalkenyl group, for example a C3 to C20 cycloalkenyl group or a C3 to C10 cycloalkenyl group; and a C2 to C30 heterocycloalkyl group, for example a C2 to C20 heterocycloalkyl group or a C3 to C10 heterocycloalkyl group.

As used herein, when a definition is not otherwise provided, "aromatic hydrocarbon group" may include at least one aromatic ring (arene ring) or a fused ring thereof such as a C6 to C30 aryl group, for example a C6 to C20 aryl group or a C6 to C10 aryl group.

As used herein, when a definition is not otherwise provided, "bulky substituent" refers to a substituted or unsubstituted branched alkyl group, a substituted or unsubstituted branched alkoxy group, a substituted or unsubstituted branched alkylsilyl group, a substituted or unsubstituted branched heteroalkyl group, a substituted or unsubstituted aryl group, a substituted or unsubstituted heteroaryl group, a substituted or unsubstituted cycloalkyl group, a substituted or unsubstituted heterocycloalkyl group, or a combination thereof. In some embodiment, the "bulky substituent" refers to a substituted or unsubstituted C3 to C20 (e.g., C4 to C20) branched alkyl group, a substituted or unsubstituted C3 to C20 (e.g., C4 to C20) branched alkoxy group, a substituted or unsubstituted C3 to C20 (e.g., C4 to C20) branched alkylsilyl group, a substituted or unsubstituted C3 to C20 (e.g., C4 to C20) branched heteroalkyl group, a substituted or unsubstituted C6 to C30 (e.g., C6 to C20) aryl group, a substituted or unsubstituted C2 to C30 (e.g., C3 to C20) heteroaryl group, a substituted or unsubstituted C3 to C30 (e.g., C4 to C20) cycloalkyl group, a substituted or unsubstituted C3 to C30 (e.g., C4 to C20) heterocycloalkyl group, and a combination thereof.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C.

When the term "about" is used in this specification in connection with a numerical value, it is intended that the associated numerical value include a tolerance of ±10% around the stated numerical value. When ranges are specified, the range includes all values therebetween such as increments of 0.1%.

Hereinafter, an N-type semiconductor composition according to an embodiment is described.

According to an embodiment, an N-type semiconductor composition includes fullerene or a fullerene derivative; and a fullerene subunit derivative represented by Chemical Formula 1.

[Chemical Formula 1]

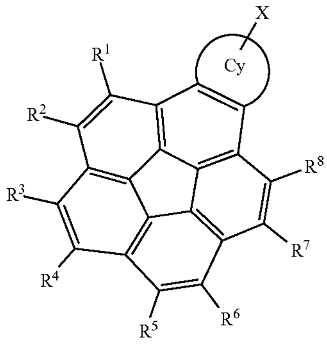

In Chemical Formula 1,

Cy is a cyclic hydrocarbon group selected from a C3 to C20 alicyclic hydrocarbon group and a C6 to C20 aromatic hydrocarbon group, or a fused cyclic group of two or more cyclic hydrocarbon groups, X is at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, and $R^1$ to $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided at least one of $R^1$ to $R^8$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

The fullerene subunit derivative of Chemical Formula 1 includes a cyclic hydrocarbon group (Cy) having at least one bulky substituent (X) and further includes at least one bulky substituent at a position (at least one of $R^1$ to $R^8$) besides Cy and thereby crystallinity of the fullerene subunit derivatives may be suppressed effectively. The fullerene subunit derivative of Chemical Formula 1 may interact with the fullerene or fullerene derivative, and thereby aggregation of the fullerene or fullerene derivative may be suppressed effectively. Light absorption in a blue region (about 400 nm to about 500 nm) may be significantly reduced by suppressing the aggregation of the fullerene or the fullerene derivative, thereby improving color clarity of the device.

The bulky substituent (X) may effectively control steric hindrance between the fullerene subunit derivatives to maintain a constant interval. The bulky substituents of at least one of $R^1$ to $R^8$ may lower crystallinity of the fullerene subunit derivative and may be mixed well with the P-type semiconductor and the N-type semiconductor (fullerene or fullerene derivative) in an active layer. In addition, the bulky substituents of at least one of $R^1$ to $R^8$ may inhibit aggregation of the fullerene or fullerene derivative by allowing a corannulene skeleton of the derivative to surround the fullerene or fullerene derivative well. In addition, the bulky substituent of at least one of $R^1$ to $R^8$ may improve thermal stability of the fullerene subunit derivative which may improve high temperature characteristics when applied to a device.

The fullerene subunit derivative of Chemical Formula 1 has a structure capable of inhibiting aggregation of the fullerene or fullerene derivative, but does not expand the conjugated structure of corannulene, thereby suppressing an increase in crystallinity and enabling sublimation purification to be advantageous in a thin film formation process.

The cyclic hydrocarbon group may include one or more heteroatoms in the ring. Specifically, the cyclic hydrocarbon group may be a heterocyclic group including at least one functional group selected from —N=, —NR—, —O—, —S—, —Se—, —Te—, —C(=O)—, —C(=S)—, —C(=Se)—, —C(=Te)—, —C(=C(CN)$_2$)—, and —C(=NR)— wherein R is a C1 to C10 alkyl group. As such, when Cy is a heterocyclic group, N-type properties of the fullerene subunit derivative may be further enhanced.

The HOMO/LUMO levels of the fullerene subunit derivative may be adjusted by a combination of the cyclic hydrocarbon group and the bulky substituent (X) substituted therein. For example, when Cy is a hydrocarbon group that does not include an electron withdrawing functional group (e.g., —C(=O)—, —N=, —NR—, etc.), an electron withdrawing functional group may be introduced into the bulky substituent (X). Examples of the bulky substituent (X) having an electron withdrawing functional group include an N-containing cyclic group such as a pyrrolyl group, a pyridyl group, a pyrimidyl group, a triazinyl group, and the like; or a C6 to C20 aryl group substituted with a fluorine (F) group, a cyano (CN) group, a C1 to C10 carboxyl group or an ester group (e.g., acetate group) or a C1 to C10 trifluoroalkyl group (e.g., trifluoromethyl ($CF_3$)).

At least two, for example three or four of $R^1$ to $R^8$ may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

In Chemical Formula 1, at least one of $R^1$ to $R^3$ and at least one of $R^6$ to $R^8$ may be the same or different, and may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

At least one bulky substituent of $R^1$ to $R^3$ and at least one bulky substituent of $R^6$ to $R^8$ may be present at positions symmetrical with respect to Cy.

In Chemical Formula 1, at least two of $R^1$ to $R^8$ may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

In Chemical Formula 1, when including two or more bulky substituents at positions symmetrical with respect to Cy, the fullerene subunit derivative may effectively cover the fullerene or the fullerene derivative, thereby suppressing their aggregation.

The fullerene may be fullerenes of C60 to C120, and specifically, may be C60, C70, C74, C76, C78, C80, C82, C84, C90, or C96, but is not limited thereto.

The fullerene derivative refers to a compound having a substituent on the fullerene. Examples of the substituent may be an alkyl group, an aryl group. or a heterocyclic group. The alkyl group may be a C1 to C12 alkyl group, for example, a C1 to C5 alkyl group. The aryl group may be a phenyl group, a naphthyl group, or an anthracenyl group. Herein, the heterocyclic group may be a furyl group, a thienyl group, a pyrrolyl group, an oxazolyl group, a pyridyl group, a quinolyl group, or a carbazolyl group.

Specific examples of the fullerene derivative may include phenyl-C61-butyric acid methylester (PCBM, [6,6]-phenyl-C61-butyric acid methyl ester), and ICBA (indene-C60 bisadduct), and ICMA (indene-C60 monoadduct), but are not limited thereto.

In Chemical Formula 1, at least one of $R^1$ to $R^3$ and at least one of $R^6$ to $R^8$ may be the same or different, and may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof. In this case, steric hindrance may be effectively controlled to suppress aggregation of fullerene or fullerene derivative in the deposition process.

In Chemical Formula 1, at least one of $R^1$ and $R^2$ and at least one of $R^7$ and $R^8$ may be the same or different, and may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^3$, $R^4$, $R^5$, and $R^6$ may be hydrogen, deuterium, a halogen, a cyano group, a C1 to C20 linear alkyl group, or a combination thereof. In this case, steric hindrance may be effectively controlled to suppress aggregation of fullerene or fullerene derivative in the deposition process.

In Chemical Formula 1 $R^2$ and $R^7$ may be a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^1$, $R^3$, $R^4$, $R^5$, $R^6$, and $R^8$ may be hydrogen, deuterium, a halogen, a cyano group, a C1 to C20 linear alkyl group, or a combination thereof. In this case, by having a bulky substituent on both sides with respect to Cy, the steric hindrance effect may be effectively controlled to suppress aggregation of fullerene or fullerene derivative in the deposition process.

According to an embodiment, in Chemical Formula 1, two adjacent substituents of $R^1$ to $R^3$ and two adjacent substituents of $R^6$ to $R^8$ may be linked to each other to form a C3 to C20 alicyclic hydrocarbon group. Such C3 to C20 alicyclic hydrocarbon group may inhibit expansion of the conjugated structure of corannulene to inhibit an increase in crystallinity. The C3 to C20 alicyclic hydrocarbon group may be fused with a C6 to C20 aromatic hydrocarbon group.

In Chemical Formula 1, $R^2$ and $R^3$ may be linked to each other to form a C3 to C20 alicyclic hydrocarbon group, and $R^6$ and $R^7$ may be linked to each other to form a C3 to C20 alicyclic hydrocarbon group. The C3 to C20 alicyclic hydrocarbon group may be fused with a C6 to C20 aromatic hydrocarbon group. The C3 to C20 alicyclic hydrocarbon group may be a pentagonal ring, and a structure in which the pentagonal ring may be fused with a benzene ring is represented by Chemical Formula 1A.

[Chemical Formula 1A]

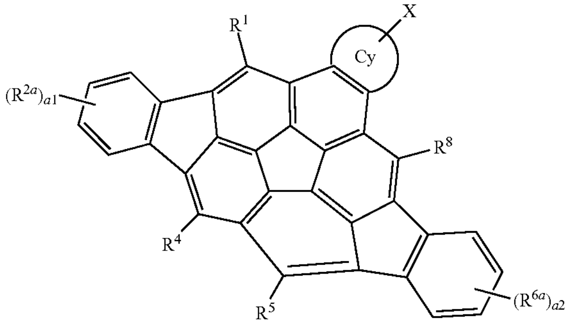

In Chemical Formula 1A,

Cy is a cyclic hydrocarbon group selected from a C3 to C20 alicyclic hydrocarbon group and a C6 to C20 aromatic hydrocarbon group or a fused cyclic group of two or more cyclic hydrocarbon groups, X is at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, $R^1$, $R^{2a}$, $R^4$, $R^5$, $R^{6a}$, and $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, and a1 and a2 are independently integers of 1 to 4.

In Chemical Formula 1, Cy may be pyrrole, furan, pyrroline, pyrrolidinedione, cyclopentanediene, cyclopentanedione, pyrrolo imidazole, pyrrolo imidazole including a ketone (C═O) group in the ring, pyridine, pyrimidine, indole, pyridine, phthalimide, benzimidazole, benzothiazole, or a fused ring of these and benzene rings.

In Chemical Formula 1, Cy may be a moiety represented by Chemical Formula 2A.

[Chemical Formula 2A]

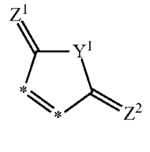

In Chemical Formula 2A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $Z^1$ and $Z^2$ are O, S, Se, Te, $C(CN)_2$, or $NR^d$, wherein $R^d$ is a C1 to C10 alkyl group or is linked to $Y^1$ of Chemical Formula 2A to provides a fused ring, and

*=* is a linking portion with Chemical Formula 1.

For example, the moiety represented by Chemical Formula 2A may be a moiety represented by Chemical Formula 2A-1.

[Chemical Formula 2A-1]

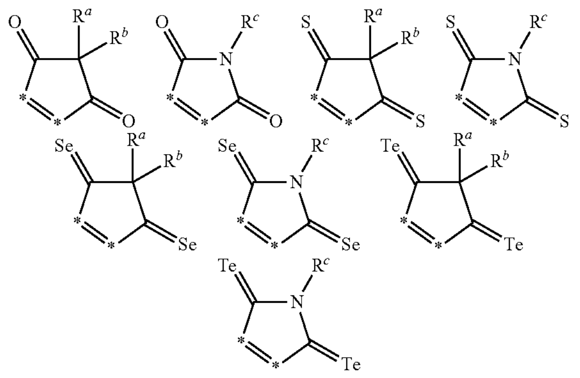

In Chemical Formula 2A-1, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

When $Z^2$ is $NR^d$ and $R^d$ is linked to $Y^1$ of Chemical Formula 2A to form a fused ring, Chemical Formula 2A may be a moiety represented by Chemical Formula 2A-2.

[Chemical Formula 2A-2]

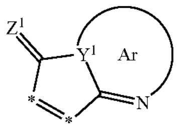

In Chemical Formula 2A-2, $Y^1$ is $CR^a$ or N, $Z^1$ is O, S, Se, Te, $C(CN)_2$, or $NR^d$, and Ar is a C6 to C30 aryl group or a C3 to C30 heteroaryl group.

In Chemical Formula 1, Cy may be a moiety represented by Chemical Formula 2B.

[Chemical Formula 2B]

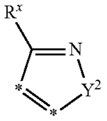

In Chemical Formula 2B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

For example, the moiety represented by Chemical Formula 2B may be a moiety represented by Chemical Formula 2B-1.

[Chemical Formula 2B-1]

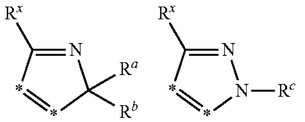

In Chemical Formula 2B-1, $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

For example, the moiety represented by Chemical Formula 2B may be selected from moieties represented by Chemical Formula 2B-2.

[Chemical Formula 2B-2]

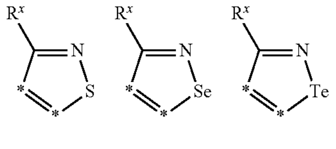

In Chemical Formula 2B-2, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

In Chemical Formula 1, Cy may be a moiety represented by Chemical Formula 2C.

[Chemical Formula 2C]

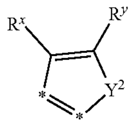

In Chemical Formula 2C, $Y^2$ is $CR^aR^b$, $NR^c$, O, S, Se, or Te, wherein $R^c$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

For example, the moiety represented by Chemical Formula 2C may be a moiety represented by Chemical Formula 2C-1.

[Chemical Formula 2C-1]

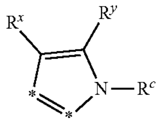

In Chemical Formula 2C-1, $R^c$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^c$, $R^x$, and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

For example, the moiety represented by Chemical Formula 2C may be a moiety represented by Chemical Formula 2C-2.

[Chemical Formula 2C-2]

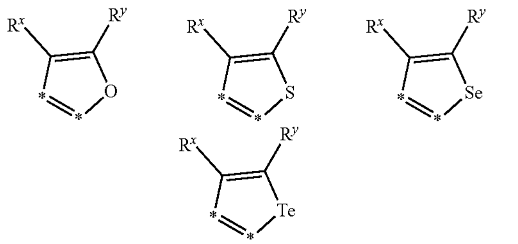

In Chemical Formula 2C-2, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

In Chemical Formula 1, Cy may be selected from moieties represented by Chemical Formulae 3A to 3D.

[Chemical Formula 3A]

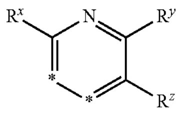

In Chemical Formula 3A, $R^x$, $R^y$, and $R^z$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$, $R^y$, and $R^z$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3B]

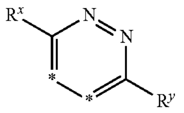

In Chemical Formula 3B, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3C]

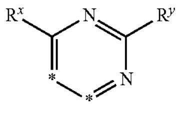

In Chemical Formula 3C, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

[Chemical Formula 3D]

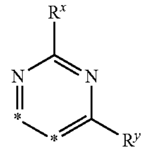

In Chemical Formula 3D, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

In Chemical Formula 1, Cy may be a moiety represented by Chemical Formula 4A.

[Chemical Formula 4A]

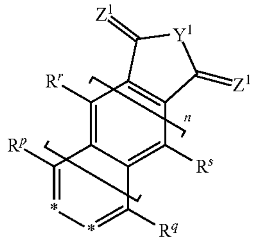

In Chemical Formula 4A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$, $R^q$, $R^r$, and $R^s$ are independently hydrogen, deuterium, or a C1 to C10 alkyl group, n is an integer of 0 to 2, $Z^1$ and $Z^2$ are O, S, Se, Te, $C(CN)_2$, or $NR^d$, wherein $R^d$ is a C1 to C10 alkyl group or is linked to $Y^1$ of Chemical Formula 4A to provides a fused ring, and

*=* is a linking portion with Chemical Formula 1.

For example, the moiety represented by Chemical Formula 4A may be a moiety represented by Chemical Formula 4A-1. Chemical Formula 4A-1 illustrates the case where n of Chemical Formula 4A is 0, but the compound where n of Chemical Formula 4A is 1 or 2 may be represented in the same manner as in Chemical Formula 4A-1.

[Chemical Formula 4A-1]

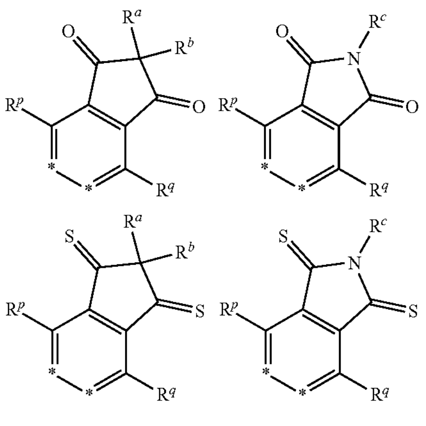

-continued

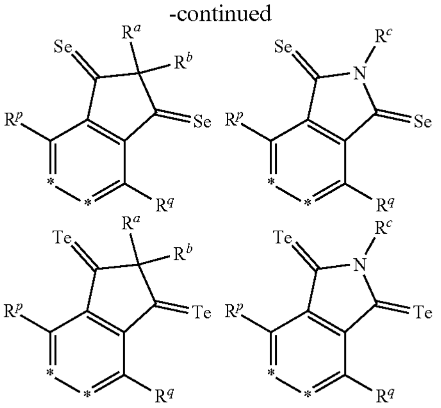

In Chemical Formula 4A-1, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$ and $R^q$ are independently hydrogen, deuterium, or a C1 to C10 alkyl group, and

*=* is a linking portion with Chemical Formula 1.

In Chemical Formula 1, Cy may be a moiety represented by Chemical Formula 4B.

[Chemical Formula 4B]

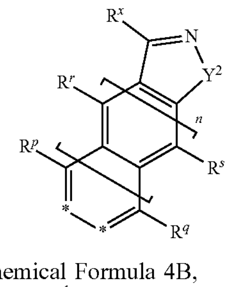

In Chemical Formula 4B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^p$, $R^q$, $R^r$, and $R^s$ are independently hydrogen, deuterium, or a C1 to C10 alkyl group, n is an integer of 0 to 2, and

*=* is a linking portion with Chemical Formula 1.

For example, the moiety represented by Chemical Formula 4B may be a moiety represented by Chemical Formula 4B-1. Chemical Formula 4B-1 illustrates the case where n of Chemical Formula 4B is 0, but the compound where n of Chemical Formula 4B is 1 or 2 may be represented in the same manner as in Chemical Formula 4B-1.

[Chemical Formula 4B-1]

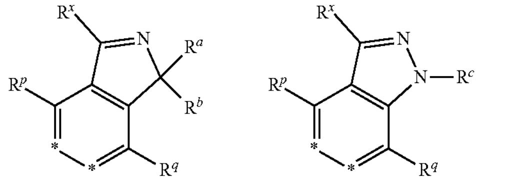

In Chemical Formula 4B-1, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^p$ and $R^q$ are independently hydrogen, deuterium, or a C1 to C10 alkyl group, and

*=* is a linking portion with Chemical Formula 1.

For example, the moiety represented by Chemical Formula 4B may be a moiety represented by Chemical Formula 4B-2. Chemical Formula 4B-2 illustrates the case where n of Chemical Formula 4B is 0, but the compound where n of Chemical Formula 4B is 1 or 2 may be represented in the same manner as in Chemical Formula 4B-2.

[Chemical Formula 4B-2]

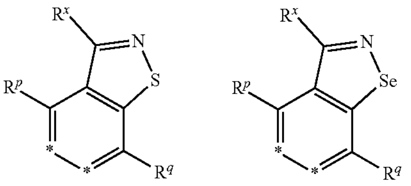

-continued

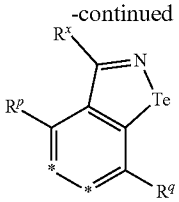

In Chemical Formula 4B-2, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$ and $R^q$ are independently hydrogen, deuterium, or a C1 to C10 alkyl group, and

*=* is a linking portion with Chemical Formula 1.

In Chemical Formula 1, Cy may be selected from a moiety represented by Chemical Formula 4C.

[Chemical Formula 4C]

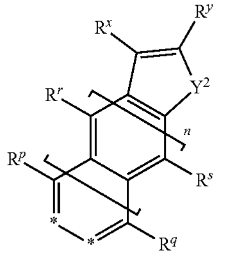

In Chemical Formula 4C, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^p$, $R^q$, $R^r$, and $R^s$ are independently hydrogen, deuterium, or a C1 to C10 alkyl group, n is an integer of 0 to 2, and

*=* is a linking portion with Chemical Formula 1.

For example, the moiety represented by Chemical Formula 4C may be a moiety represented by Chemical Formula 4C-1. Chemical Formula 4C-1 illustrates the case where n of Chemical Formula 4C is 0, but the compound where n of Chemical Formula 4C is 1 or 2 may be represented in the same manner as in Chemical Formula 4C-1.

[Chemical Formula 4C-1]

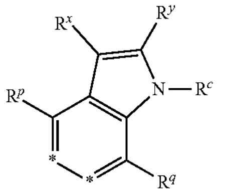

In Chemical Formula 4C-1, $R^c$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^c$, $R^x$, and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$ and $R^q$ are independently hydrogen, deuterium, or a C1 to C10 alkyl group, and

*=* is a linking portion with Chemical Formula 1.

For example, the moiety represented by Chemical Formula 4C may be a moiety represented by Chemical Formula 4C-2. Chemical Formula 4C-2 illustrates the case where n of Chemical Formula 4C is 0, but the compound where n of Chemical Formula 4C is 1 or 2 may be represented in the same manner as in Chemical Formula 4C-2.

[Chemical Formula 4C-2]

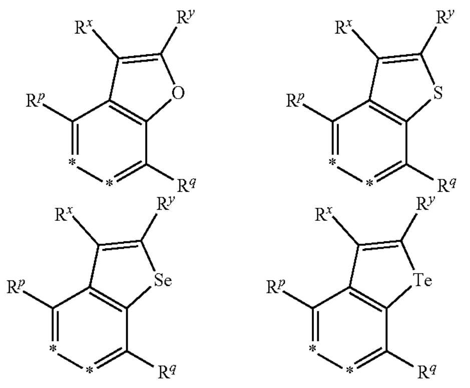

In Chemical Formula 4C-2, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$ and $R^q$ are independently hydrogen, deuterium, or a C1 to C10 alkyl group, and

*=* is a linking portion with Chemical Formula 1.

In an embodiment, the substituted or unsubstituted C3 to C20 branched alkyl group and a substituted or unsubstituted C3 to C20 branched alkoxy group may be represented by Chemical Formula 5A.

[Chemical Formula 5A]

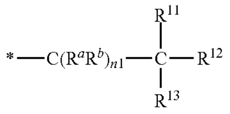

In Chemical Formula 5A, $R^a$ and $R^b$ are hydrogen, a halogen, a cyano group, or a C1 to C6 alkyl group, n1 is an integer of 0 to 10, and $R^{11}$ to $R^{13}$ are hydrogen, a halogen, a cyano group, a C1 to C10 alkyl group, a C1 to C10 alkoxy group, a C2 to C10 alkenyl group, a C2 to C10 alkynyl group, or a C1 to C10 alkylsilyl group, provided that at least two of $R^{11}$ to $R^{13}$ area C1 to C10 alkyl group, a C1 to C10 alkoxy group, a C2 to C10 alkenyl group, or a C2 to C10 alkynyl group.

In an embodiment, the C3 to C20 branched alkyl group may be an isopropyl group, a 1-methylpropyl group, an isobutyl group, a 1-methylbutyl group, a 1-ethylbutyl group, a 1-propylbutyl group, an isopentyl group, a 1-methylpentyl group, a 1-ethylpentyl group, a 1-propylpentyl group, a 2-methylpentyl group, a 2-ethylpentyl group, a 2-propylpentyl group, a 3-methylpentyl group, a 3-ethylpentyl group, a 3-propylpentyl group, an isohexyl group, a 1-methylhexyl group, a 1-ethylhexyl group, a 1-propylhexyl group, a 2-methylhexyl group, a 2-ethylhexyl group, a 2-propylhexyl group, a 3-methylhexyl group, a 3-ethylhexyl group, a 3-propylhexyl group, an isoheptyl group, a 1-methylheptyl group, a 1-ethylheptyl group, a 1-propylheptyl group, a 2-methylheptyl group, a 2-ethylheptyl group, a 2-propylheptyl group, a 3-methylheptyl group, a 3-ethylheptyl group, a 3-propylheptyl group, an isooctyl group, a 1-methyloctyl group, a 1-ethyloctyl group, a 1-propyloctyl group, a 2-methyloctyl group, a 2-ethyloctyl group, a 2-propyloctyl group, a 3-methyloctyl group, a 3-ethyloctyl group, a 3-propyloctyl group, a 1-methylnonyl group, a 1,1-dimethylnonyl group, a t-butyl group, a t-pentyl group, a t-hexyl group, a neopentyl group, or a neohexyl group, but is not limited thereto.

In an embodiment, the C3 to C20 branched heteroalkyl group may be a group in which $—C(R^cR^d)—$ is replaced by a functional group selected from —O—, —S—, —S(=O)—, $—S(=O)_2—$, —C(=O)—, —C(=O)O—, —OC(=O)—, or a combination thereof and may be represented by Chemical Formula 5B.

[Chemical Formula 5B]

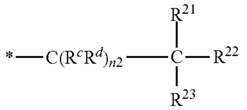

In Chemical Formula 5B, $R^c$ and $R^d$ are hydrogen, a halogen, a cyano group, a C1 to C6 alkyl group, a C1 to C6 alkoxy group, a C2 to C10 ether group, or a C2 to C10 ester group, n2 is an integer of 2 to 10, and $R^{21}$ to $R^{23}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{21}$ to $R^{23}$ are a C1 to C10 alkyl group, a C1 to C10 alkoxy group, a C2 to C10 alkenyl group, or a C2 to C10 alkynyl group.

In an embodiment, the substituted or unsubstituted C3 to C20 branched alkylsilyl group may be represented by Chemical Formula 5C.

[Chemical Formula 5C]

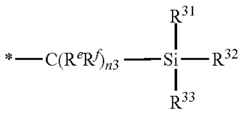

In Chemical Formula 5C, $R^e$ and $R^f$ are hydrogen, a halogen, a cyano group, or a C1 to C6 alkyl group, n3 is an integer of 0 to 10, and $R^{31}$ to $R^{33}$ are hydrogen, a halogen, a cyano group, a C1 to C10 alkyl group, a C1 to C10 alkoxy group, a C2 to C10 alkenyl group, a C2 to C10 alkynyl group, or a C1 to C10 alkylsilyl group, provided that at least two of $R^{31}$ to $R^{33}$ are a C1 to C10 alkyl group, a C1 to C10 alkoxy group, a C2 to C10 alkenyl group, or a C2 to C10 alkynyl group.

Specific examples of the fullerene subunit derivatives include compounds of Groups 1 to 8.

[Group 1]

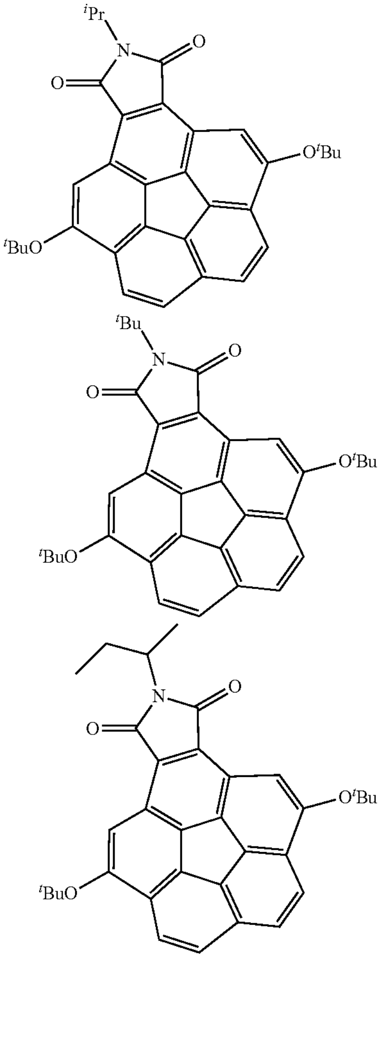

-continued
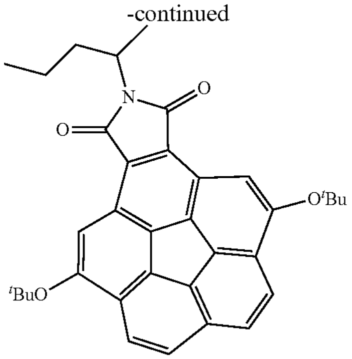
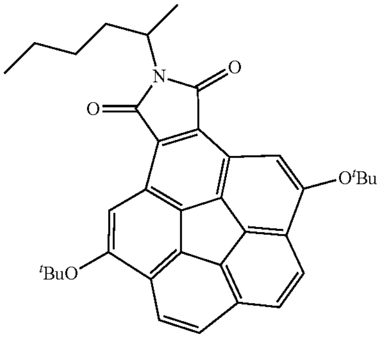
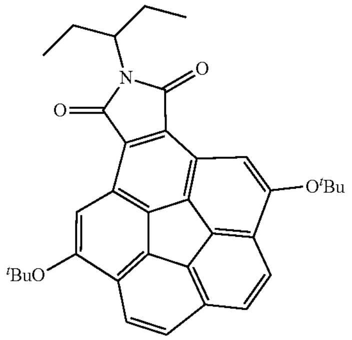
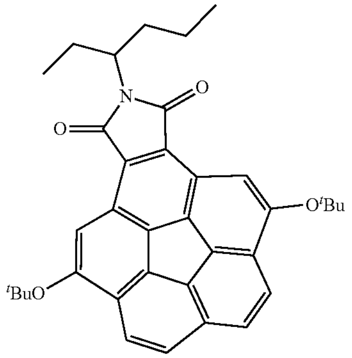
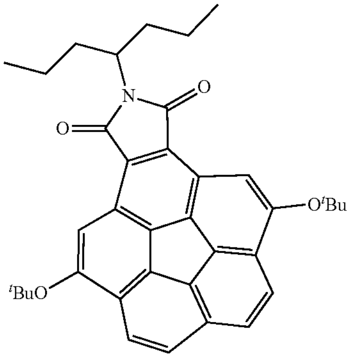
-continued
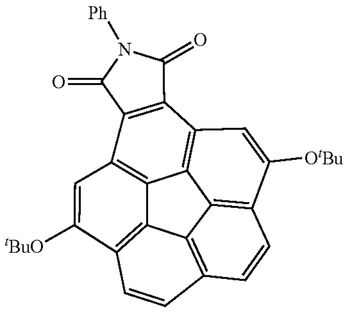
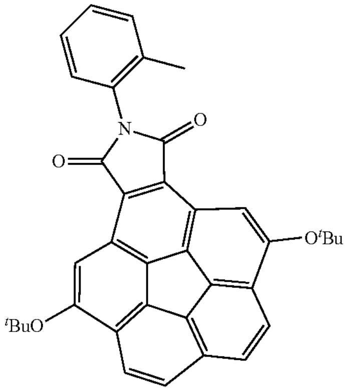
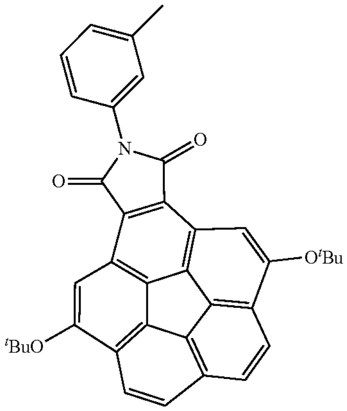
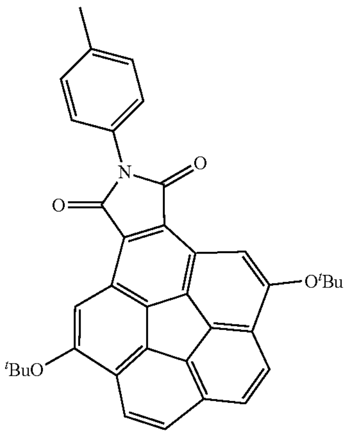

-continued
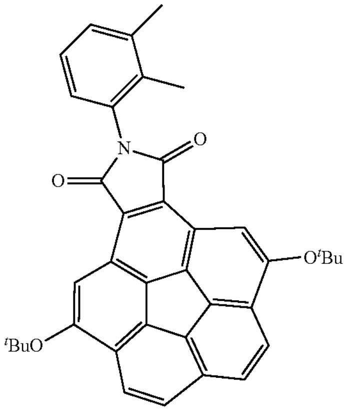
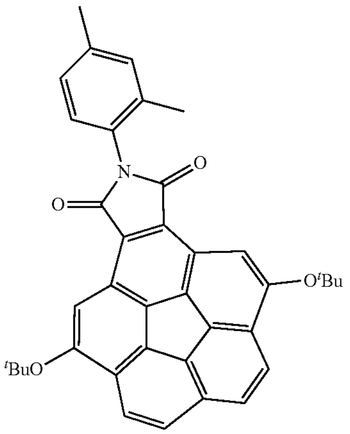
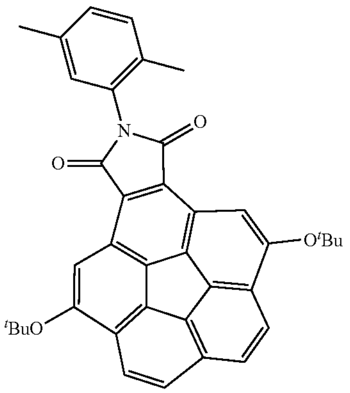
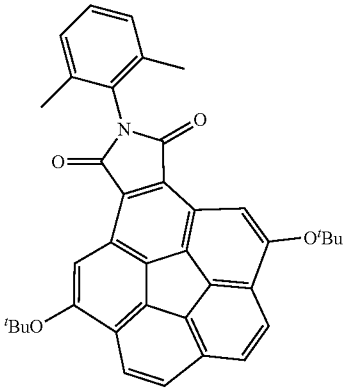
-continued
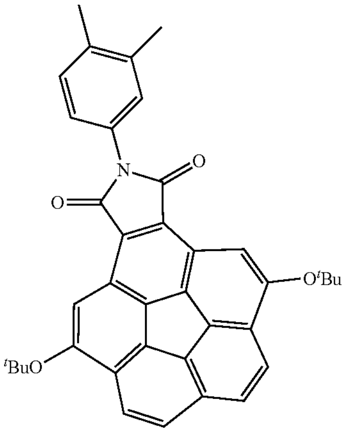
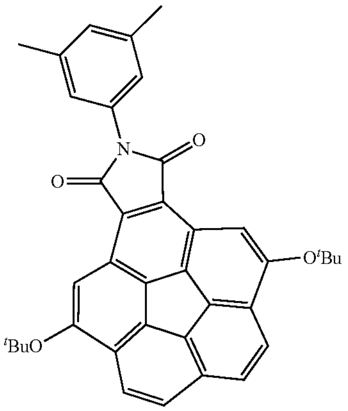
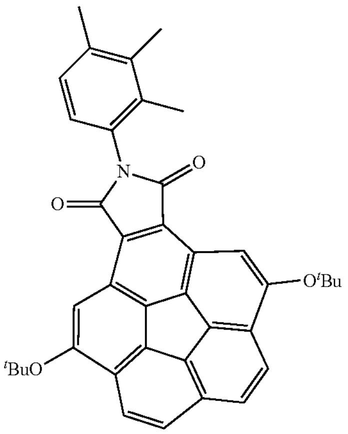
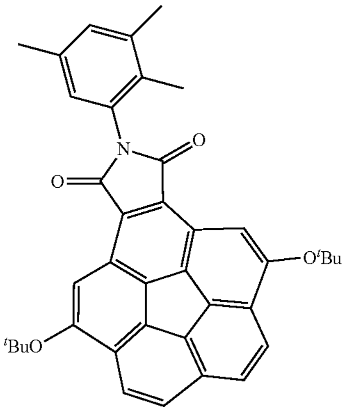

-continued
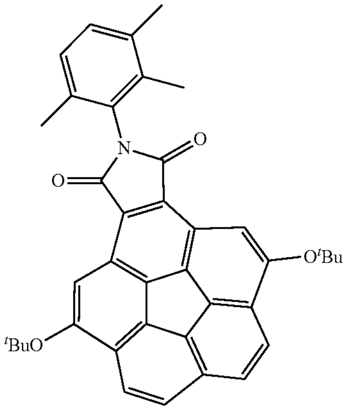
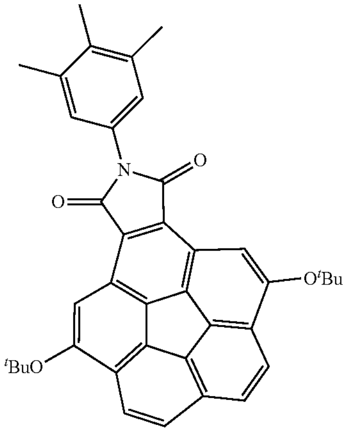
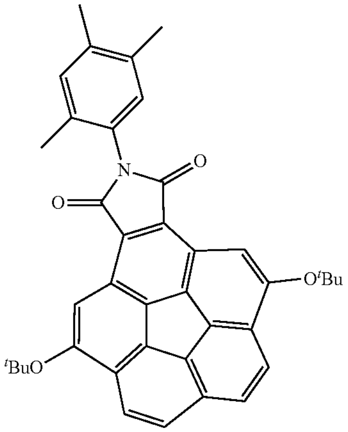
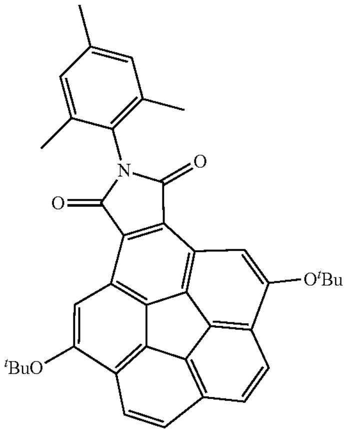
-continued
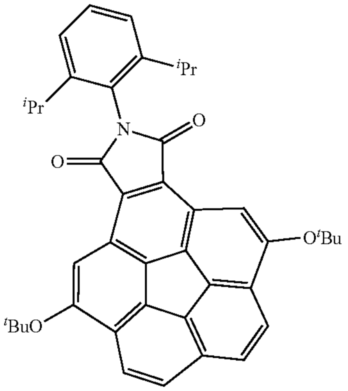
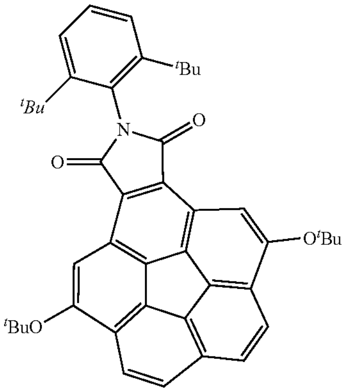
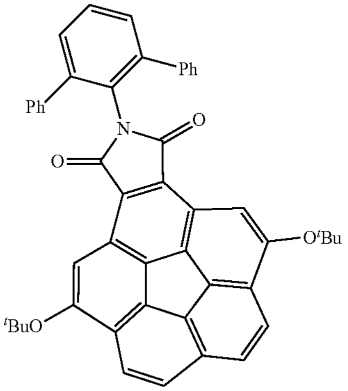
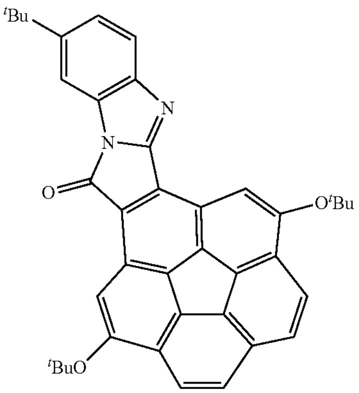

-continued
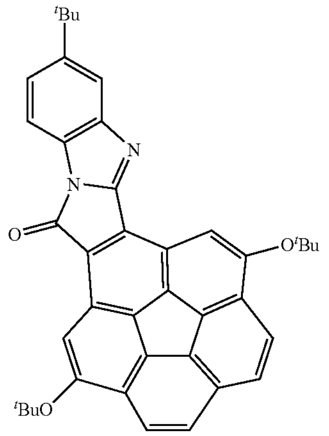
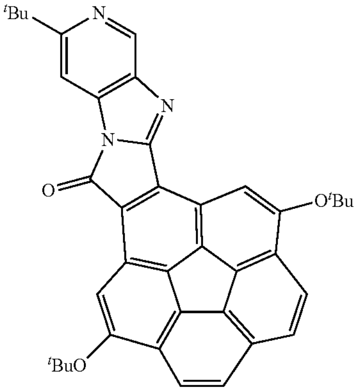
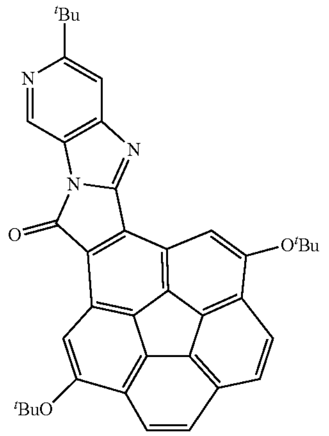
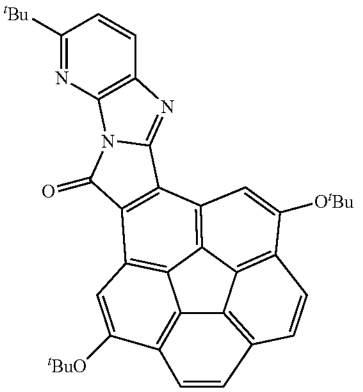
-continued
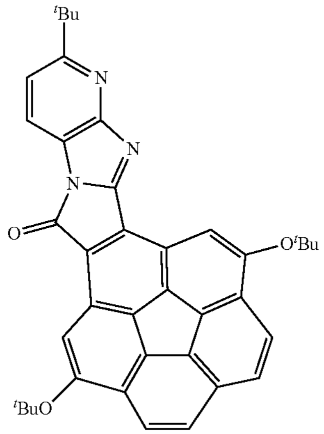
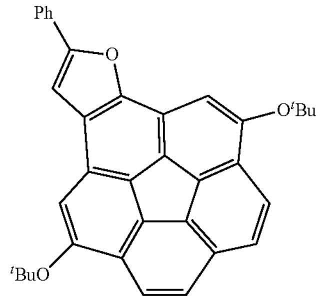
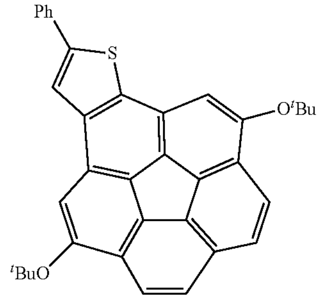
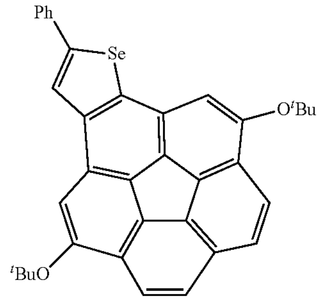
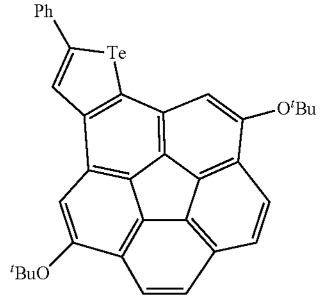

-continued
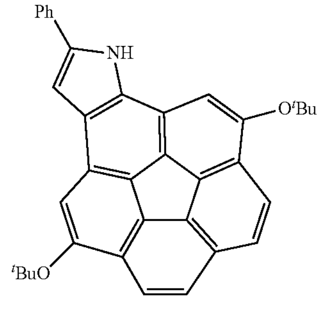
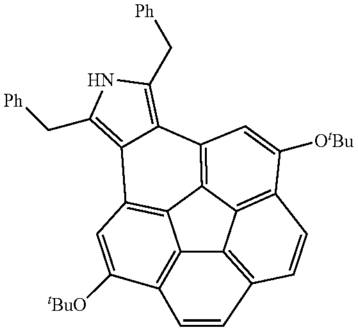
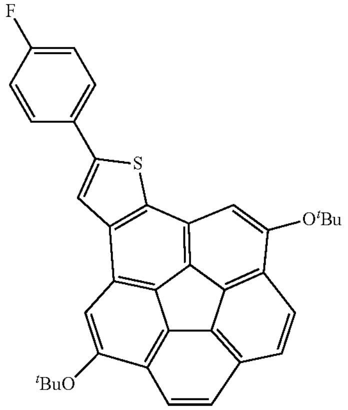
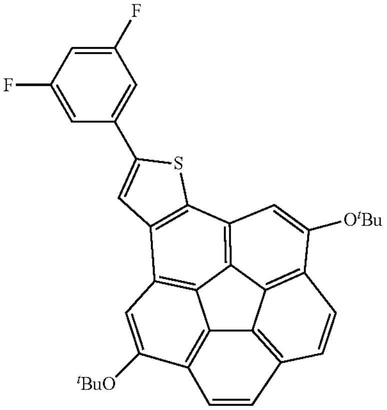
-continued
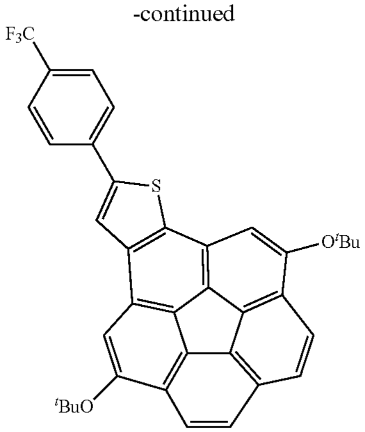
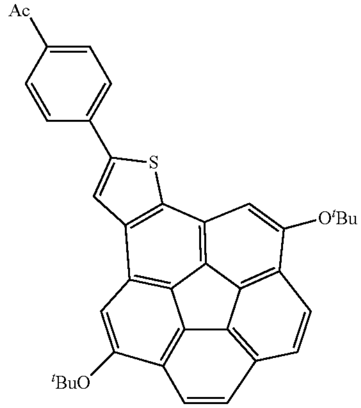
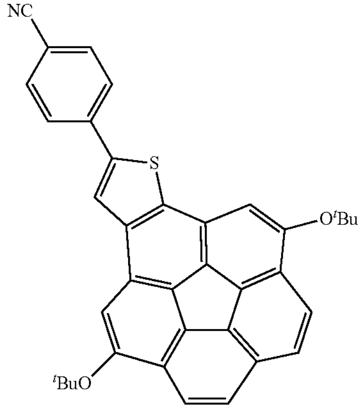
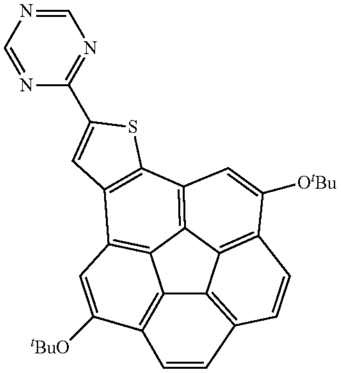
Branched alkyl groups such as an isopropyl (iPr) group, a tertiary butyl (tBu) group, a 2-methyl propyl group, a trimethylsilyl (TMS) group, etc. may be substituted instead of the two substituents ($O^tBu$) groups of the corannulene of Group 1. Group 2 illustrates structures which are substituted with a tertiary butyl ($^t$Bu) group instead of the two substituents (O$^t$Bu) groups of corannulene in Group 1 and Group 3 illustrates structures which are substituted with a trimethylsilyl (TMS) group.
[Group 2]
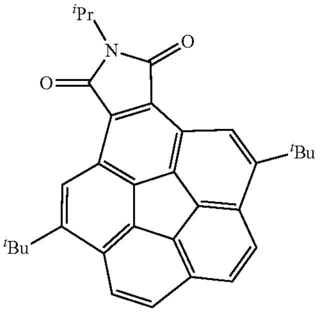
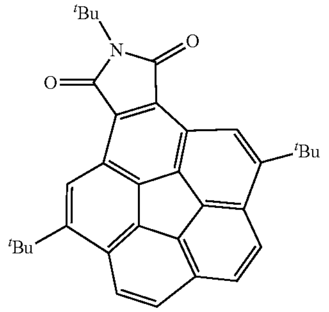
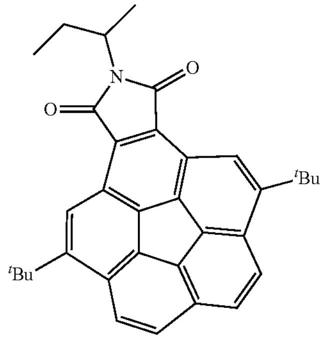
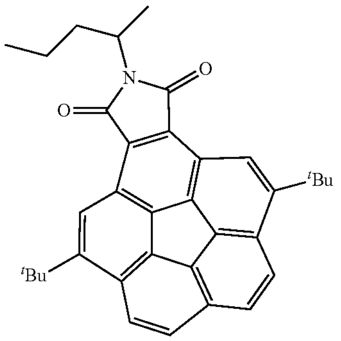
-continued
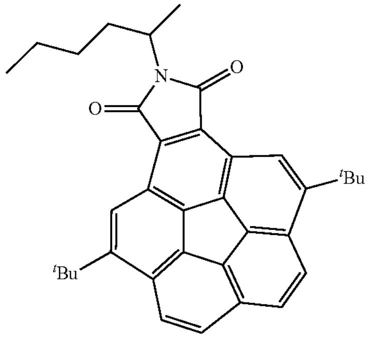
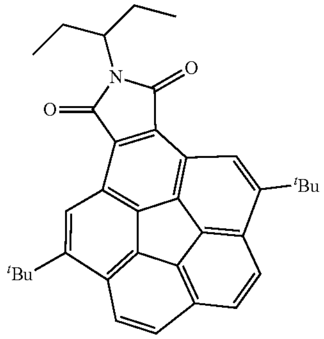
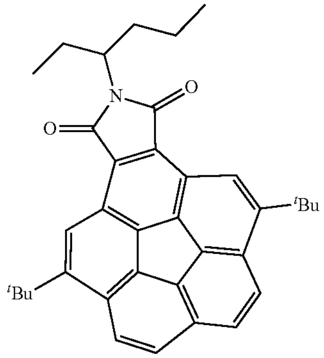
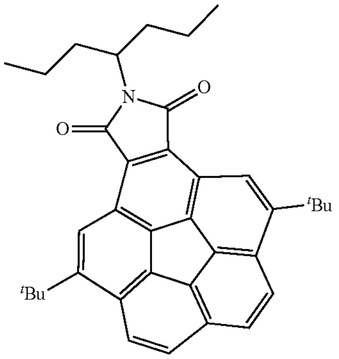
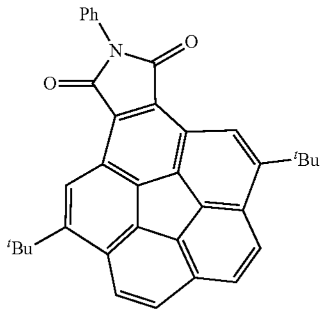

-continued
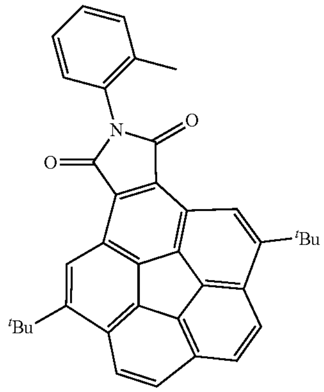
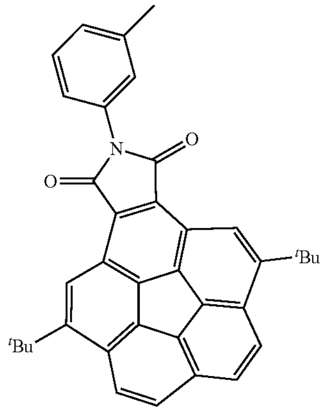
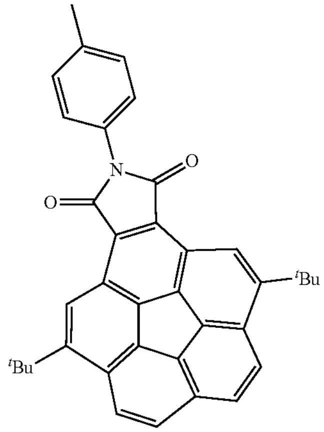
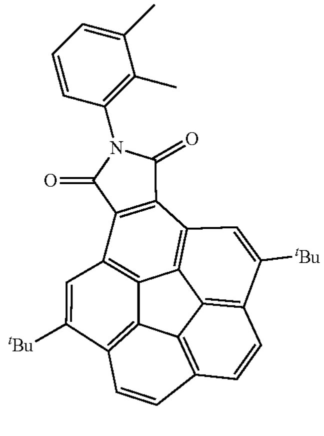
-continued
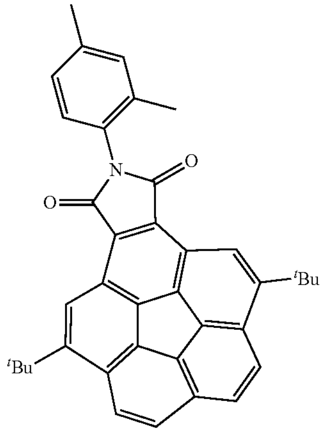
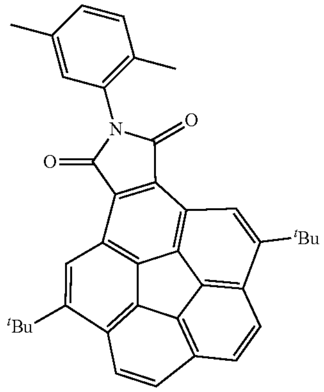
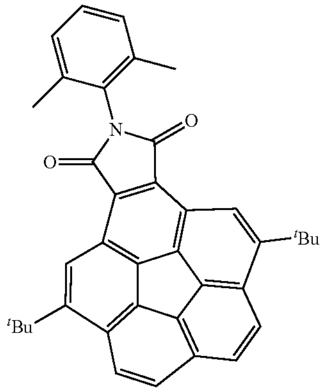
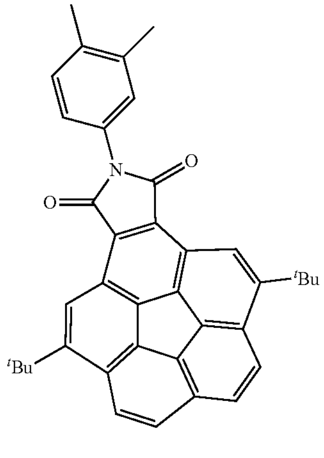

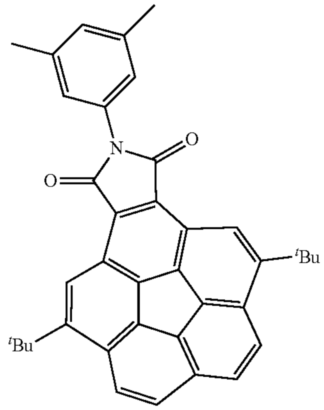
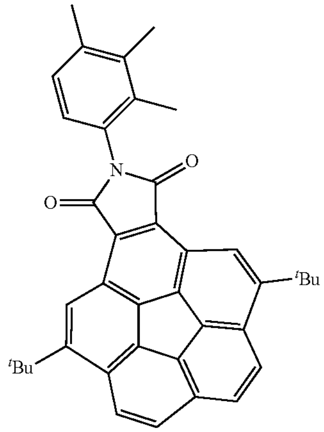
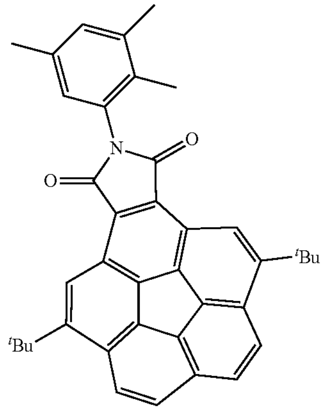
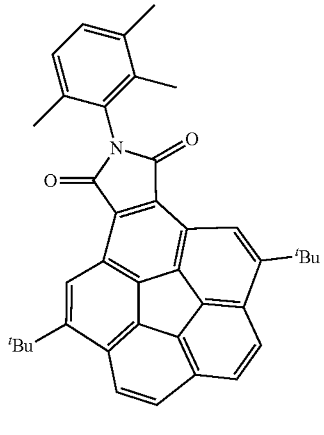
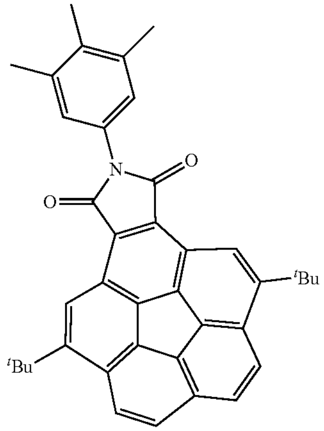
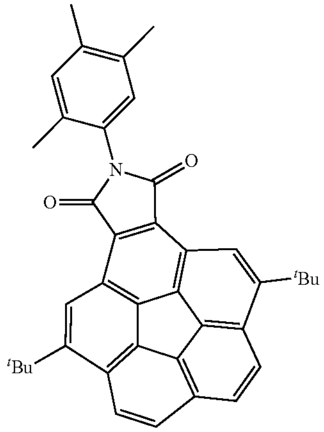
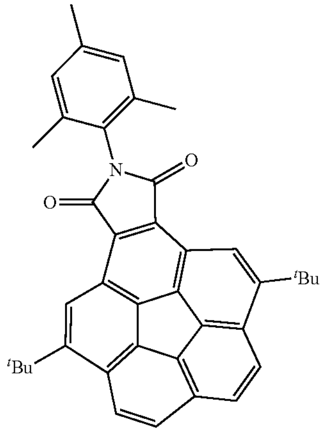
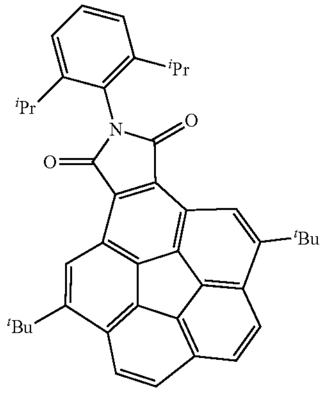

-continued
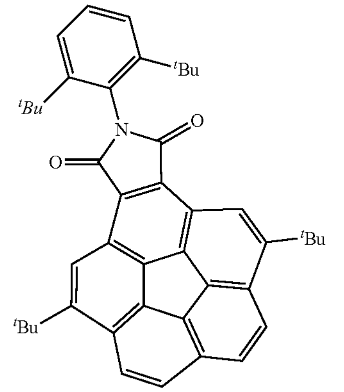
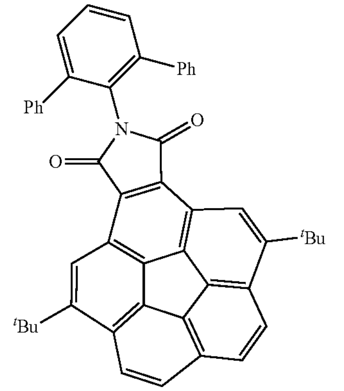
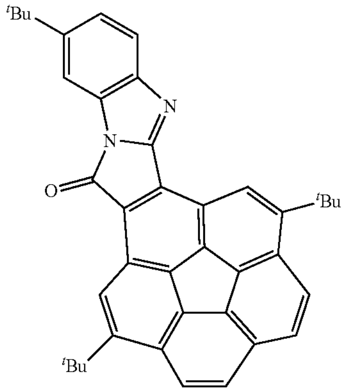
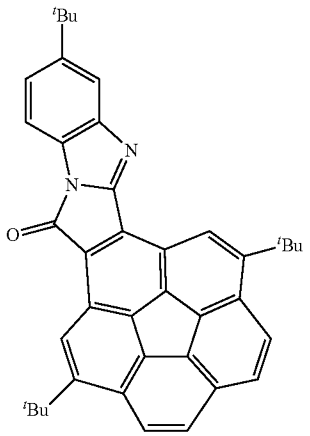
-continued
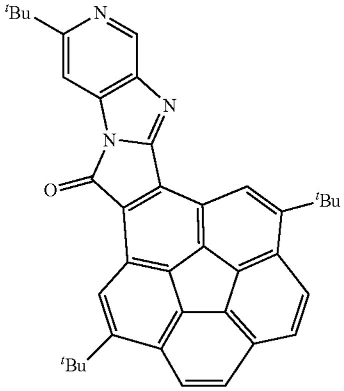
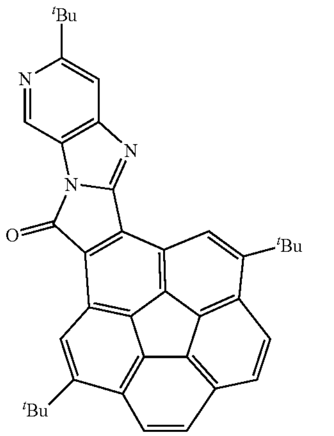
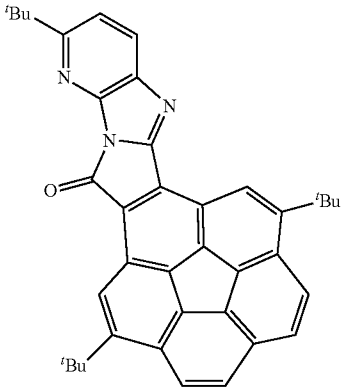
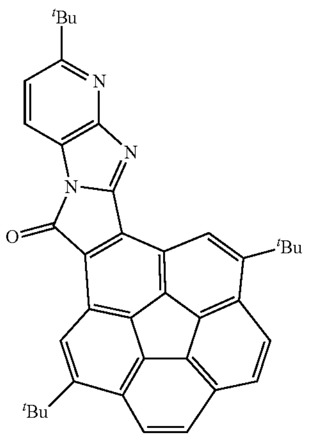

-continued
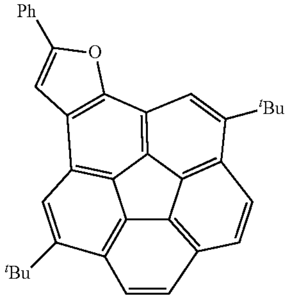
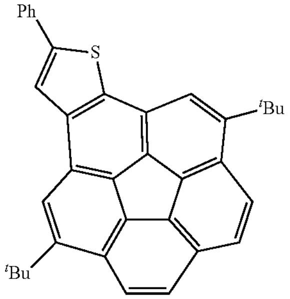
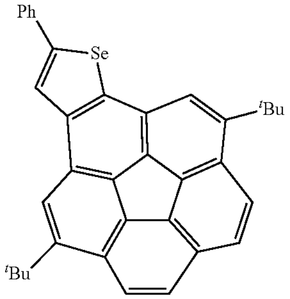
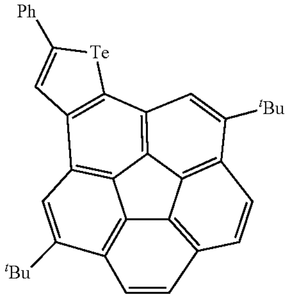
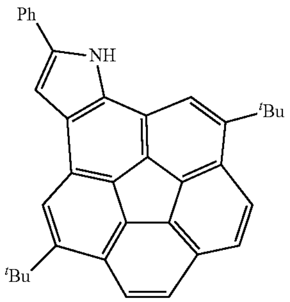
-continued
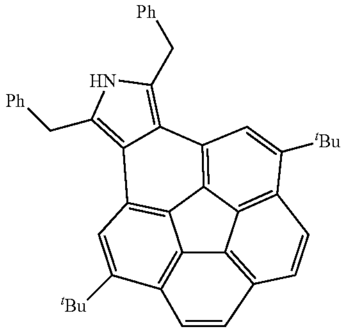
[Group 3]
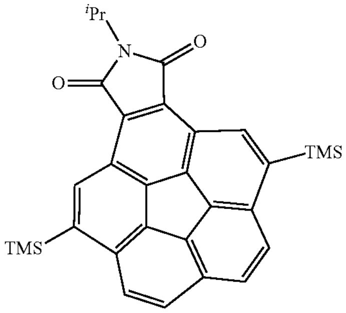
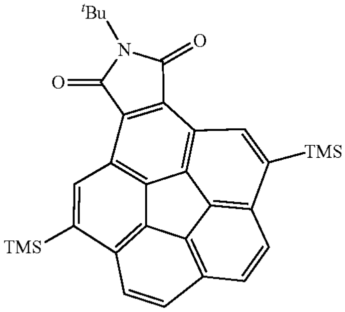
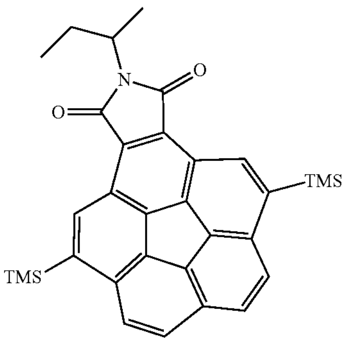

-continued
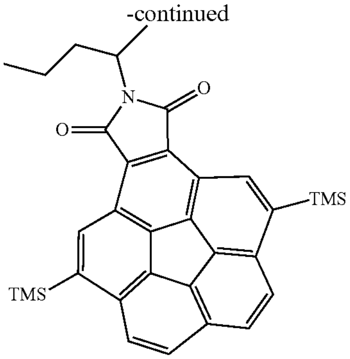
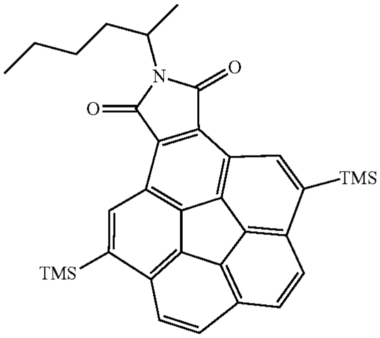
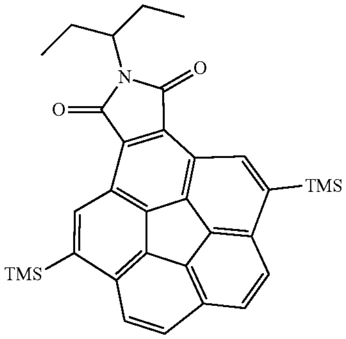
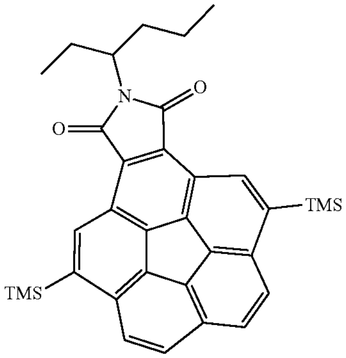
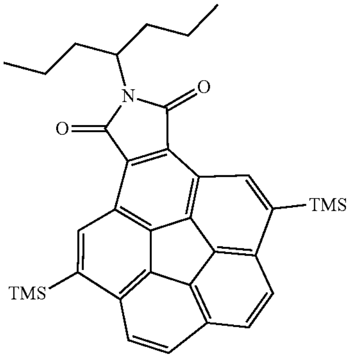
-continued
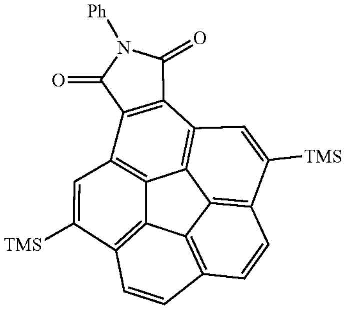
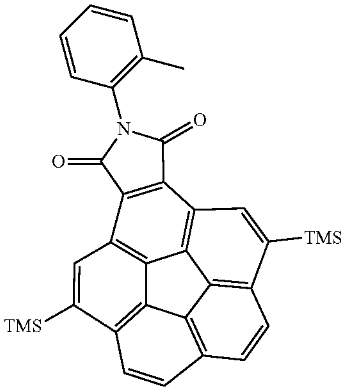
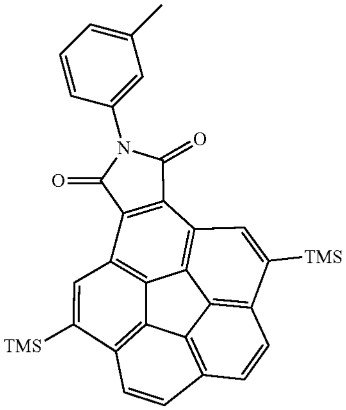
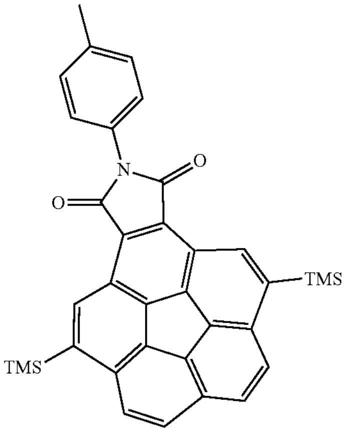

-continued
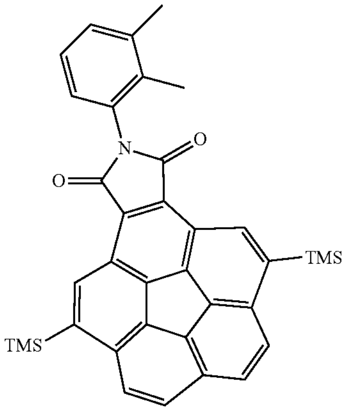
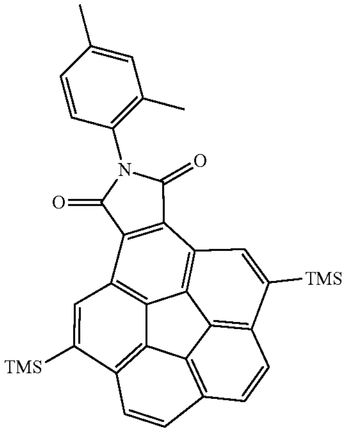
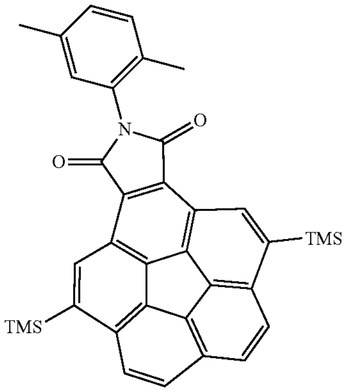
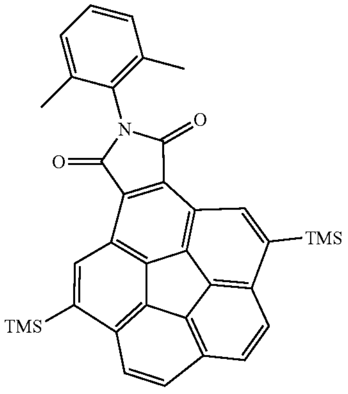
-continued
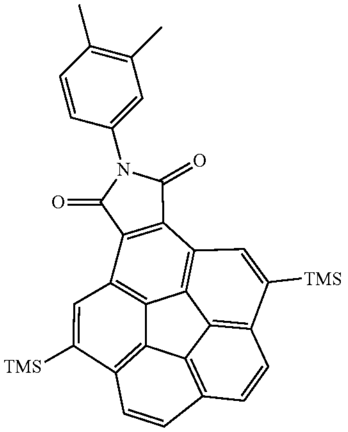
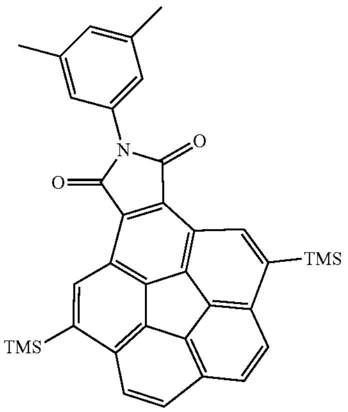
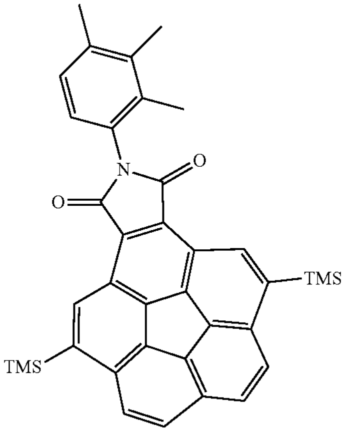
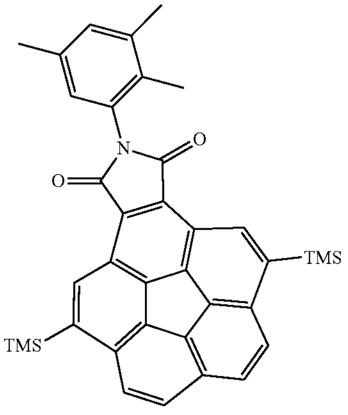

-continued
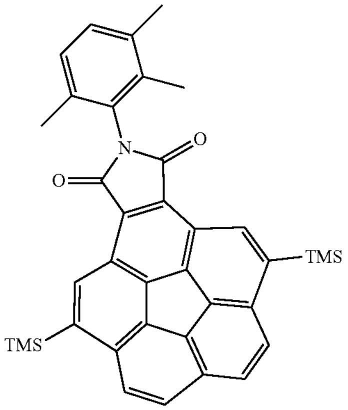
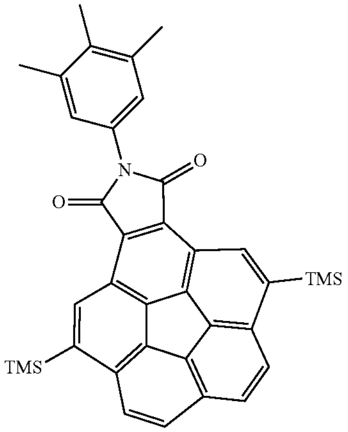
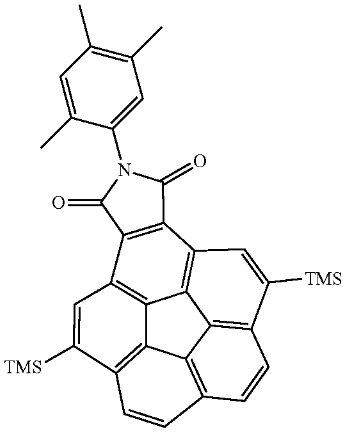
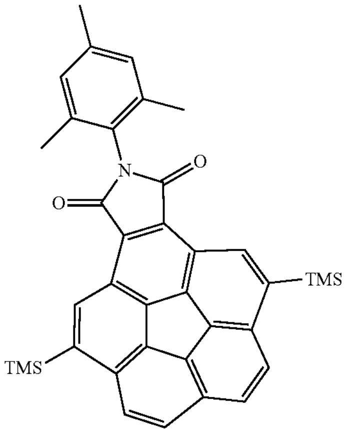
-continued
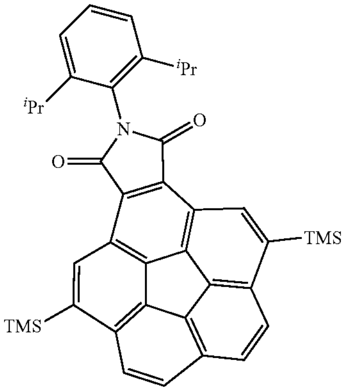
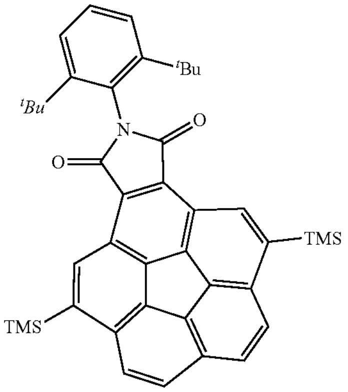
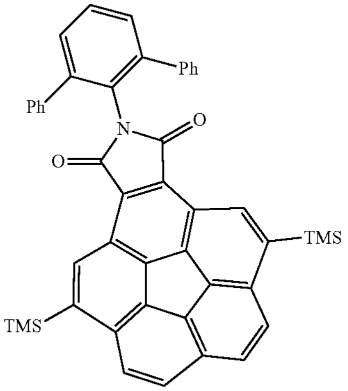
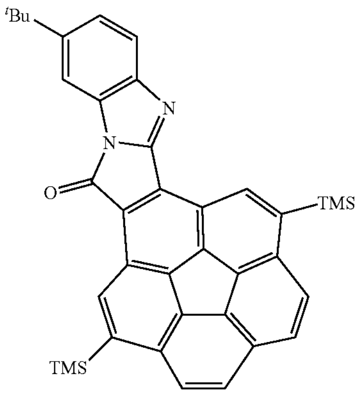

-continued
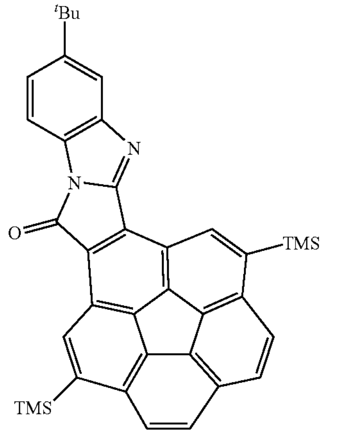
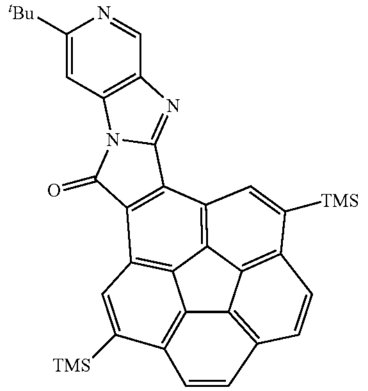
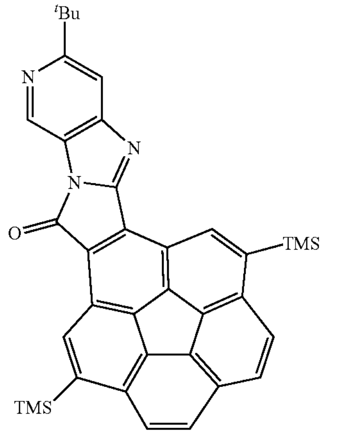
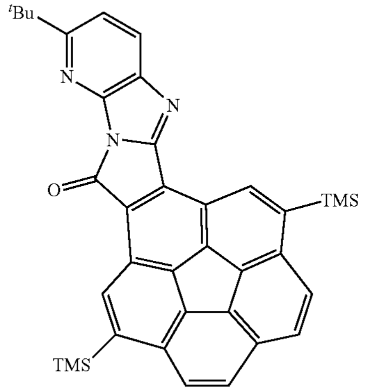
-continued
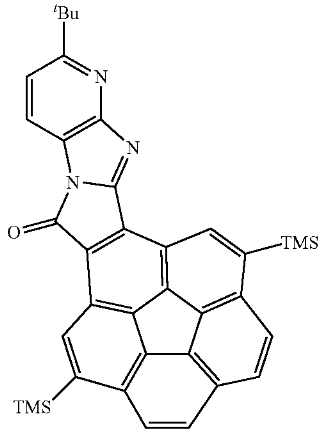
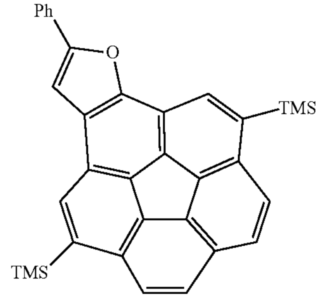
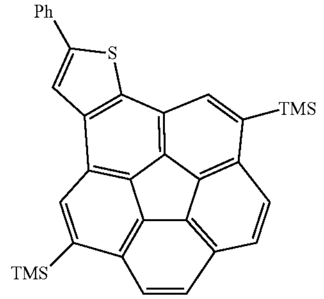
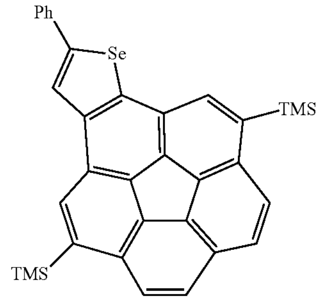
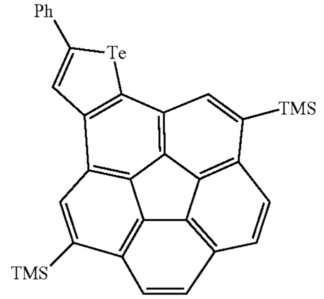

-continued
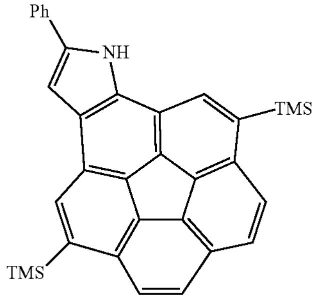
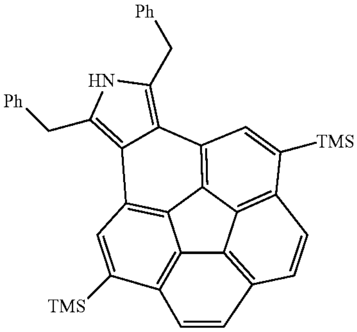
Group 4 illustrates structures which are substituted with a phenyl group instead of the two substituents (O$^t$Bu) groups of the corannulene of Group 1.
[Group 4]
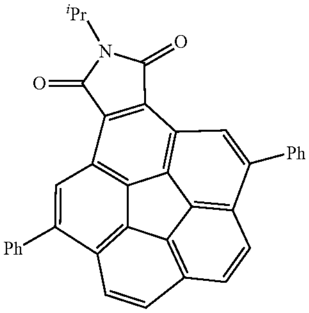
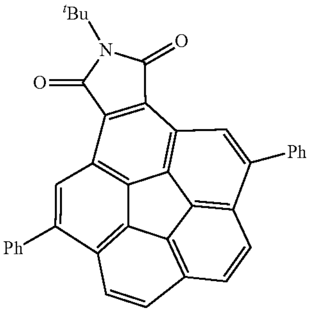
-continued
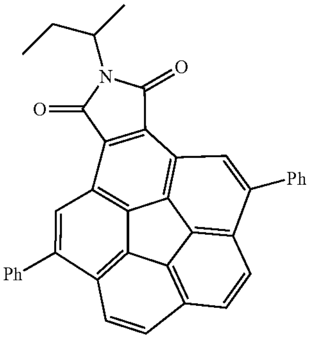
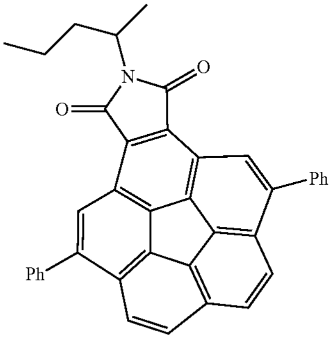
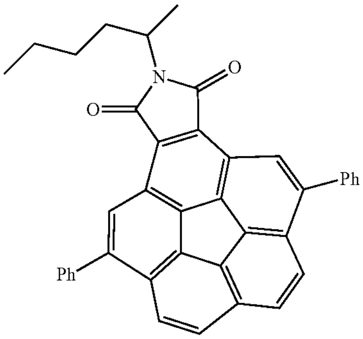
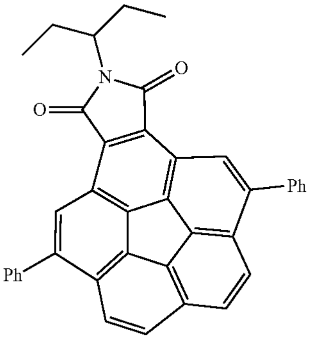
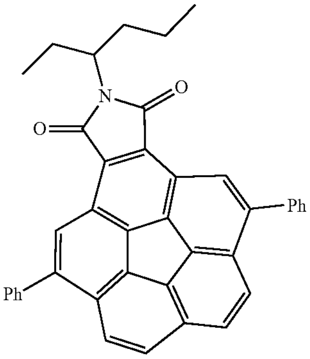

-continued
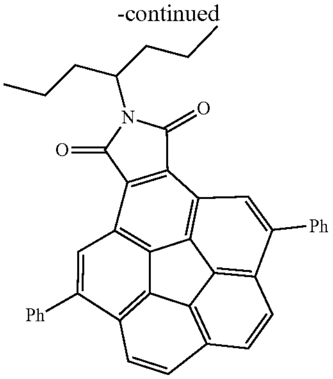
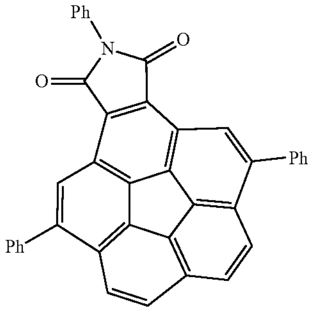
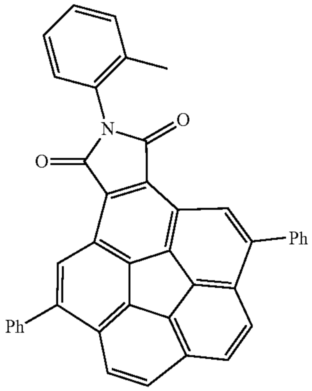
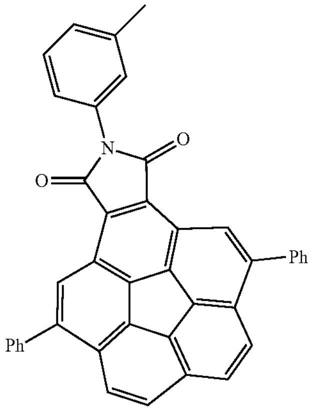
-continued
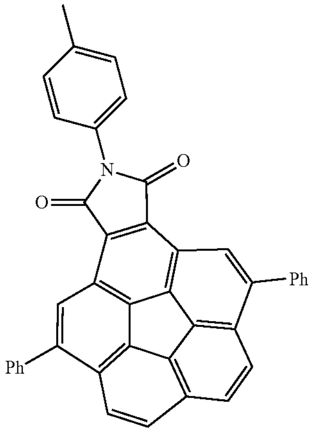
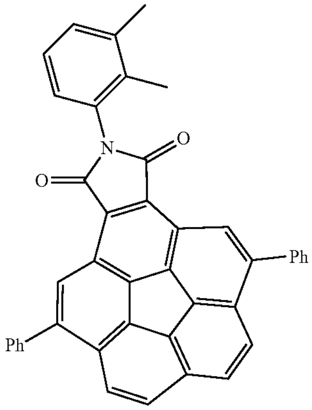
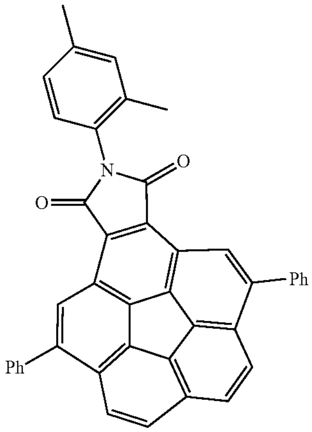
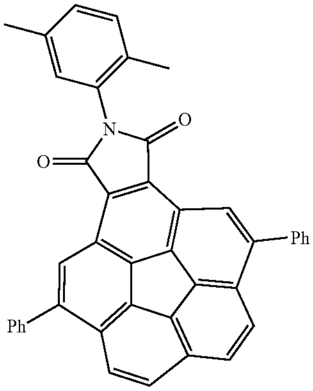

-continued
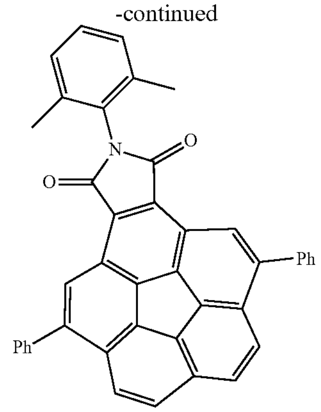
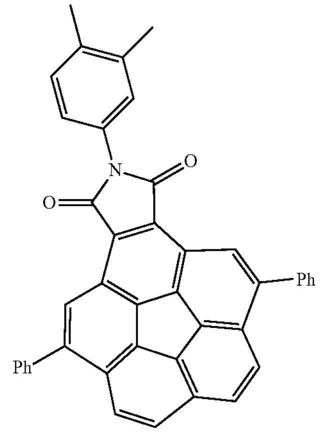
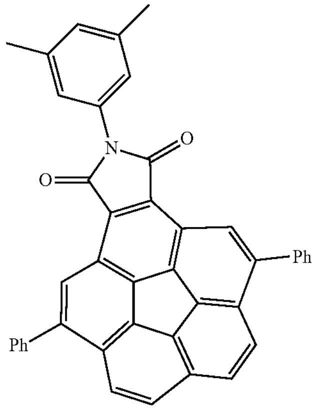
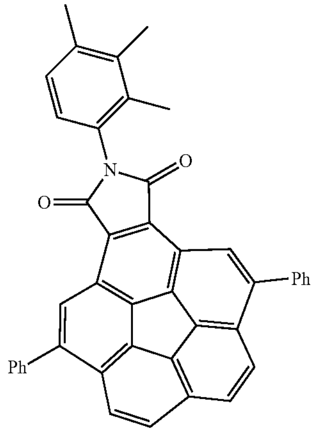
-continued
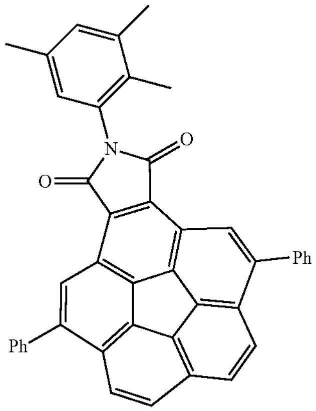
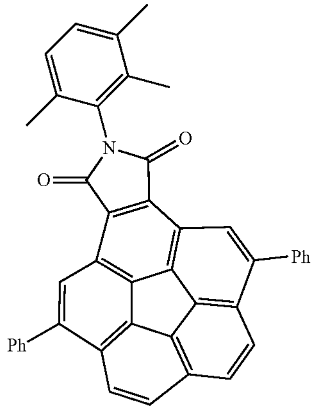
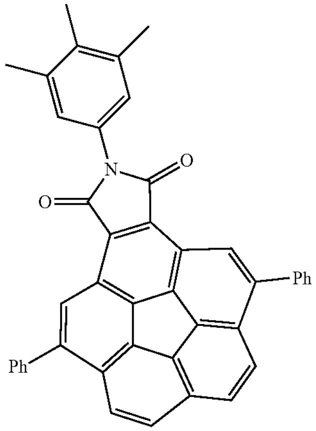
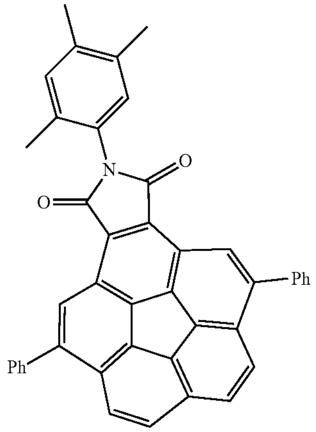

-continued
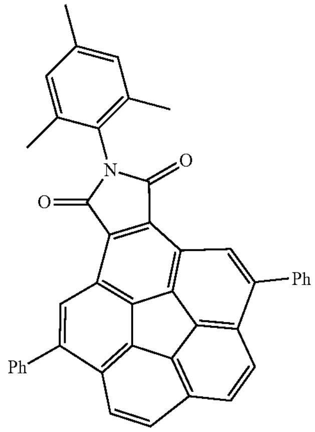
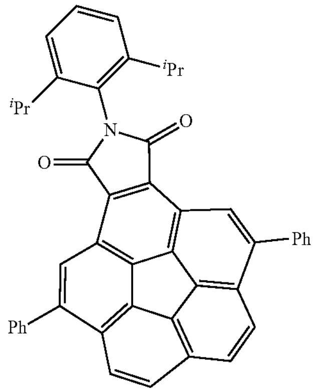
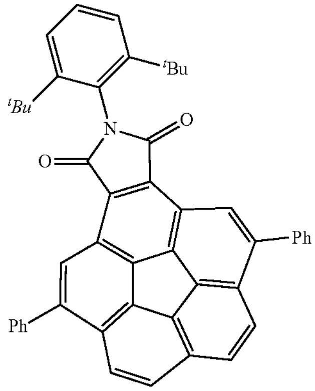
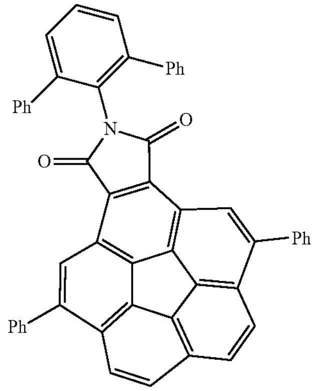
-continued
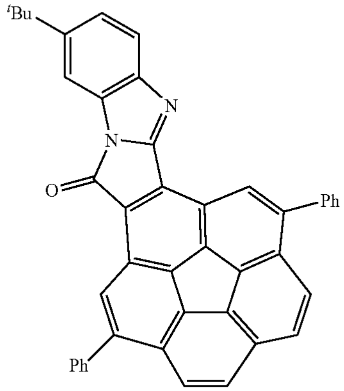
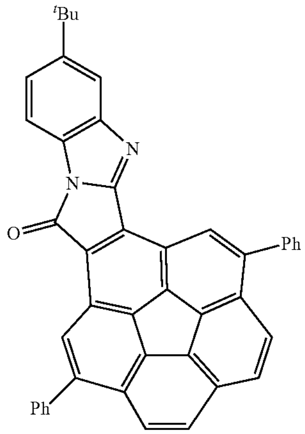
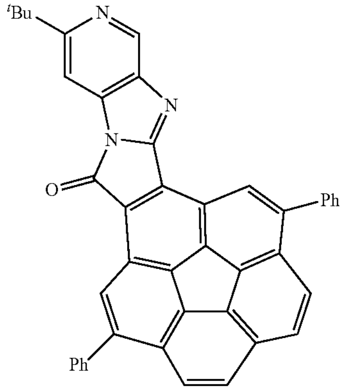
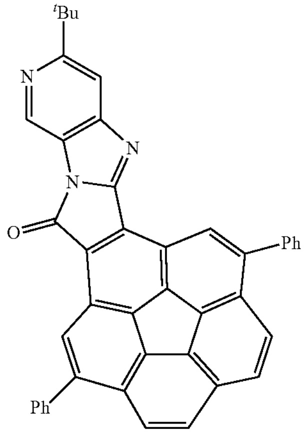

-continued

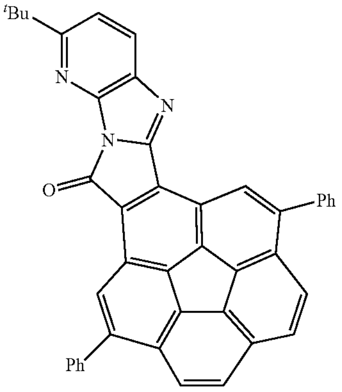

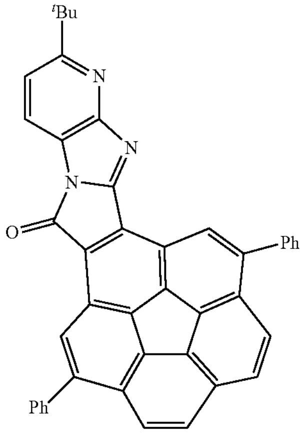

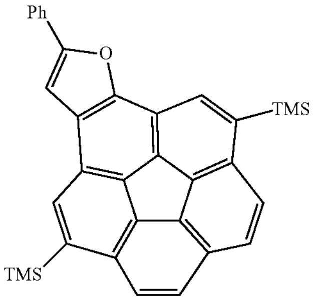

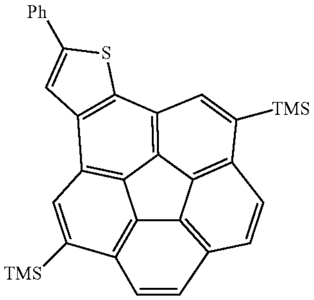

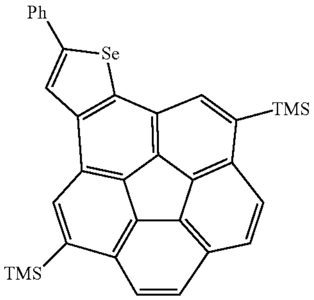

-continued

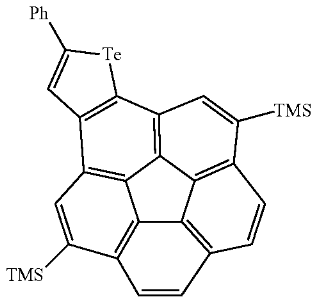

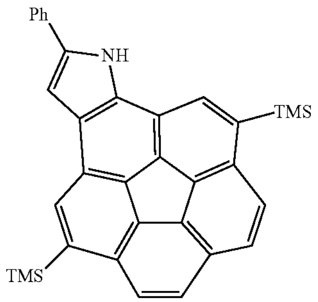

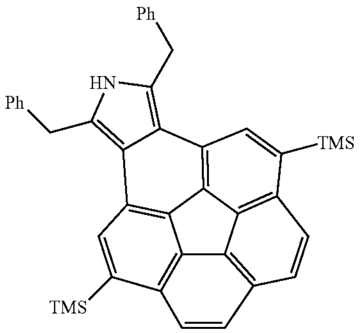

In Group 4, two phenyl (Ph) groups which are substituents of corannulene are substituted with at least one substituent selected from a C1 to C20 linear alkyl group, a C3 to C20 branched alkyl group, a C6 to C12 aryl group, and a C3 to C12 heteroaryl group. These substituents may be present in plural, in which case they may be the same or different from one another. The positions of the substituents may be at an ortho, meta, or para position. For example, structures which substituted with an isopropyl group or t-butyl group at an ortho position are shown in Group 5.

[Group 5]

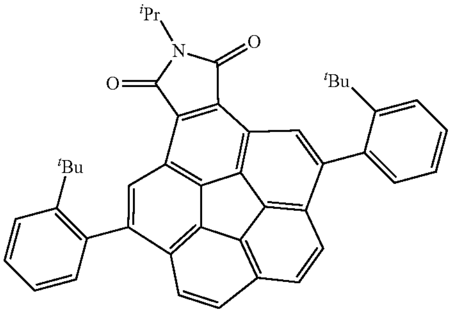

-continued
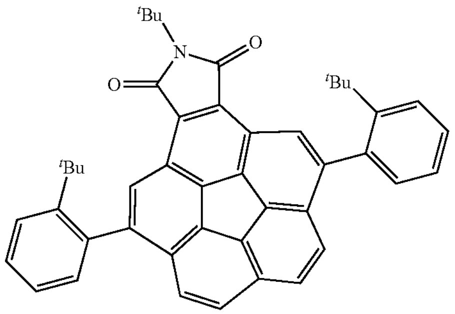
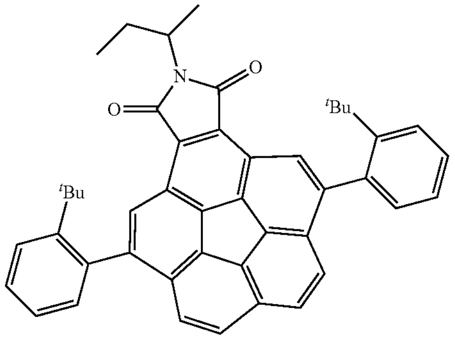
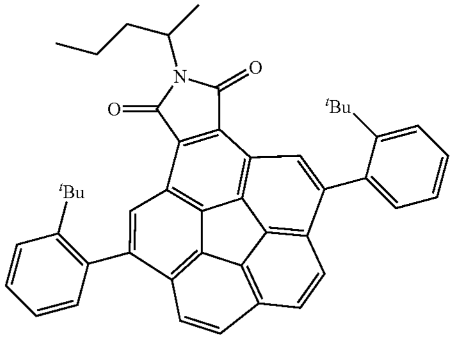
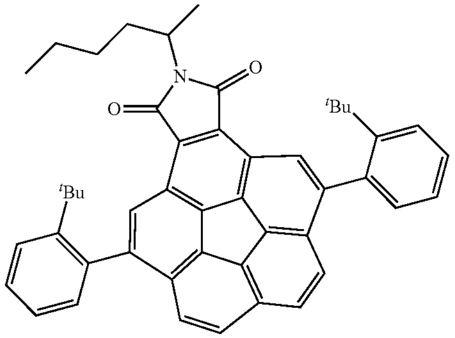
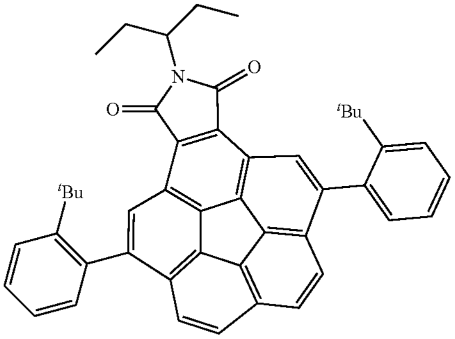
-continued
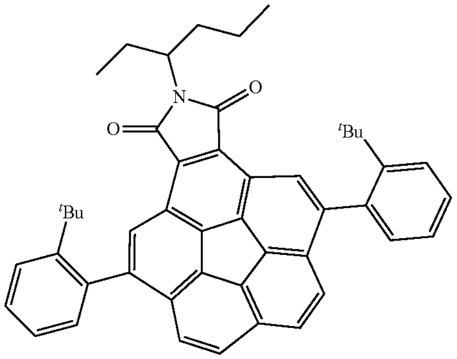
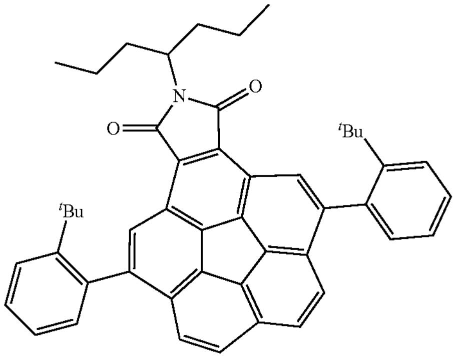
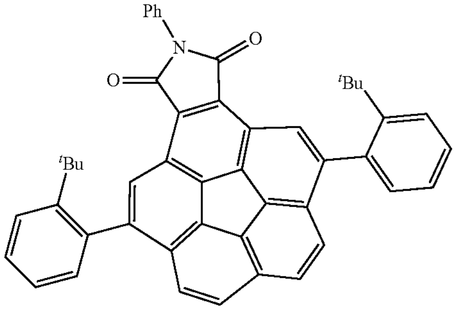
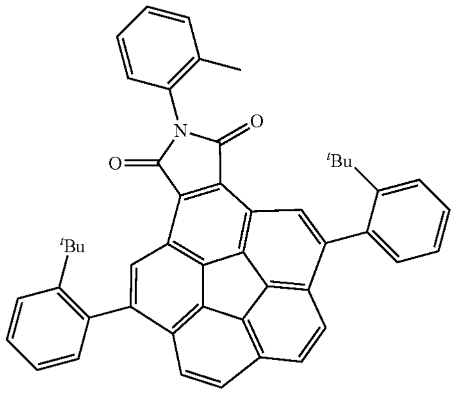

-continued
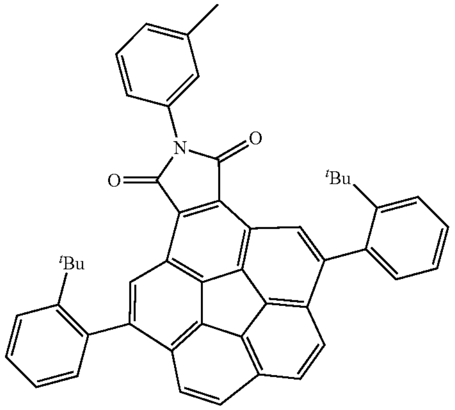
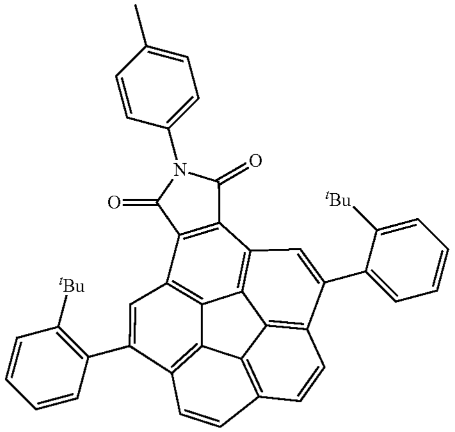
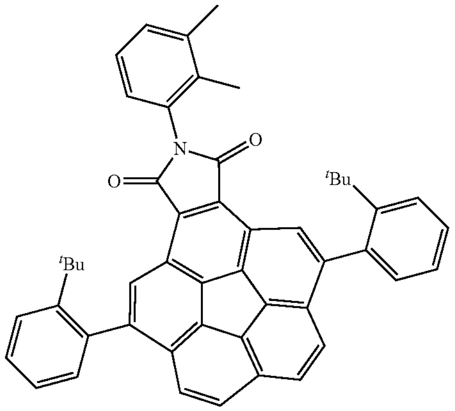
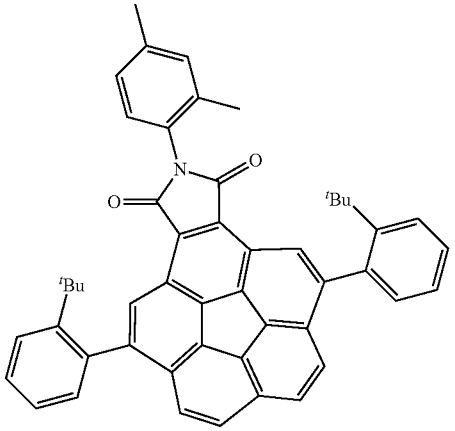
-continued
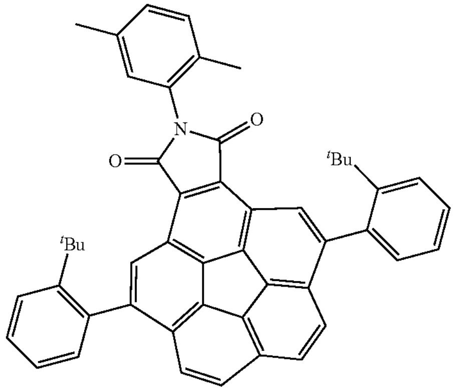
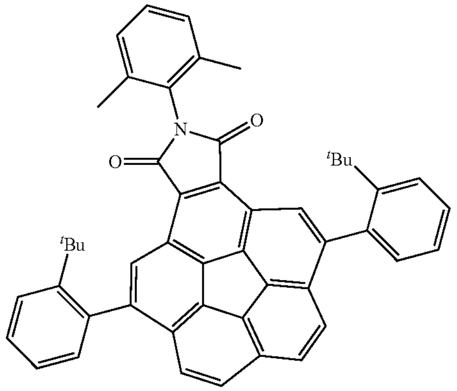
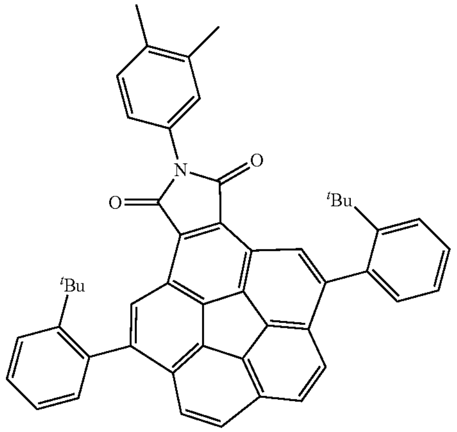
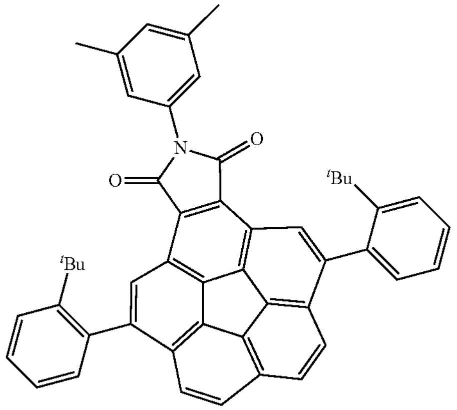

-continued
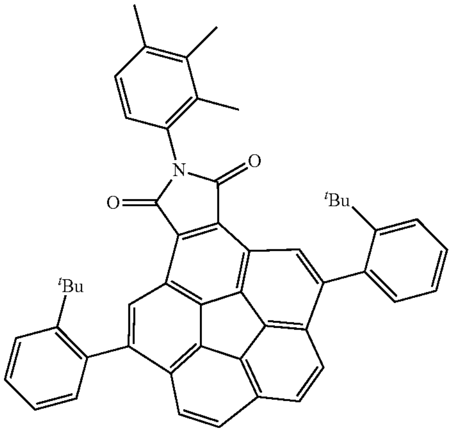
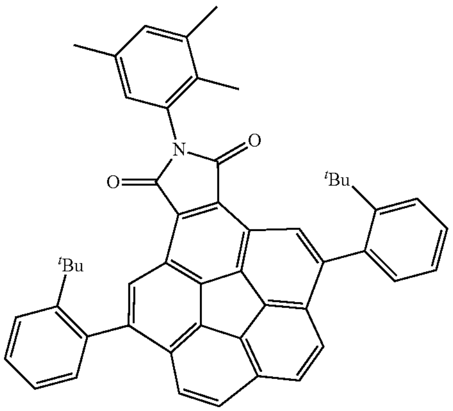
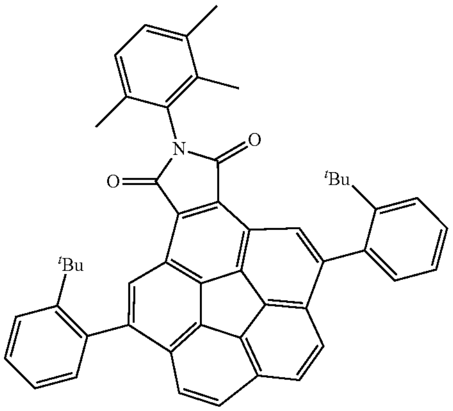
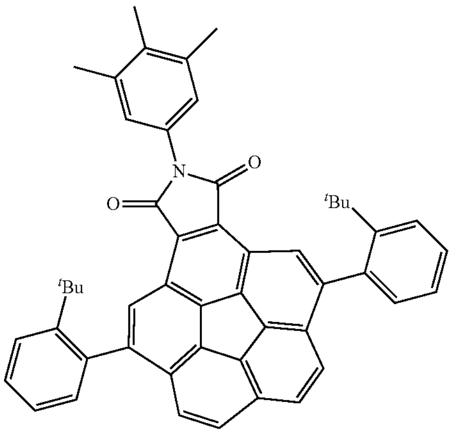
-continued
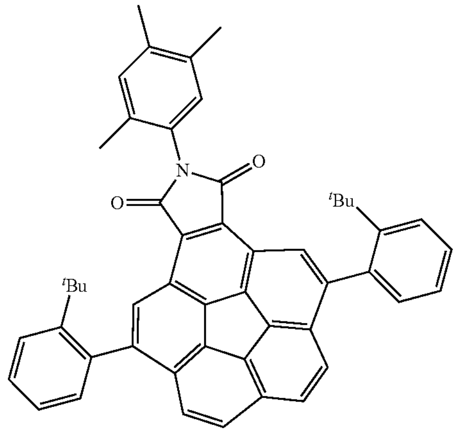
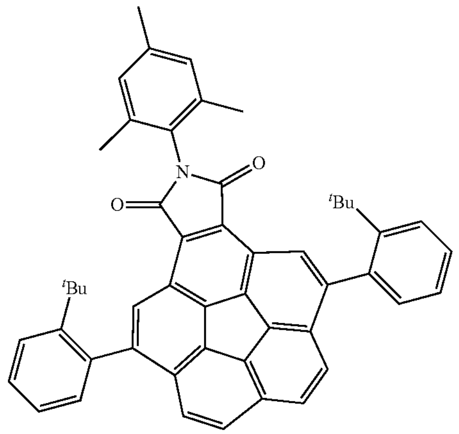
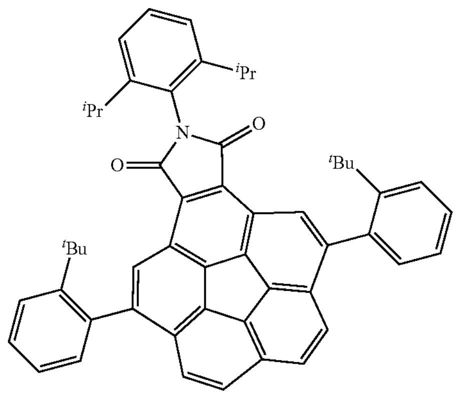
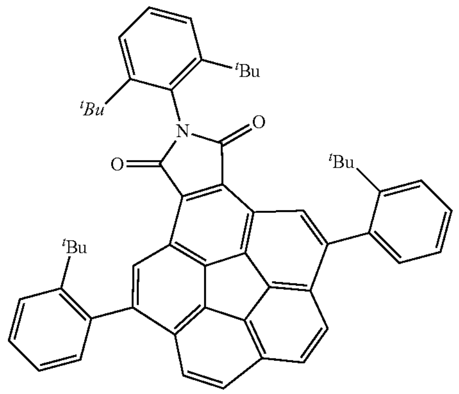

-continued
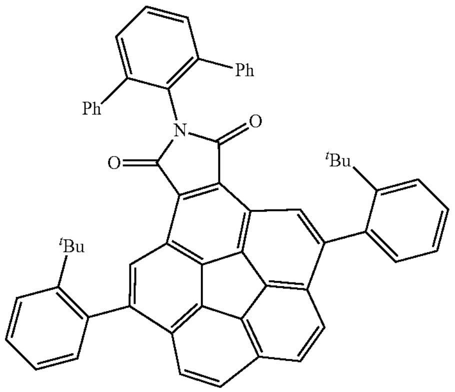
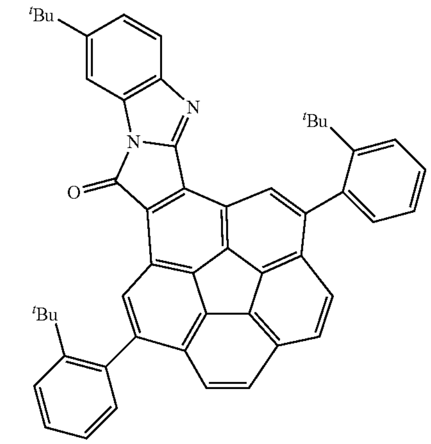
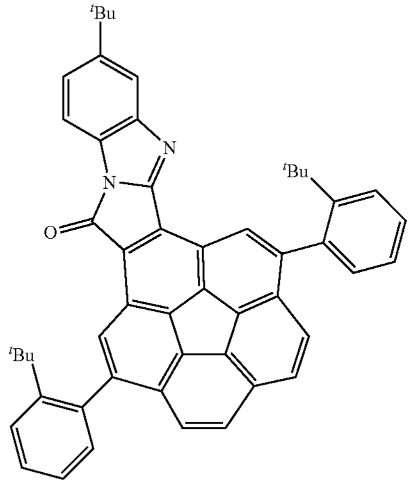
-continued
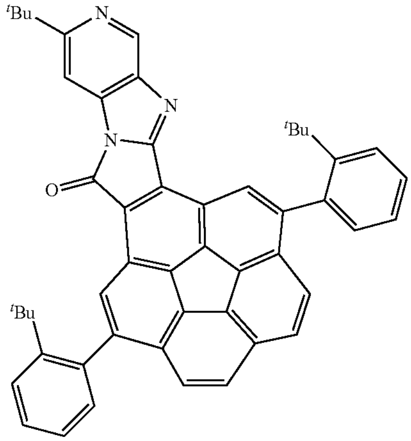
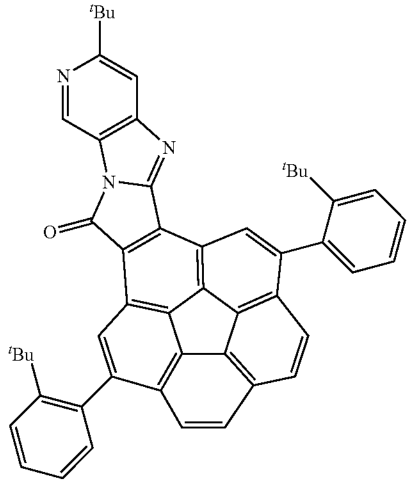
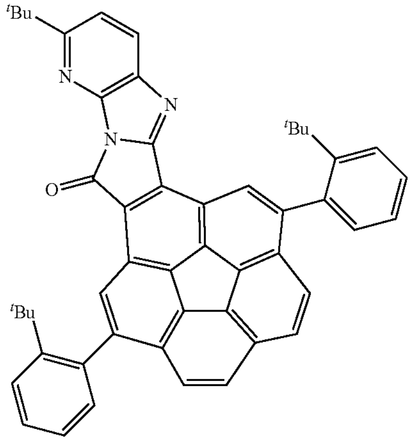

-continued

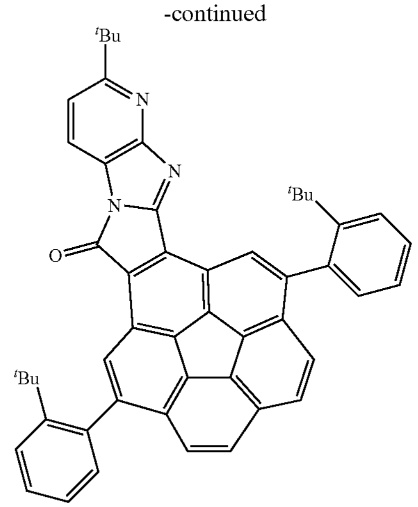

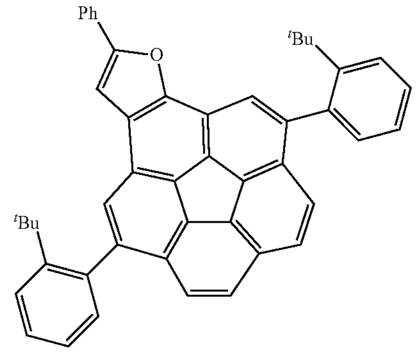

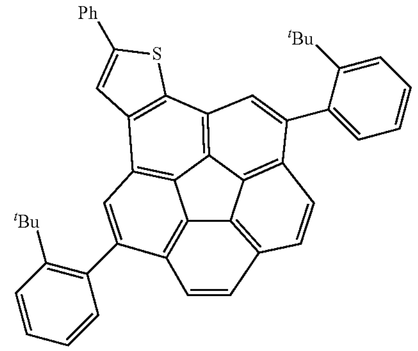

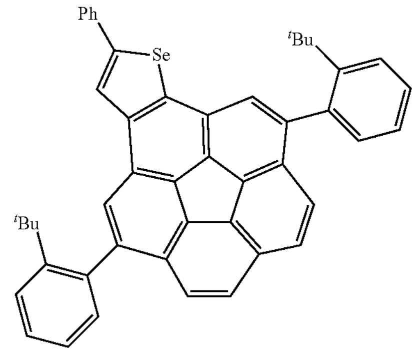

-continued

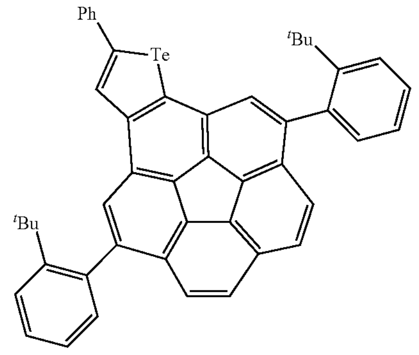

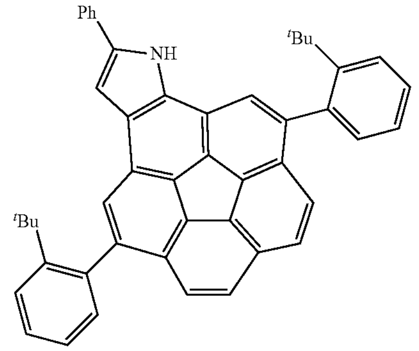

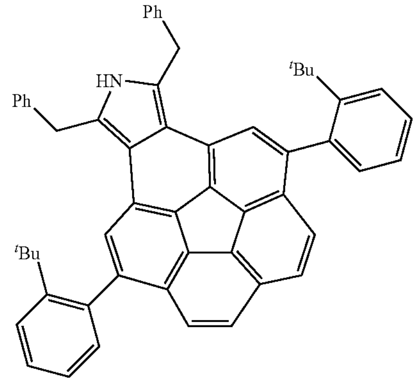

The corannulene of Group 1 may be substituted with a substituted or unsubstituted C2 to C30 heteroaryl group (for example, pyridyl group, pyrimidyl group, triazinyl group, thienyl group, etc.) instead of the two substituents (O$^t$Bu). The position of the heteroatom (for example, nitrogen, sulfur, etc.) of the substituted or unsubstituted C2 to C30 heteroaryl group may be present at the ortho, meta, or para position with respect to the bonding position. The heteroaryl group may be substituted with at least one substituent selected from a C1 to C20 linear alkyl group, a C3 to C20 branched alkyl group, a C6 to C12 aryl group, and a C3 to C12 heteroaryl group.

Group 6 exemplifies a structure which substituted with a pyridyl group as the heteroaryl group and Group 7 exemplifies structure which substituted with a thienyl group, a furanyl group, a pyrrolyl group, a selenophenyl group, or a tellurophenyl group as the heteroaryl group.

[Group 6]
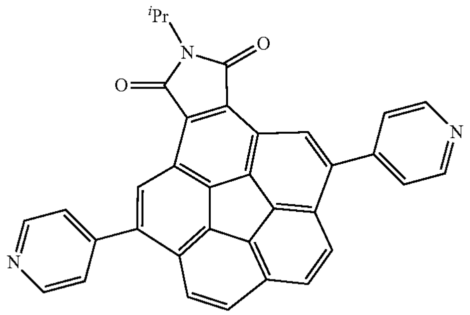
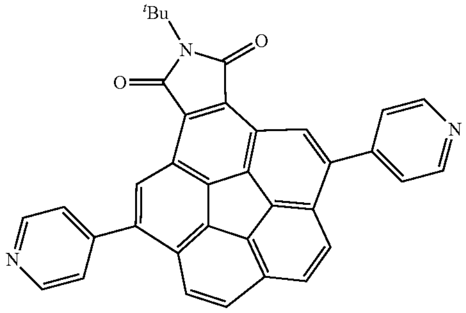
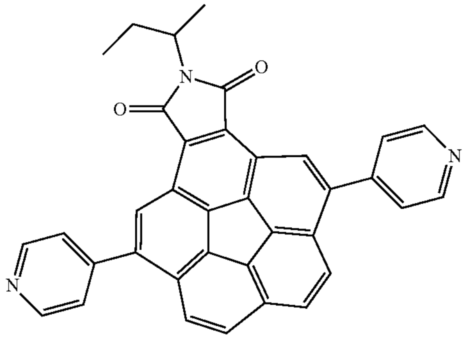
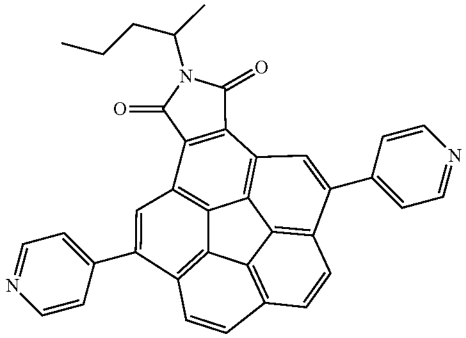
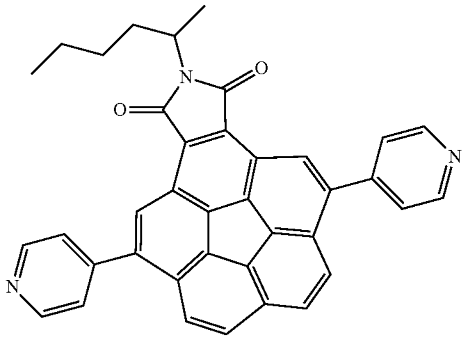
-continued
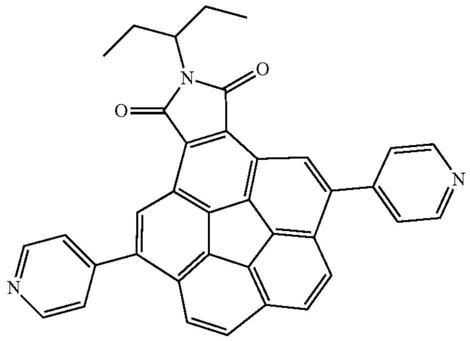
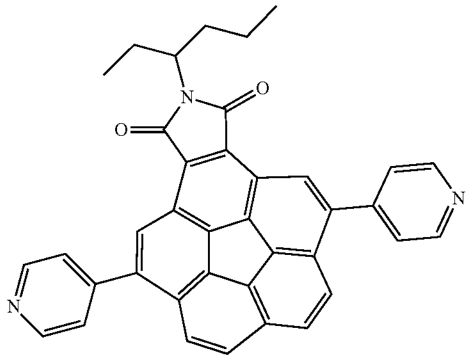
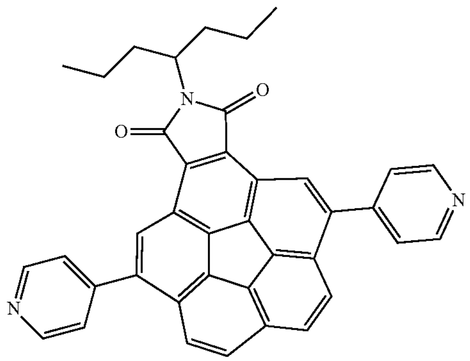
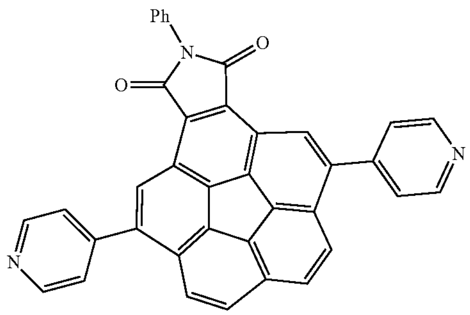

-continued
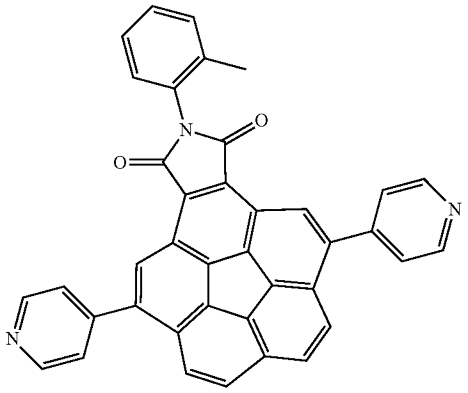
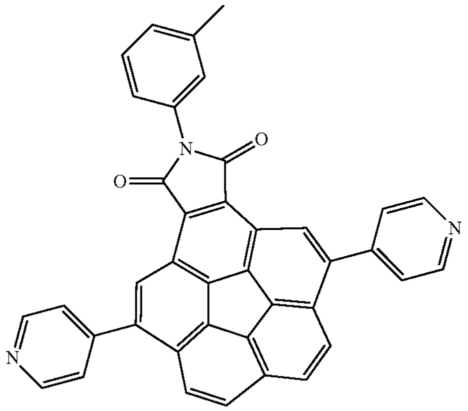
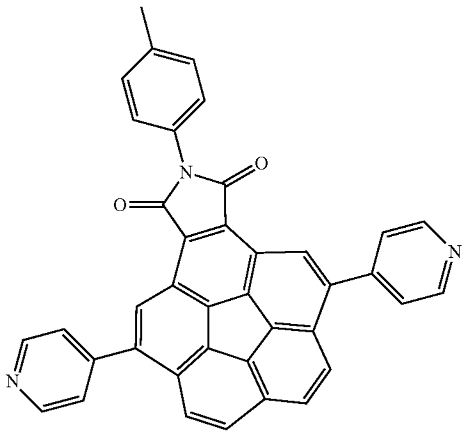
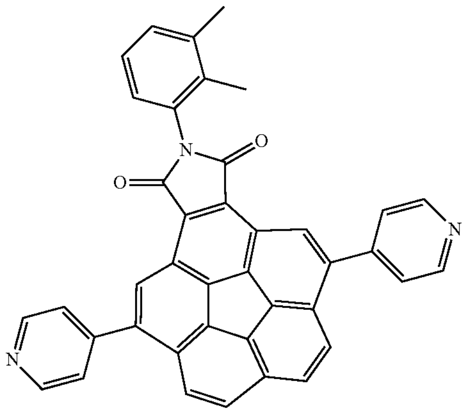
-continued
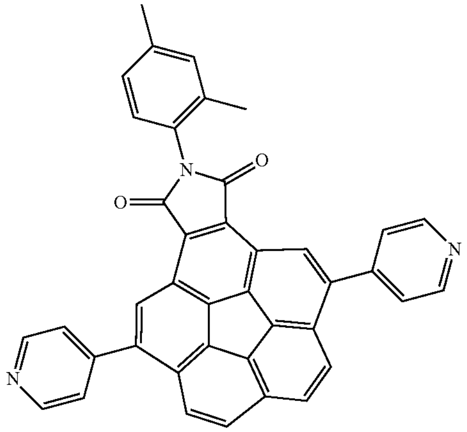
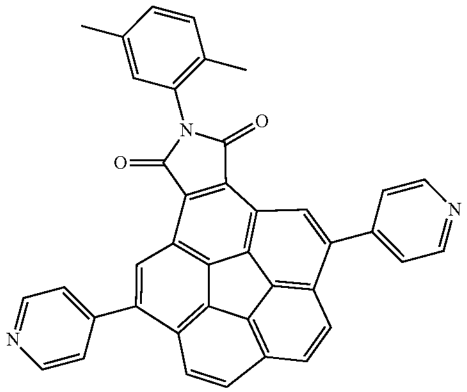
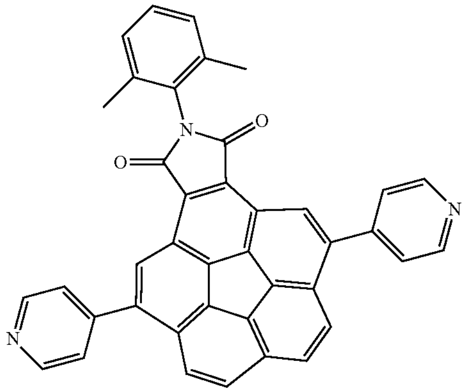
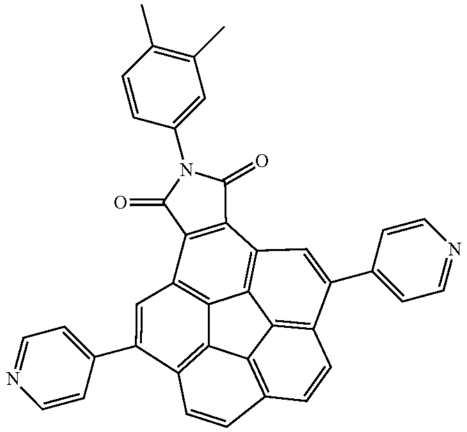

-continued
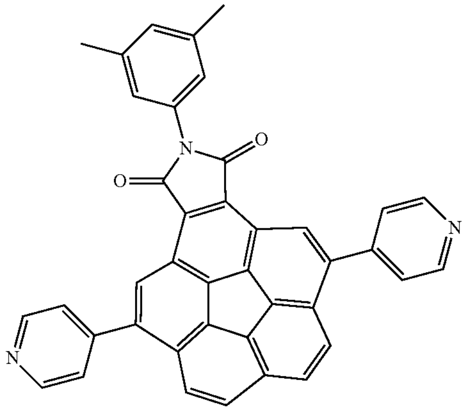
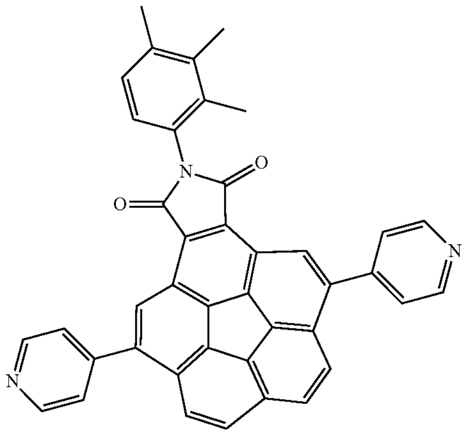
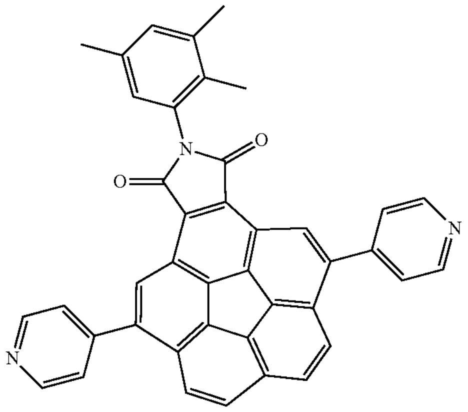
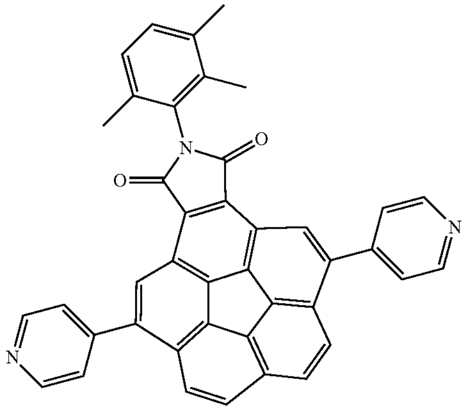
-continued
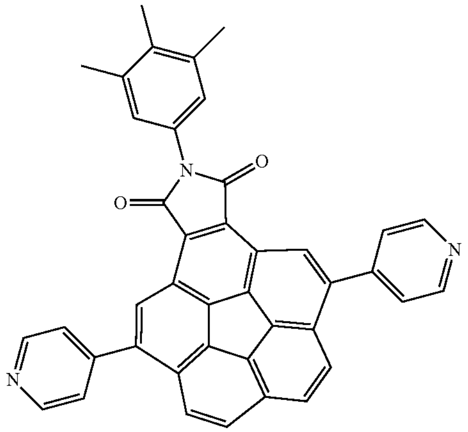
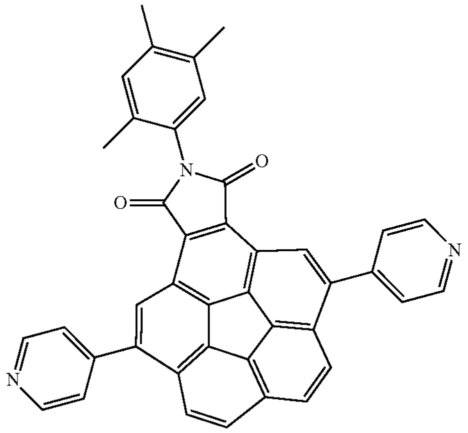
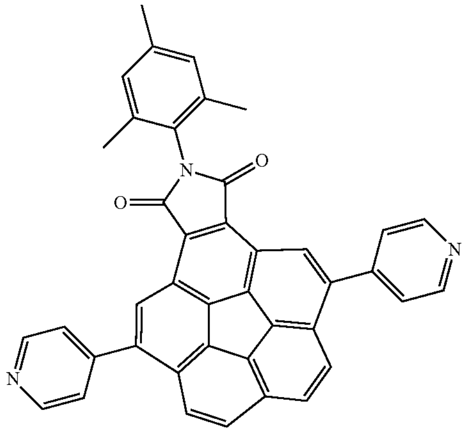
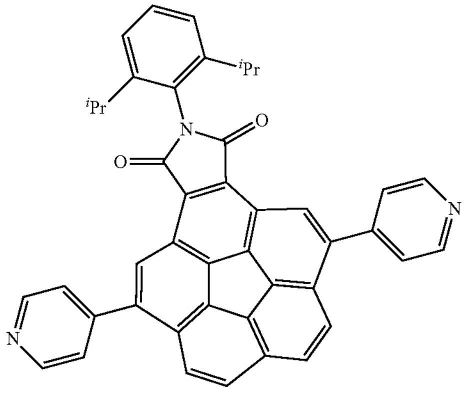

-continued
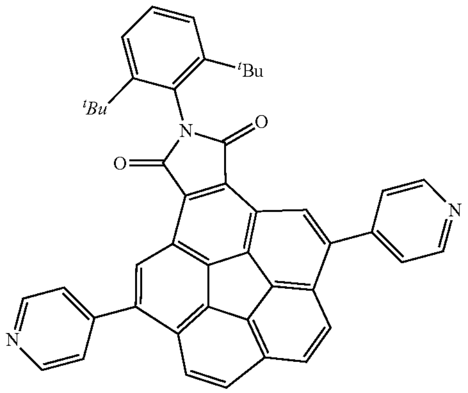
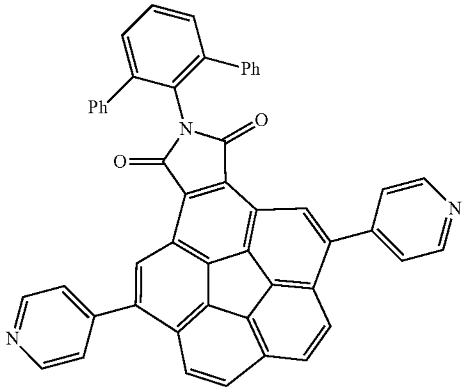
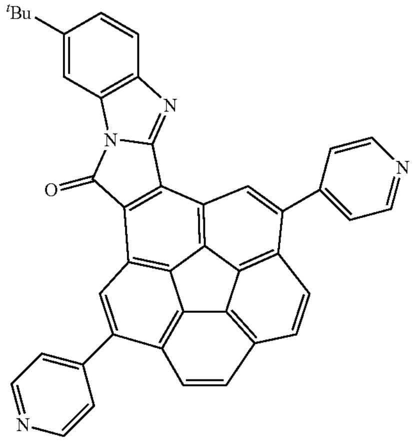
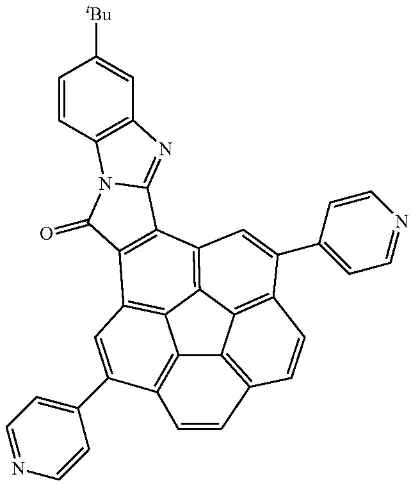
-continued
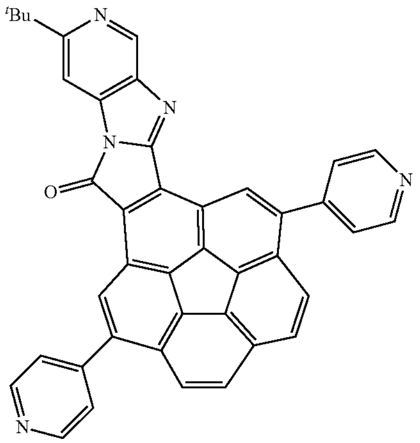
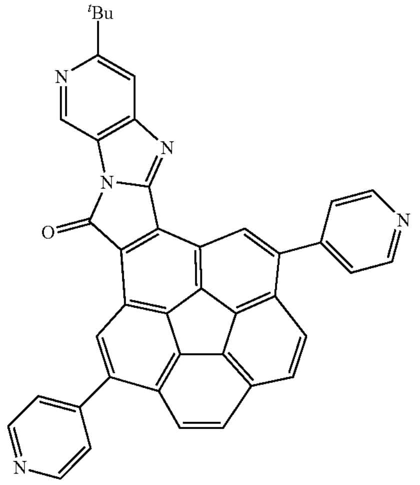
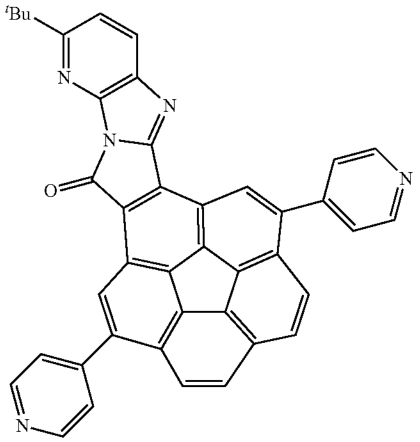

-continued
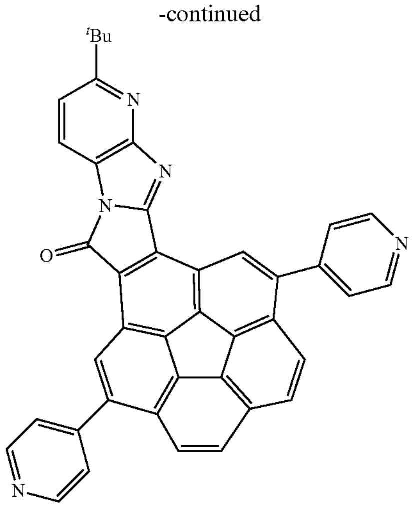
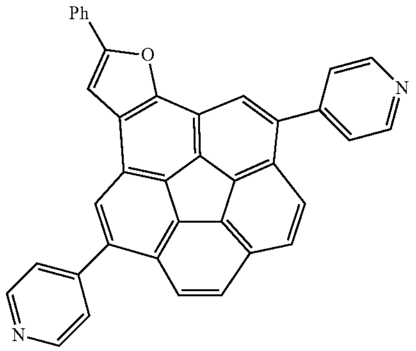
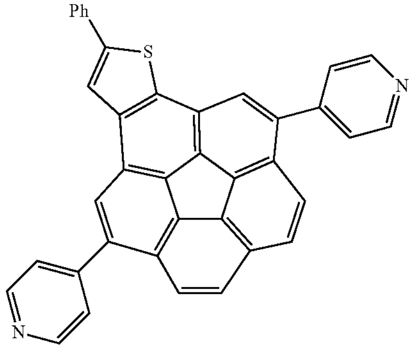
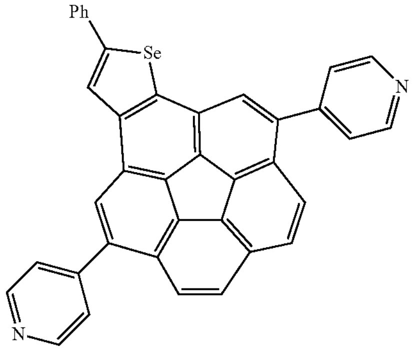
-continued
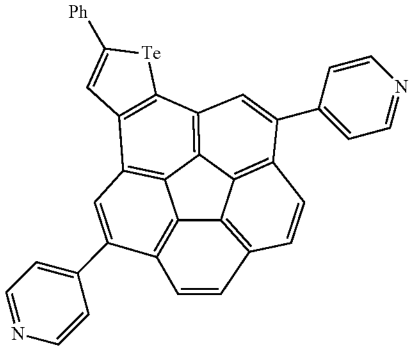
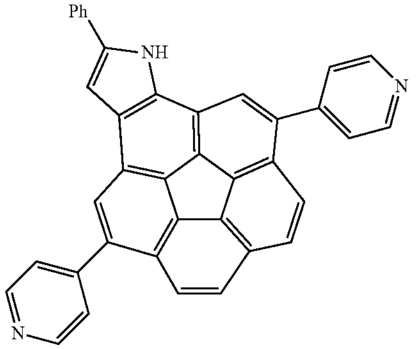
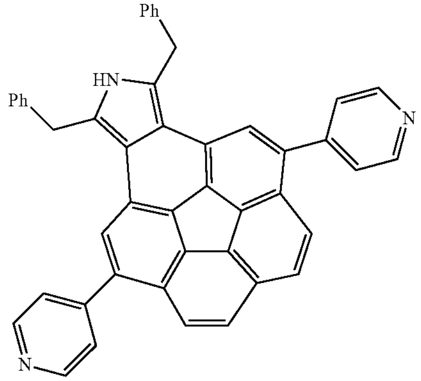
In Group 6, the pyridyl group may be substituted with at least one substituent selected from a C1 to C20 linear alkyl group, a C3 to C20 branched alkyl groups, a C6 to C12 aryl group, and a C3 to C12 heteroaryl group.
[Group 7]
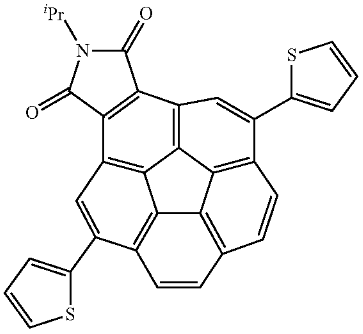

-continued

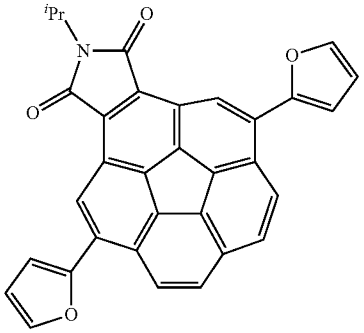

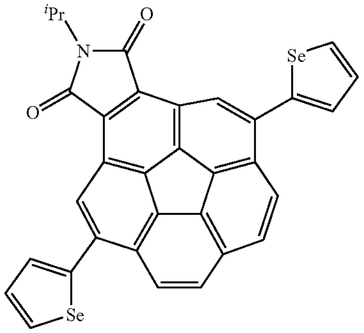

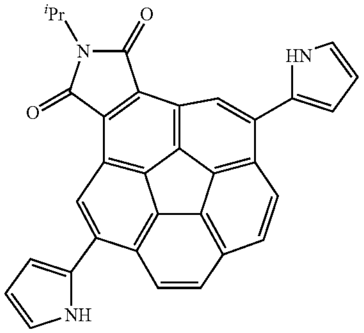

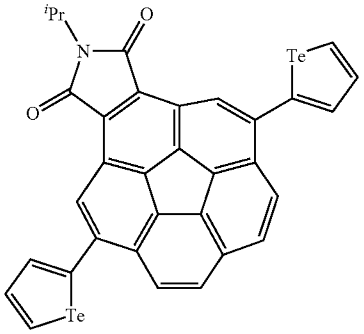

In Group 7, the thienyl group, furanyl group, pyrroyl group, selenophenyl group, or tellurophenyl group may be substituted with at least one substituent selected from a C1 to C20 linear alkyl group, a C3 to C20 branched alkyl group, a C6 to C12 aryl group, and a C3 to C12 heteroaryl group. In addition, the hydrogen of the pyrrolyl group may be substituted with at least one substituent selected from a C1 to C20 linear alkyl group, a C3 to C20 branched alkyl group, a C6 to C12 aryl group, and a C3 to C12 heteroaryl group.

The phenyl (Ph) group of Group 5 or the pyridyl group of Group 6 may be fused to corannulene through an alicyclic hydrocarbon group such as cyclopentadiene. These structures are illustrated in Group 8.

[Group 8]

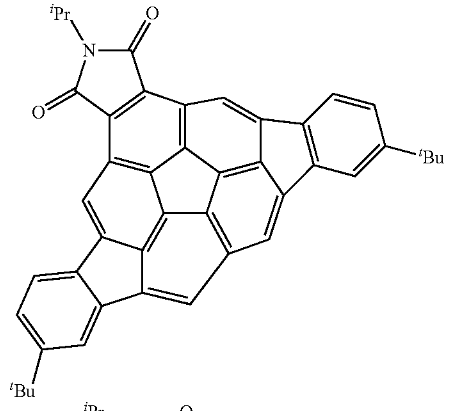

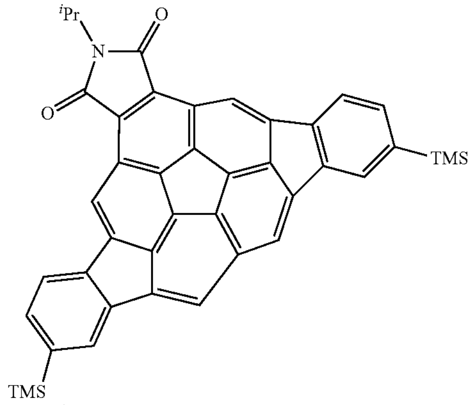

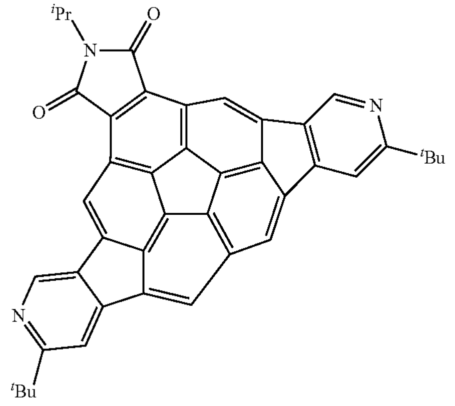

The fullerene subunit derivative (N-type semiconductor) may have an average distance from the P-type semiconductor of less than or equal to about 6.0 Å, for example, less than or equal to about 5.5 Å, or less than or equal to about 5.0 Å. The fullerene subunit derivative may adjust the average distance from the P-type semiconductor within the above range by including a bulky substituent (X) and an additional bulky substituent on the side. When the average distance from the P-type semiconductor is maintained within the above range, the fullerene subunit derivative (N-type semiconductor) and the P-type semiconductor may be well mixed to form a bulk hetero junction (BHJ).

The fullerene subunit derivative may be included in an amount of greater than or equal to about 50 parts by volume, for example, greater than or equal to about 60 parts by volume, or greater than or equal to about 70 parts by volume and less than or equal to about 150 parts by volume, for example, less than or equal to about 140 parts by volume, or less than or equal to about 130 parts by volume based on 100 parts by volume of the fullerene or a fullerene derivative. Within the above range, the fullerene subunit derivative effectively suppresses aggregation of the fullerene or the fullerene derivative, thereby reducing unnecessary absorption in the blue region and increasing the absorption in the green region.

The fullerene subunit derivative may be formed into a thin film by vacuum deposition using sublimation together with the fullerene or the fullerene derivative. While maintaining the intrinsic properties of the fullerene or the fullerene derivative during the deposition process, it is possible to prevent optical properties from being deformed by aggregation of the fullerene or fullerene derivative generated during the film formation of the thin film. Thin film made of the N-type semiconductor composition including the fullerene or fullerene derivative and the fullerene subunit derivative may reduce abnormal absorption in a short wavelength region of visible light from about 400 nm to about 500 nm. For example, an absorption coefficient at a 450 nm wavelength of the thin film including the N-type semiconductor composition may be smaller than the absorption coefficient at a 450 nm wavelength of the thin film including unsubstituted fullerene (e.g., C60 fullerene). For example, the absorption coefficient at 450 nm of the thin film including the N-type semiconductor composition may be about 75% or less of the absorption coefficient at a 450 nm wavelength of the thin film including the unsubstituted fullerene (e.g., C60 fullerene).

Hereinafter, an organic photoelectric device including the aforementioned N-type semiconductor composition is described.

FIG. 1 is a cross-sectional view illustrating an organic photoelectric device according to an embodiment.

Referring to FIG. 1, an organic photoelectric device 100 according to an embodiment includes a first electrode 10 and a second electrode 20 facing each other and an organic layer 30 disposed between the first electrode 10 and the second electrode 20.

A substrate (not shown) may be disposed at the side of the first electrode 10 or the second electrode 20. The substrate may be for example made of an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 and the second electrode 20 is an anode and the other is a cathode. For example, the first electrode 10 may be a cathode and the second electrode 20 may be an anode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AITO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be alight receiving electrode disposed at a light receiving side.

The organic layer 30 may include an active layer.

The active layer is a layer including a P-type semiconductor and an N-type semiconductor to provide a pn junction, which is a layer producing excitons by receiving light from outside and then separating holes and electrons from the produced excitons.

Each of the P-type semiconductor and the N-type semiconductor may be a light absorbing material that absorbs at least a portion of the light in the visible region. For example, the P-type semiconductor may be a light absorbing material capable of selectively absorbing any one of a wavelength region of greater than or equal to about 400 nm to less than about 500 nm, a wavelength region of about 500 nm to about 600 nm, and/or a wavelength region of greater than about 600 nm and less than or equal to about 700 nm and the N-type semiconductor may be the aforementioned N-type semiconductor composition.

In one example, the P-type semiconductor selectively absorbs any one of light in a wavelength region of greater than or equal to about 400 nm to less than about 500 nm, a wavelength region of about 500 nm to about 600 nm, and a wavelength region of greater than about 600 nm and less than or equal to about 700 nm. It may be a light absorbing material, and the N-type semiconductor may be the aforementioned N-type semiconductor composition. For example, the P-type semiconductor may be an absorbing material that selectively absorbs light in a wavelength region of about 500 nm to about 600 nm and the N-type semiconductor may be the aforementioned N-type semiconductor composition.

For example, the P-type semiconductor may be, for example, a light absorbing material having a LUMO energy level of about 3.0 eV to about 3.6 eV and a HOMO energy level of about 5.1 eV to about 5.7 eV. Within this range, the P-type semiconductor may be, for example, a light absorbing material having a LUMO energy level of about 3.1 eV to about 3.5 eV and a HOMO energy level of 5.2 eV to about 5.6 eV.

For example, the P-type semiconductor may be a light absorbing material having a core structure including, for example, an electron donating moiety, a pi conjugated linking group, and an electron accepting moiety. As a specific example of the p-type semiconductor, the compounds disclosed in US Patent Publication No. 2018-0062112 may be used. The entirety of US Patent Publication No. 2018-0062112 is incorporated herein by reference.

The P-type semiconductor may include, for example, a compound represented by Chemical Formula 8 as the compound having the core structure, but is not limited thereto.

[Chemical Formula 8]

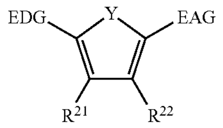

In Chemical Formula 8,

Y is Se, Te, S, SO, $SO_2$, or $SiR^hR^i$,

EDG is an electron donating group,

EAG is an electron accepting group, and $R^{21}$, $R^{22}$, $R^h$, and $R^i$ are independently hydrogen or a monovalent substituent.

Herein, the monovalent substituent may be, for example, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, but is not limited thereto.

The P-type semiconductor may be, for example, a light absorbing material represented by Chemical Formula 8A, but is not limited thereto.

[Chemical Formula 8A]

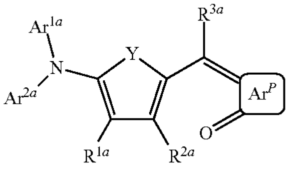

In Chemical Formula 8A,

Y is Se, Te, S, SO, $SO_2$, or $SiR^hR^i$, $Ar^p$ is a substituted or unsubstituted 5-membered ring, a substituted or unsubstituted 6-membered ring, or a condensed ring of two or more of the foregoing rings, $Ar^{1a}$ and $Ar^{2a}$ are independently a substituted or unsubstituted C6 to C30 aryl group or a substituted or unsubstituted C3 to C30 heteroaryl group, wherein $Ar^{1a}$ and $Ar^{2a}$ are independently present or linked to each other by a linker of $G^1$ to form a ring, wherein $G^1$ is one of a single bond, $-(CR^jR^k)_{n2}-$, —O—, —S—, —Se—, —N═, $-NR^l-$, $-SiR^mR^n-$, and $-GeR^oR^p-$ and n2 is 1 or 2, and $R^{1a}$ to $R^{3a}$ and $R^h$ to $R^p$ are independently hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

The P-type semiconductor may be for example a light absorbing material represented by one of Chemical Formulae 8A-1 to 8A-4, but is not limited thereto.

[Chemical Formula 8A-1]

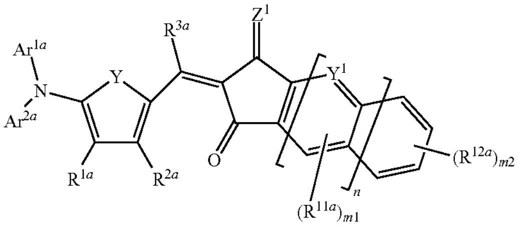

[Chemical Formula 8A-2]

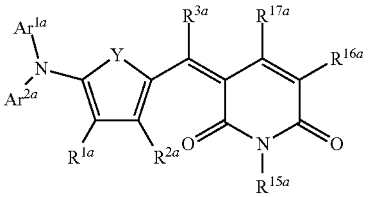

[Chemical Formula 8A-3]

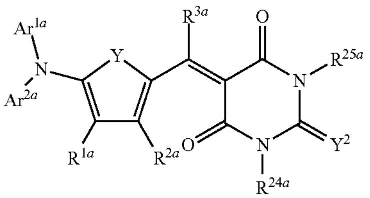

-continued

[Chemical Formula 8A-4]

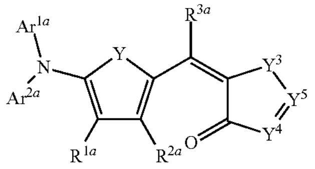

In Chemical Formulae 8A-1 to 8A-4,

Y is Se, Te, S, SO, $SO_2$, or $SiR^hR^i$, $Z^1$ is O or $CR^pR^r$, $Y^1$ is N or $CR^s$, $Y^2$ is one of O, S, Se, Te, and $C(R^t)(CN)$, $Y^3$ is O, S, Se, or Te, $Y^4$ is N or $NR^{18a}$, $Y^5$ is $CR^{19a}$ or $C{=}CR^{20a}(CN)$, $Ar^{1a}$ and $Ar^{2a}$ are independently a substituted or unsubstituted C6 to C30 aryl group or a substituted or unsubstituted C3 to C30 heteroaryl group, wherein $Ar^{1a}$ and $Ar^{2a}$ are independently present or linked to each other to form a ring, $R^{1a}$ to $R^{3a}$, $R^{11a}$, $R^{12a}$, $R^{15a}$ to $R^{20a}$, $R^{24a}$, $R^{25a}$, $R^h$, $R^i$, and $R^q$ to $R^t$ are independently hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, n1 is 0 or 1, m1 is 0 or 1, and m2 is an integer ranging from 0 to 4.

The light absorbing material represented by one of Chemical Formulae 8A-1 to 8A-4 may be for example one of compounds of Group 9 to Group 12, but is not limited thereto.

[Group 9]

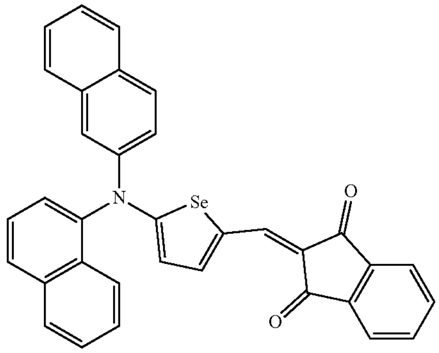

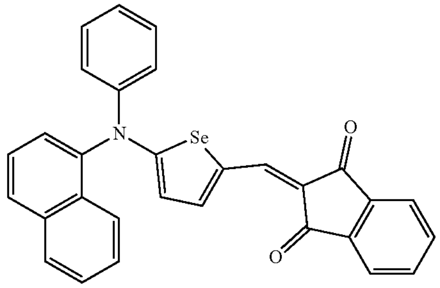

-continued
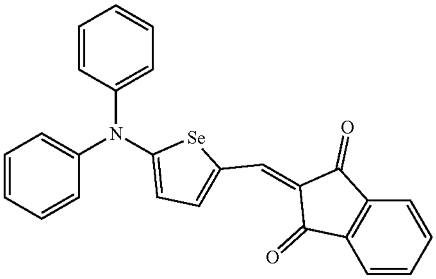
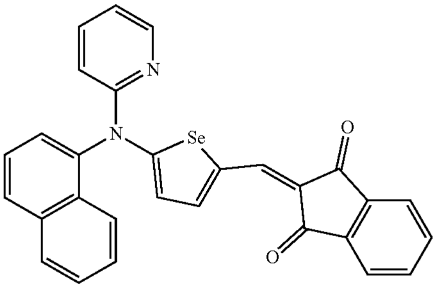
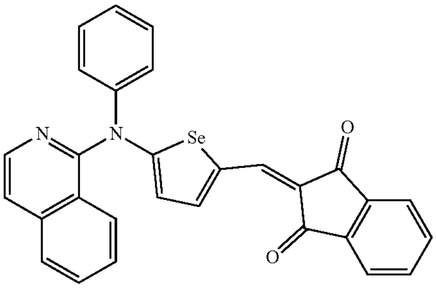
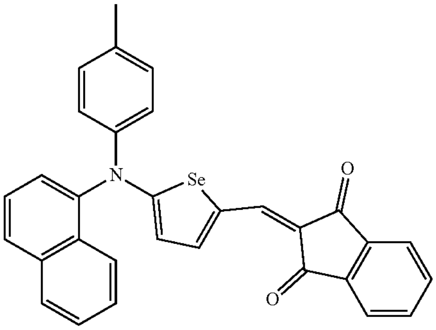
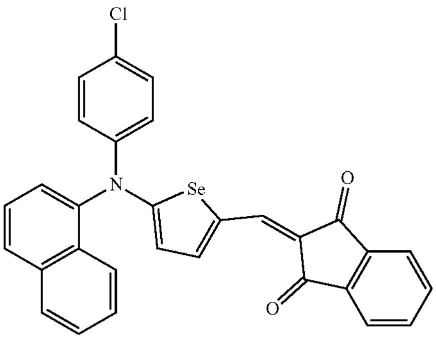
-continued
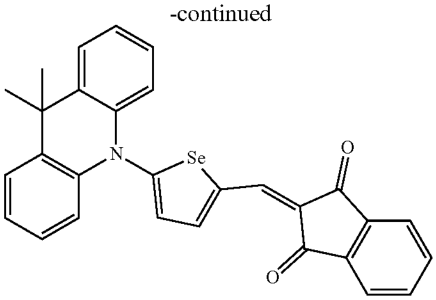
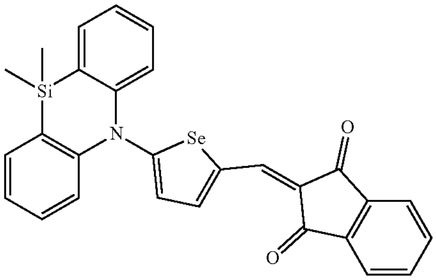
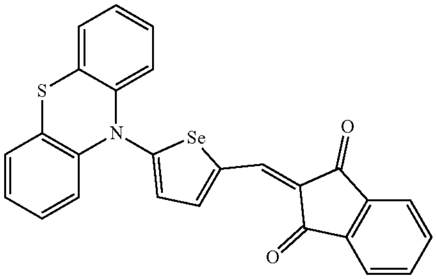
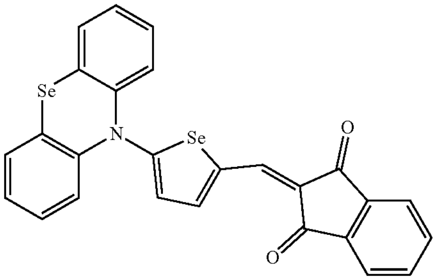
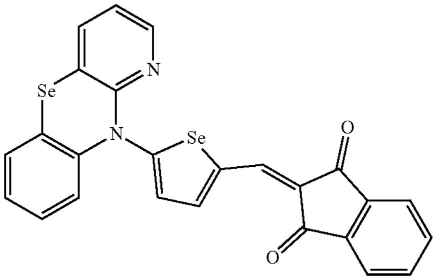

[Group 10]
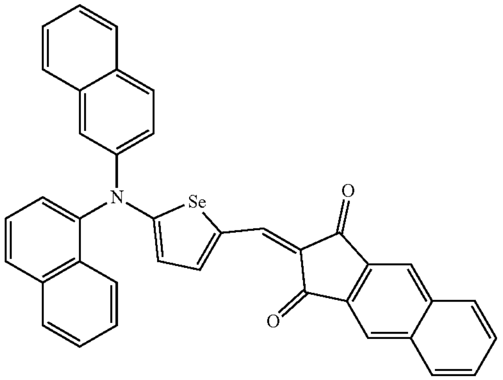
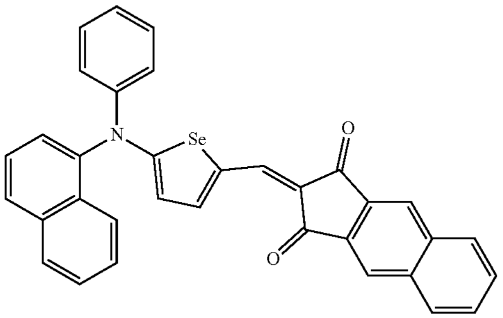
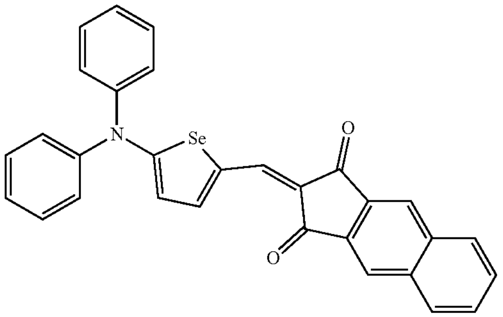
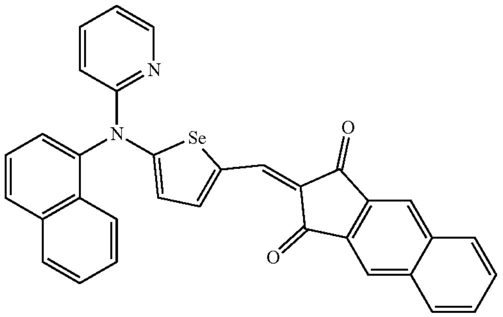
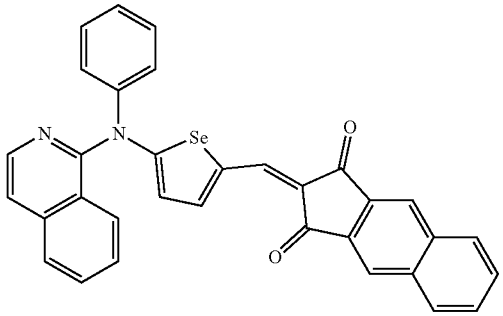
-continued
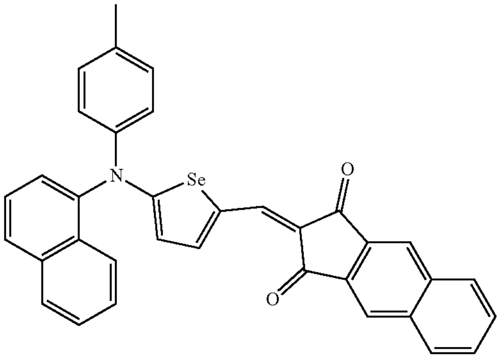
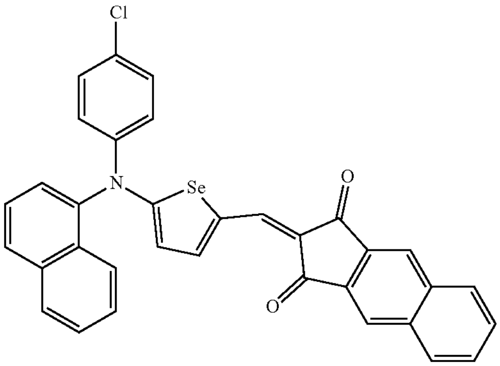
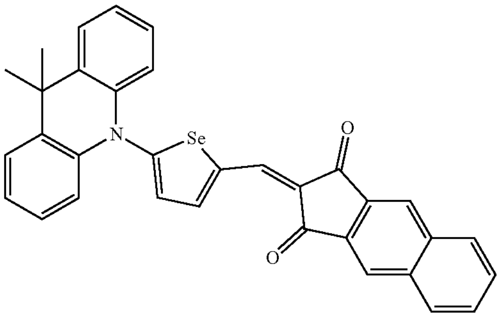
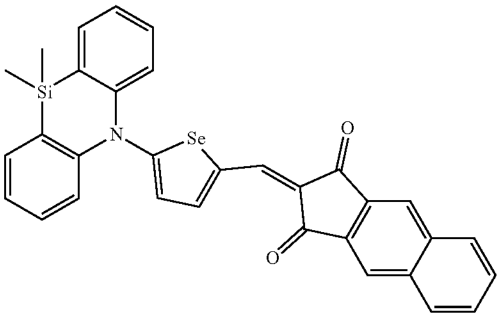
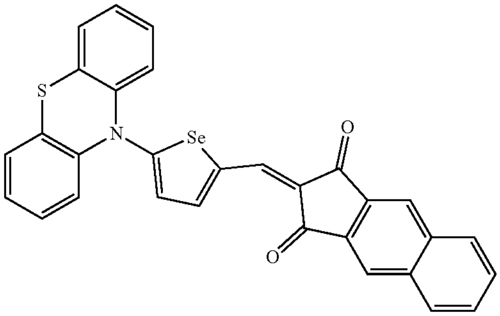

-continued
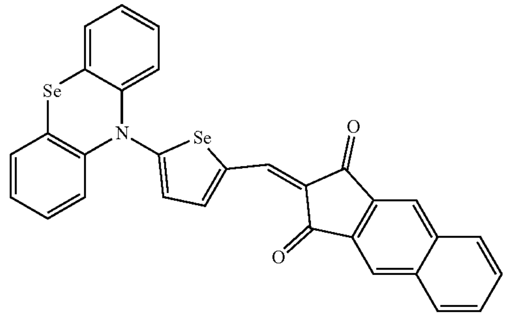
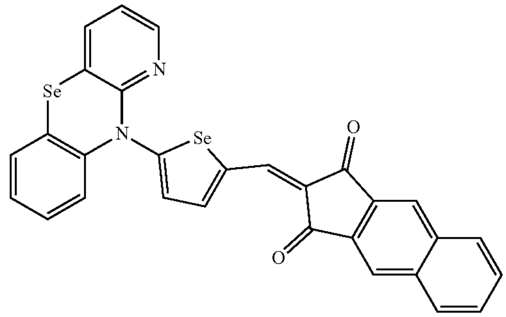
[Group 11]
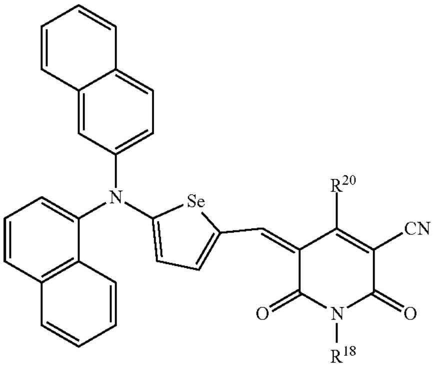
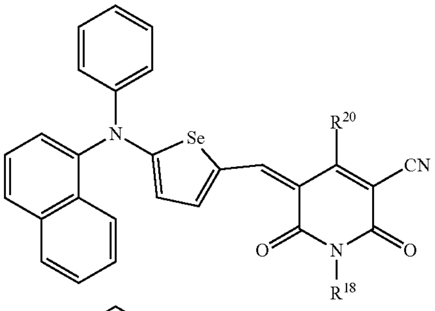
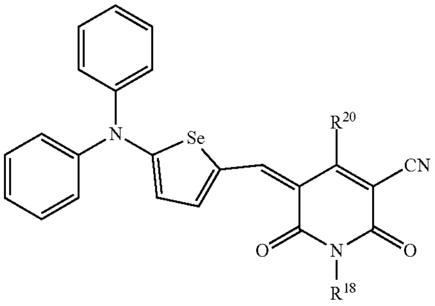
-continued
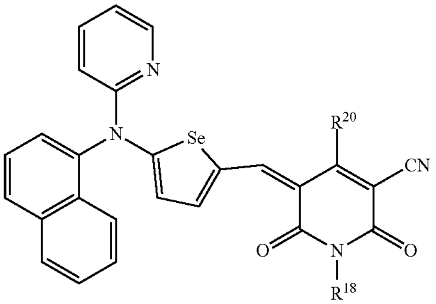
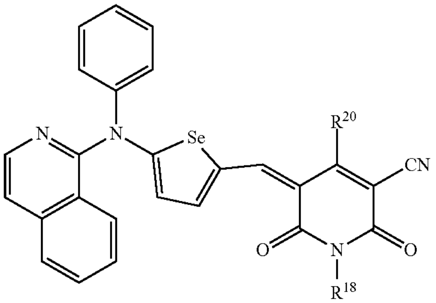
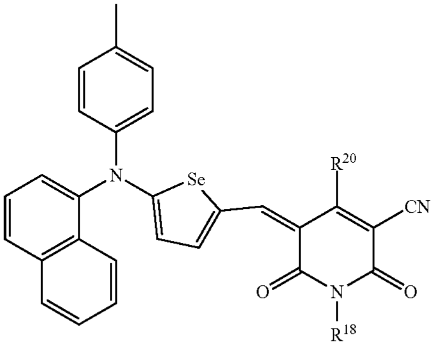
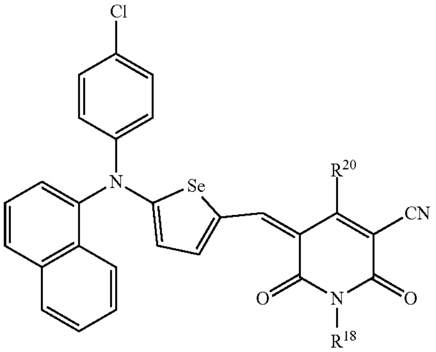
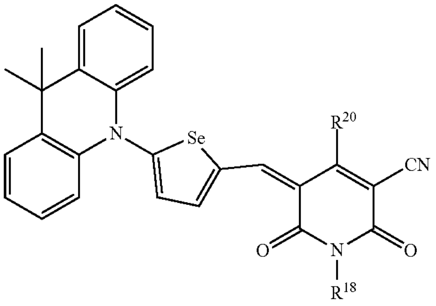

-continued
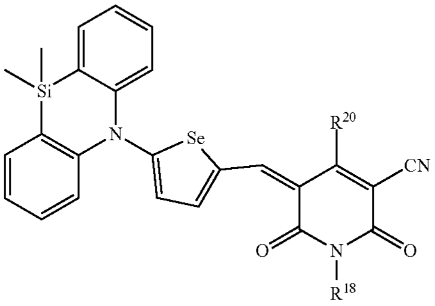
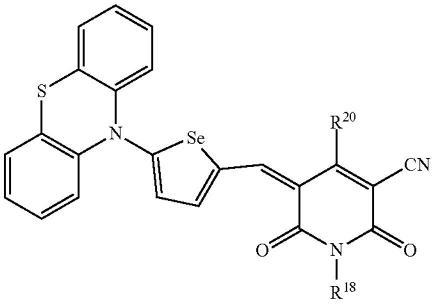
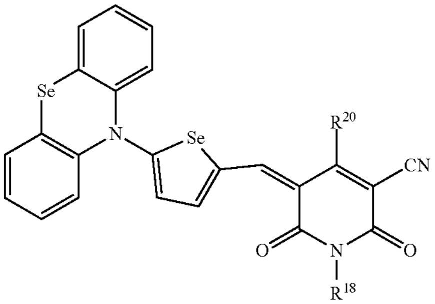
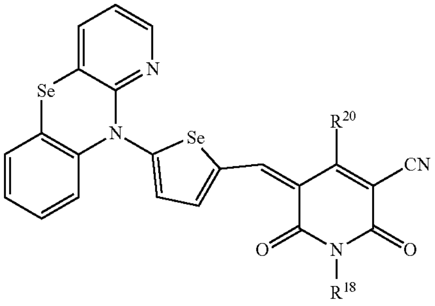
-continued
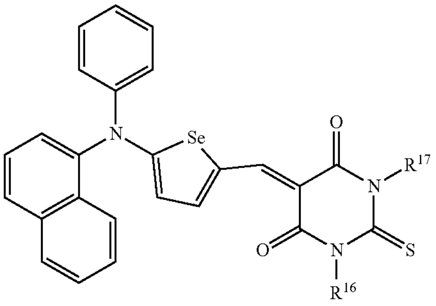
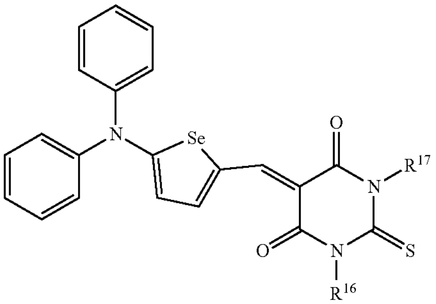
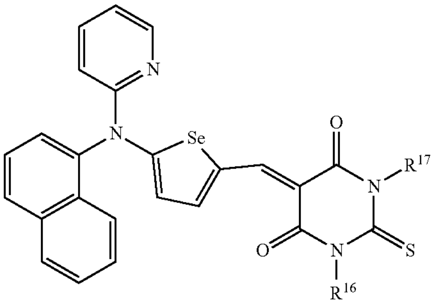
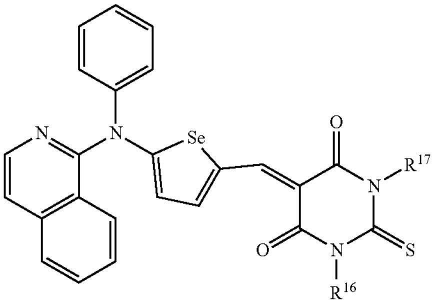
[Group 12]
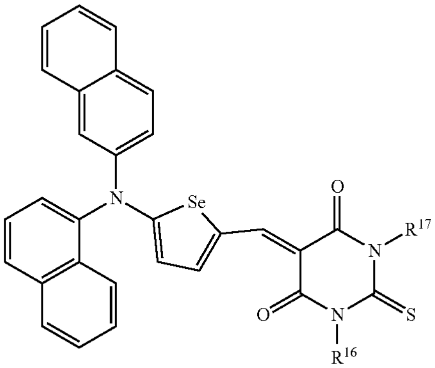
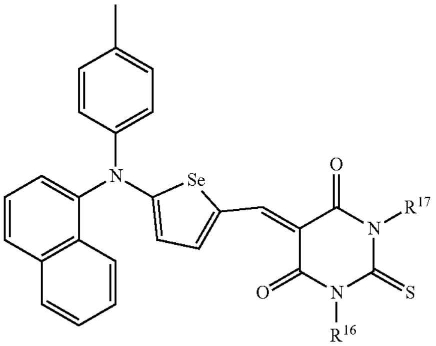

-continued

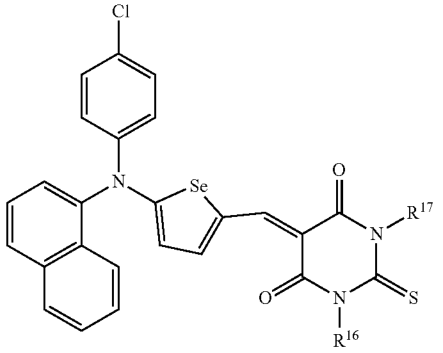

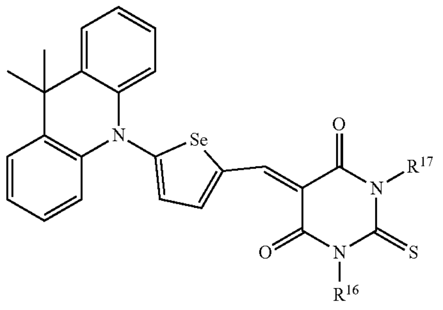

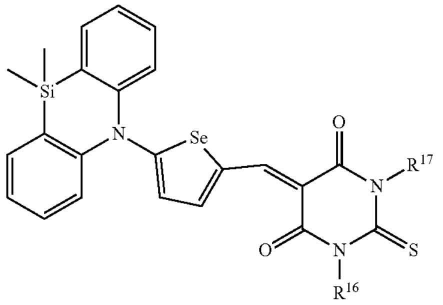

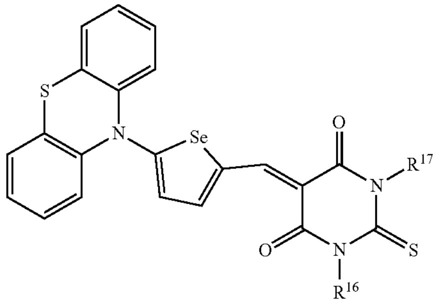

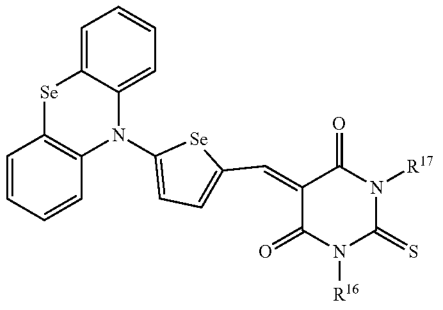

-continued

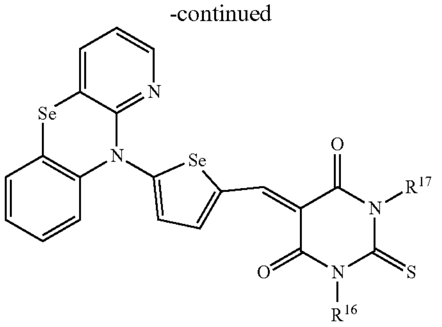

In Groups 9 to 12, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, and $R^{16}$, $R^{17}$, $R^{18}$, and $R^{20}$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof.

The aforementioned N-type semiconductor composition may be used as the N-type semiconductor.

The fullerene or fullerene derivative has LUMO energy level, HOMO energy level, and bandgap energy which are effective for electrical matching with the aforementioned P-type semiconductor.

The P-type semiconductor and the N-type semiconductor composition may be formed into the active layer by codeposition using sublimation.

For example, the light absorption characteristics of the active layer including the N-type semiconductor composition may be different from the light absorption characteristics of the active layer including an unsubstituted fullerene (e.g., C60 fullerene), and an active layer including an N-type semiconductor composition may have reduced abnormal absorption in a short wavelength region of visible light, for example from about 400 nm to about 500 nm. For example, the absorption coefficient at a 450 nm wavelength of the active layer including the N-type semiconductor composition may be smaller than the absorption coefficient at a 450 nm wavelength of the active layer including unsubstituted fullerene (e.g., C60 fullerene). For example, the absorption coefficient at a 450 nm wavelength of the active layer including the N-type semiconductor composition may be, for example, about 75% or less of the absorption coefficient at a 450 nm wavelength of the active layer including unsubstituted fullerene (e.g., C60 fullerene).

The light absorption characteristics of the active layer may be expressed by a combination of light absorption characteristics by the P-type semiconductor and light absorption characteristics by the N-type semiconductor composition. Accordingly, the active layer including the P-type semiconductor selectively absorbing light in a wavelength region of about 500 nm to about 600 nm and the N-type semiconductor composition may increase wavelength selectivity due to easy separation of an absorption peak compared with the active layer including the P-type semiconductor selectively absorbing in a wavelength region of about 500 nm to about 600 nm and the unsubstituted fullerene (e.g., C60 fullerene). Accordingly, the former active layer may be effectively used for an organic photoelectric device requiring wavelength selectivity.

The active layer may include an intrinsic layer (I layer) formed by codepositing the aforementioned P-type semiconductor and N-type semiconductor composition. The P-type semiconductor and N-type semiconductor composition may be included in a volume ratio of about 1:9 to about 9:1, about 2:8 to about 8:2, about 3:7 to about 7:3, about 4:6 to about 6:4, or about 5:5.

The active layer may further include a P-type layer and/or an N-type layer in addition to the intrinsic layer. The P-type layer may include the P-type semiconductor and the N-type layer may include the aforementioned N-type semiconductor composition. For example, the active layer may include various combinations of a P-type layer/an I layer, an I layer/an N-type layer, a P-type layer/an I layer/an N-type layer, and the like.

The organic photoelectric device 100 may further include a charge auxiliary layer (not shown) between the first electrode 10 and the active layer and/or a charge auxiliary layer between the second electrode 20 and the active layer. The organic photoelectric device is illustrated in FIG. 2.

Figure 2:
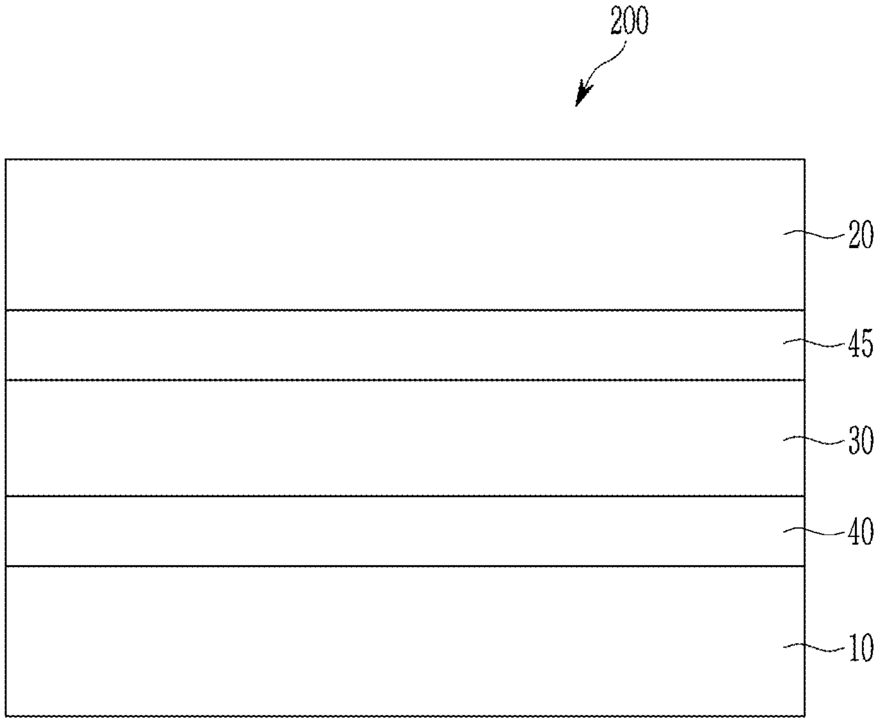
FIG. 2 is a cross-sectional view illustrating an organic photoelectric device according to another embodiment

FIG. 2 is a cross-sectional view showing an organic photoelectric device according to another example embodiment.

Referring to FIG. 2, an organic photoelectric device 200 according to the present embodiment includes a first electrode 10 and a second electrode 20 facing each other, and an organic layer 30 between the first electrode 10 and the second electrode 20, like the above embodiment.

However, the organic photoelectric device 200 according to the present embodiment further includes charge auxiliary layers 40 and 45 between the first electrode 10 and the active layer, and the second electrode 20 and the organic layer 30, unlike the above embodiment.

The charge auxiliary layers 40 and 45 may make holes and electrons separated in the organic layer 30 be transported easily to improve efficiency.

The charge auxiliary layers 40 and 45 may include at least one selected from a hole injection layer for facilitating hole injection, a hole transport layer for facilitating hole transport, an electron blocking layer for preventing electron transport, an electron injection layer for facilitating electron injection, an electron transport layer for facilitating electron transport, and a hole blocking layer for preventing hole transport.

The charge auxiliary layers 40 and 45 may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layers 40 and 45 may include the aforementioned N-type semiconductor composition.

The organic photoelectric devices 100 and 200 may further include an anti-reflection layer (not shown) on one surface of the first electrode 10 or the second electrode 20. The anti-reflection layer is disposed at a light incidence side and lowers reflectance of light of incident light and thereby light absorbance is further improved. For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5, and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the organic photoelectric devices 100 and 200, when light enters from the first electrode 10 or second electrode 20 and the organic layer 30 (e.g., active layer) absorbs light in a predetermined wavelength region, excitons may be produced from the inside. The excitons are separated into holes and electrons in the organic layer 30, and the separated holes are transported to an anode that is one of the first electrode 10 and the second electrode 20 and the separated electrons are transported to the cathode that is the other of the first electrode 10 and the second electrode 20 so as to flow a current.

The organic photoelectric devices 100 and 200 may be applied to a solar cell, an image sensor, a photodetector, a photosensor, and an organic light emitting diode (OLED), but is not limited thereto.

The organic photoelectric device may be for example applied to an image sensor.

Hereinafter, an example of an image sensor including the photoelectric device is described referring to drawings. As an example of an image sensor, an organic CMOS image sensor is described.

Figure 3:
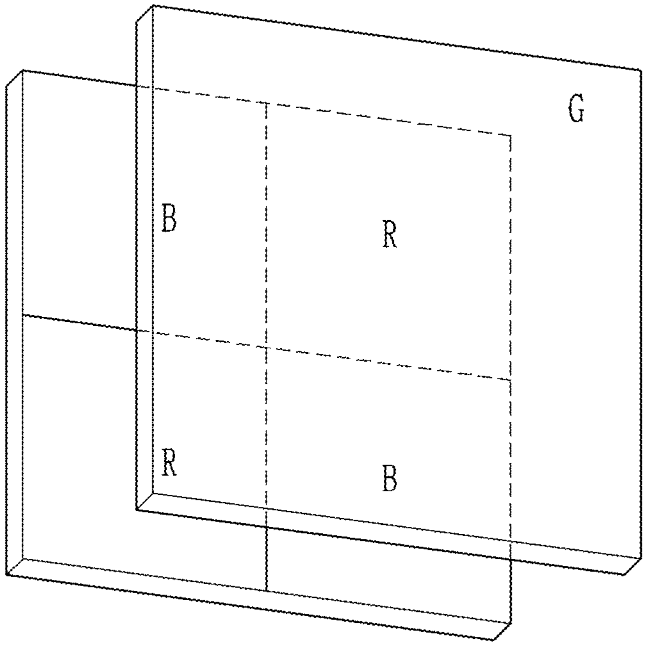
FIG. 3 is a plan view schematically illustrating a CMOS image sensor according to an embodiment.
Figure 4:
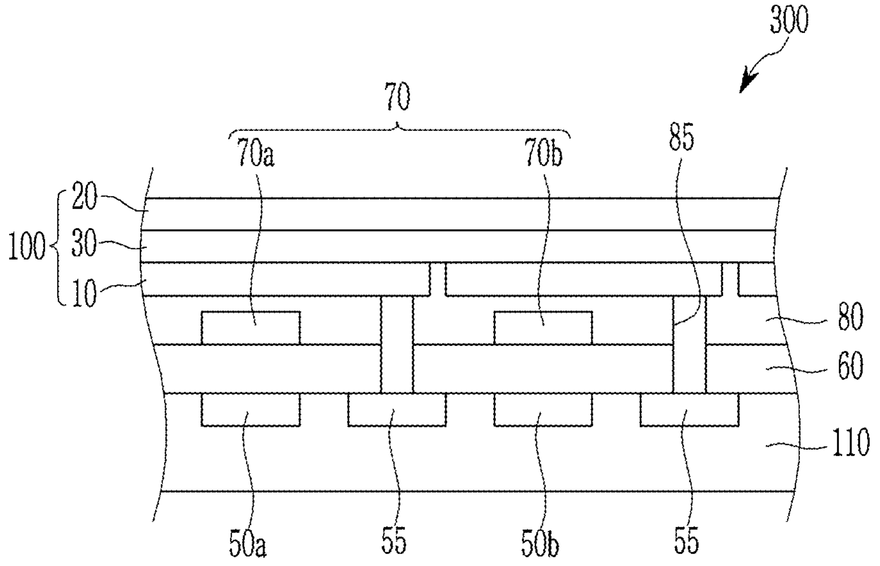
FIG. 4 is a cross-sectional view illustrating an example of the CMOS image sensor of FIG. 3.

FIG. 3 is a schematic top plan view of an organic CMOS image sensor according to an embodiment and FIG. 4 is a cross-sectional view showing one example of the organic CMOS image sensor of FIG. 3.

Referring to FIGS. 3 and 4, an organic CMOS image sensor 300 according to an example embodiment includes a semiconductor substrate 110 integrated with photo-sensing devices 50*a* and 50*b*, a transmission transistor (not shown) and a charge storage 55, a lower insulation layer 60, a color filter layer 70, an upper insulation layer 80, and an organic photoelectric device 100.

The semiconductor substrate 110 may be a silicon substrate, and is integrated with the photo-sensing devices 50*a* and 50*b*, the transmission transistor (not shown), and the charge storage 55. The photo-sensing devices 50*a* and 50*b* may be photodiodes.

The photo-sensing devices 50*a* and 50*b*, the transmission transistor, and/or the charge storage 55 may be integrated in each pixel, and as shown in the drawing, the photo-sensing devices 50*a* and 50*b* may be respectively included in a blue pixel and a red pixel and the charge storage 55 may be included in a green pixel.

The photo-sensing devices 50*a* and 50*b* sense light, the information sensed by the photo-sensing devices may be transferred by the transmission transistor, the charge storage 55 is electrically connected to the organic photoelectric device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing device 50*a* and 50*b*.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70*a* formed in a blue pixel and a red filter 70*b* in a red pixel. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned organic photoelectric device 100 is formed on the upper insulation layer 80. The organic photoelectric device 100 includes the first electrode 10, the organic layer 30, and the second electrode 20 as described above. In the drawing, the first electrode 10, the organic layer 30, and the second electrode 20 are sequentially stacked, but this disclosure is not limited thereto, and for example they may be stacked in an order of the second electrode 20, the organic layer 30, and the first electrode 10.

The first electrode 10 and the second electrode 20 may be all light-transmitting electrodes and the organic layer 30 is the same as described above. The organic layer 30 may for example selectively absorb light in a green wavelength region and may replace a color filter of a green pixel.

Light in a green wavelength region of light that enters from the second electrode 20 is mainly absorbed by the organic layer 30 and photoelectrically converted and light in a remaining wavelength region is transmitted through the first electrode 10 and is sensed by the photo-sensing devices 50*a* and 50*b*.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device 100 has a stack structure thereby a size of an image sensor may be reduced to realize a down-sized image sensor.

In addition, the organic layer includes the fullerene derivative having optical absorption characteristics shifted toward a short wavelength as described above and thus may increase wavelength selectivity compared with the one including the unsubstituted C60 fullerene.

The organic photoelectric device selectively absorbing light in a green wavelength region is for example stacked but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a green photo-sensing device and a blue photo-sensing device may be integrated in the semiconductor substrate 110.

Figure 5:
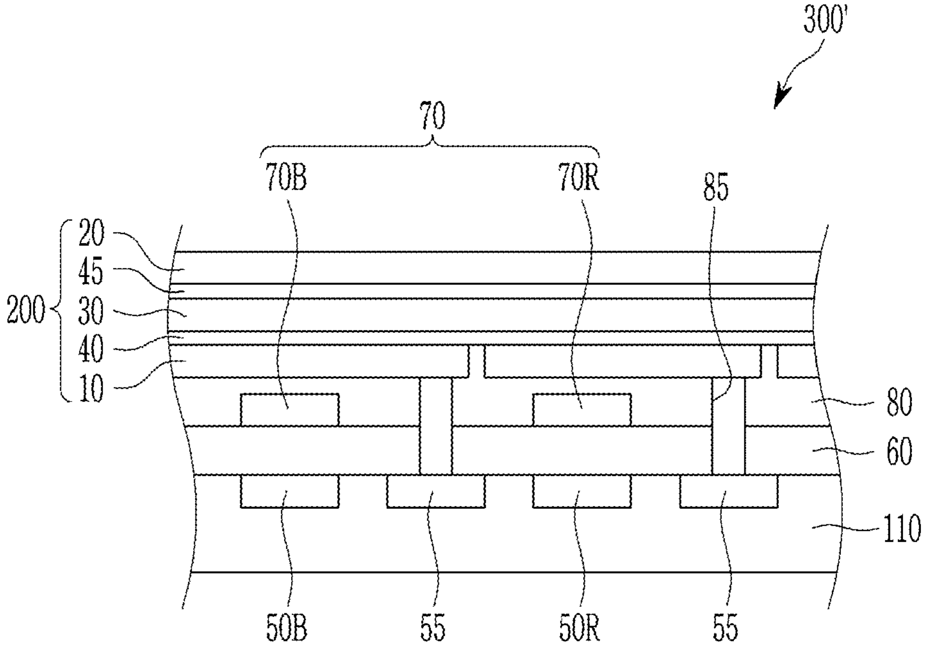
FIG. 5 is a cross-sectional view showing another example of a CMOS image sensor.

FIG. 4 illustrates an embodiment including the organic photoelectric device 100 of FIG. 1, but is not limited thereto, and the photoelectric device 200 of FIG. 2 may be applied thereto. FIG. 5 is a cross-sectional view illustrating a CMOS image sensor 300' including the organic photoelectric device 200.

Figure 6:
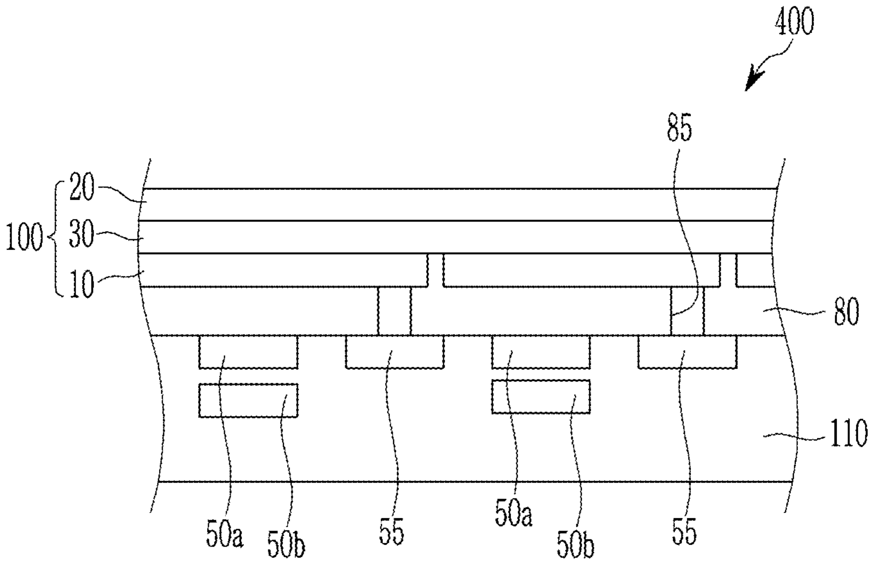
FIG. 6 is a cross-sectional view showing another example of a CMOS image sensor.

FIG. 6 is a cross-sectional view showing another example of the organic CMOS image sensor.

The organic CMOS image sensor 400 according to the present embodiment like the above embodiment includes a semiconductor substrate 110 integrated with photo-sensing devices 50*a* and 50*b*, a transmission transistor (not shown), and a charge storage 55, an upper insulation layer 80 having a through-hole 85, and an organic photoelectric device 100.

However, in the CMOS image sensor 400 according to the present embodiment unlike the above embodiment, the photo-sensing devices 50*a* and 50*b* are stacked in a vertical direction, but the color filter layer 70 is omitted. The photo-sensing devices 50*a* and 50*b* are electrically connected to charge storage (not shown) and may be transferred by the transmission transistor. The photo-sensing devices 50*a* and 50*b* may selectively absorb light in each wavelength region depending on a stacking depth.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device selectively absorbing light in a green wavelength region is stacked and the red photo-sensing device and the blue photo-sensing device are stacked, and thereby a size of an image sensor may be reduced to realize a down-sized image sensor.

In FIG. 6, the organic photoelectric device selectively absorbing light in a green wavelength region is for example stacked, but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a green photo-sensing device and a blue photo-sensing device may be integrated in the semiconductor substrate 110.

Figure 7:
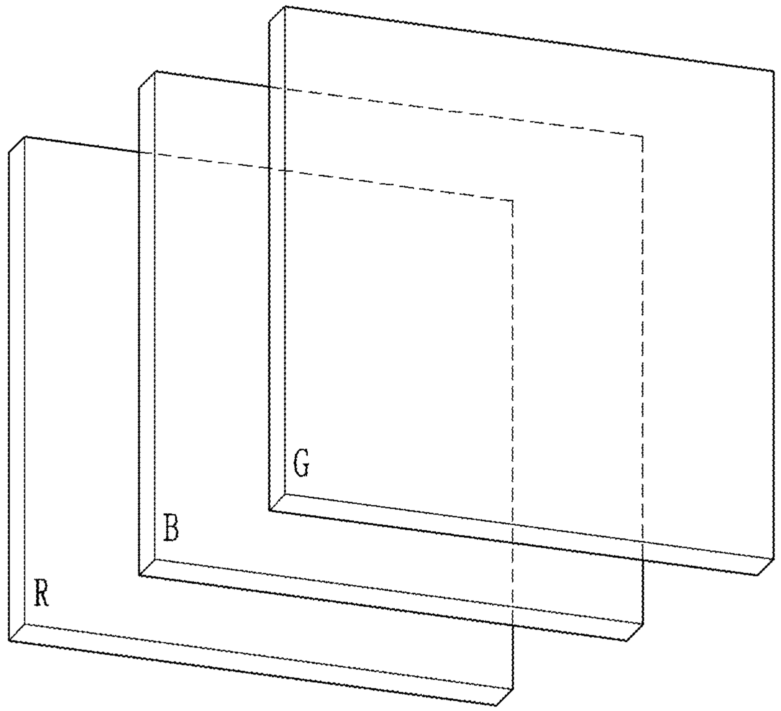
FIG. 7 is a plan view schematically illustrating a CMOS image sensor according to another embodiment.
Figure 8:
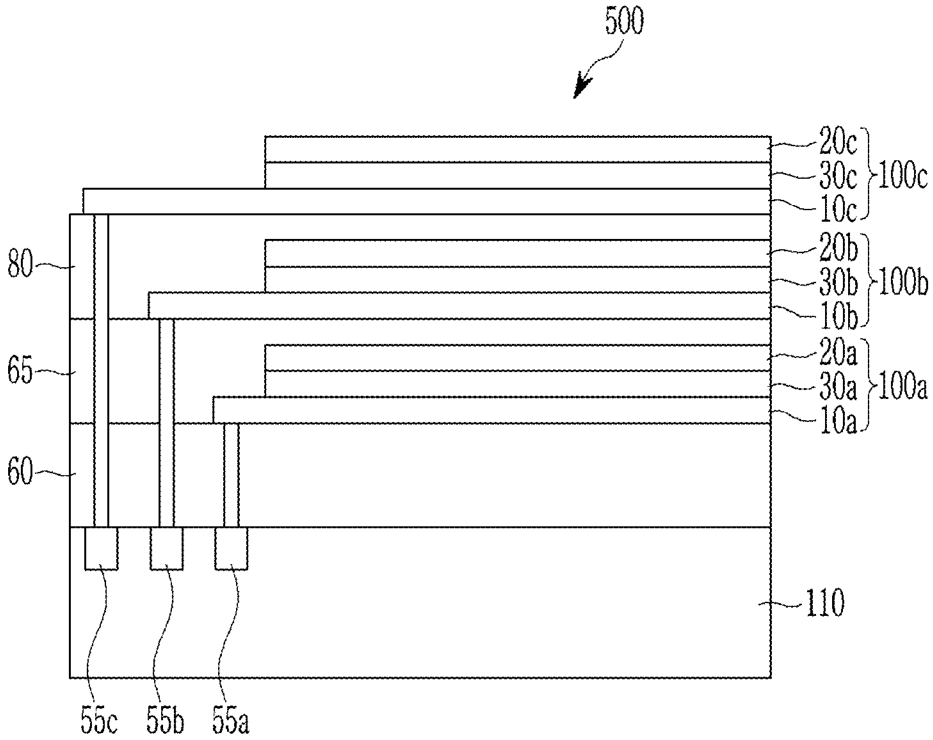
FIG. 8 is a cross-sectional view of the CMOS image sensor according to another embodiment.

FIG. 7 is a schematic top plan view showing an organic CMOS image sensor according to another embodiment and FIG. 8 is a cross-sectional view of the organic CMOS image sensor according to another embodiment.

The organic CMOS image sensor 500 according to the present embodiment includes a green organic photoelectric device selectively absorbing light in a green wavelength region, a blue organic photoelectric device selectively absorbing light in a blue wavelength region, and a red organic photoelectric device selectively absorbing light in a red wavelength region that are stacked.

The organic CMOS image sensor 500 according to the present embodiment includes a semiconductor substrate 110, a lower insulation layer 60, an intermediate insulation layer 65, an upper insulation layer 80, a first organic photoelectric device 100*a*, a second organic photoelectric device 100*b*, and a third organic photoelectric device 100*c*.

The semiconductor substrate 110 may be a silicon substrate, and is integrated with the transmission transistor (not shown) and the charge storages 55*a*, 55*b*, and 55*c*.

A metal line (not shown) and pad (not shown) are formed on the semiconductor substrate 110 and a lower insulation layer 60 is formed on the metal line and pad.

The first organic photoelectric device 100*a* is formed on the lower insulation layer 60.

The first organic photoelectric device 100*a* includes a first electrode 10*a* and a second electrode 20*a* facing each other and an organic layer 30*a* disposed between the first electrode 10*a* and the second electrode 20*a*. The first electrode 10*a*, the second electrode 20*a*, and the organic layer 30*a* are the same as described above and the organic layer 30*a* may selectively absorb light in one wavelength region of red, blue, and green. For example, the first organic photoelectric device 100*a* may be a red organic photoelectric device.

In the drawing, the first electrode 10*a*, the organic layer 30*a*, and the second electrode 20*a* are sequentially stacked, but this disclosure is not limited thereto, and for example they may be stacked in an order of the second electrode 20*a*, the organic layer 30*a*, and the first electrode 10*a*.

The intermediate insulation layer 65 is formed on the first organic photoelectric device 100*a*.

The second organic photoelectric device 100*b* is formed on the intermediate insulation layer 65.

The second organic photoelectric device 100*b* includes a first electrode 10*b* and a second electrode 20*b* facing each other and an organic layer 30*b* disposed between the first electrode 10*b* and the second electrode 20*b*. The first electrode 10*b*, the second electrode 20*b*, and the organic layer 30*b* are the same as described above and the organic layer 30*b* may selectively absorb light in one wavelength region of red, blue and green. For example, the second photoelectric device 100*b* may be a blue organic photoelectric device.

In the drawing, the first electrode 10*b*, the organic layer 30*b*, and the second electrode 20*b* are sequentially stacked, but this disclosure is not limited thereto, and for example they may be stacked in an order of the second electrode 20*b*, the organic layer 30*b*, and the first electrode 10*b*.

The upper insulation layer 80 is formed on the second organic photoelectric device 100*b*. The lower insulation layer 60, the intermediate insulation layer 65, and the upper insulation layer 80 have a plurality of through-holes exposing the charge storages 55*a*, 55*b*, and 55*c*.

The third organic photoelectric device 100*c* is formed on the upper insulation layer 80. The third organic photoelectric device 100*c* includes a first electrode 10*c* and a second electrode 20*c* facing each other and an organic layer 30*c* disposed between the first electrode 10*c* and the second electrode 20*c*. The first electrode 10*c*, the second electrode 20*c*, and the organic layer 30*c* are the same as described above and the organic layer 30*c* may selectively absorb light in one wavelength region of red, blue, and green. For example, the third organic photoelectric device 100*c* may be a green organic photoelectric device.

In the drawing, the first electrode 10*c*, the organic layer 30*c*, and the second electrode 20*c* are sequentially stacked, but this disclosure is not limited thereto, and for example they may be stacked in an order of the second electrode 20*c*, the organic layer 30*c*, and the first electrode 10*c*.

Focusing lens (not shown) may be further formed on the organic photoelectric device 100*c*. The focusing lens may control a direction of incident light and gather the light in one region. The focusing lens may have a shape of, for example, a cylinder or a hemisphere, but is not limited thereto.

In the drawing, the first organic photoelectric device 100*a*, the second organic photoelectric device 100*b*, and the third organic photoelectric device 100*c* are sequentially stacked, but the present disclosure is not limited thereto, and they may be stacked in various orders.

As described above, the first organic photoelectric device 100*a*, the second organic photoelectric device 100*b*, and the third organic photoelectric device 100*c* that absorb light in different wavelength regions are stacked, and thereby a size of an image sensor may be reduced to realize a down-sized image sensor.

The image sensor may be applied to, for example, various electronic devices such as a mobile phone or a digital camera, but is not limited thereto.

Figure 9:
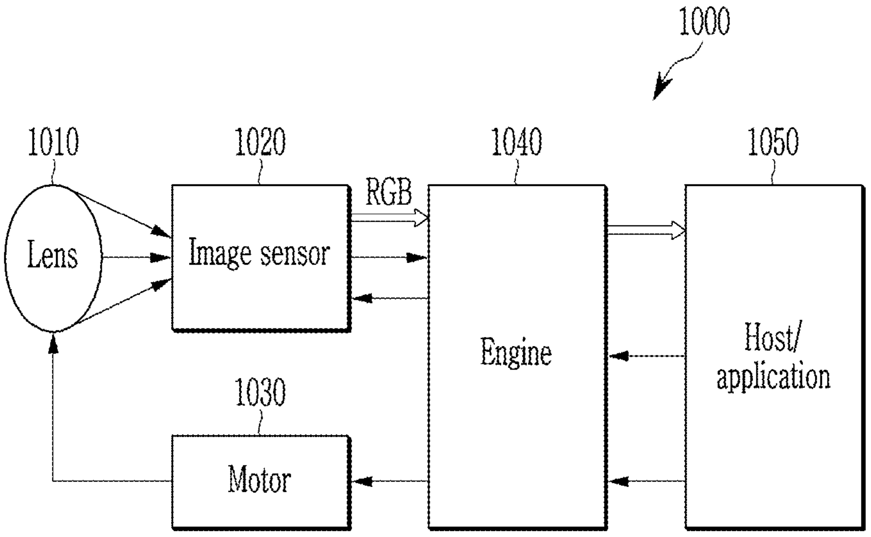
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

In example embodiments, the motor 1030, engine 1040, and host/application 1050 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Hereinafter, the embodiments are illustrated in more detail with reference to examples. However, these examples are exemplary, and the scope of claims is not limited thereto.

Synthesis Example: Synthesis of Fullerene Subunit Derivative

Synthesis Example 1

[Chemical Formula A]

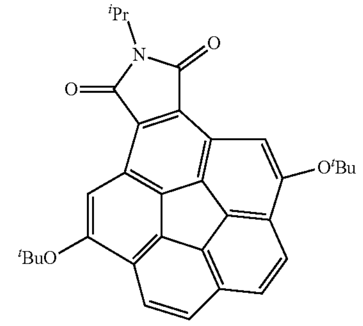

[Reaction Scheme A]

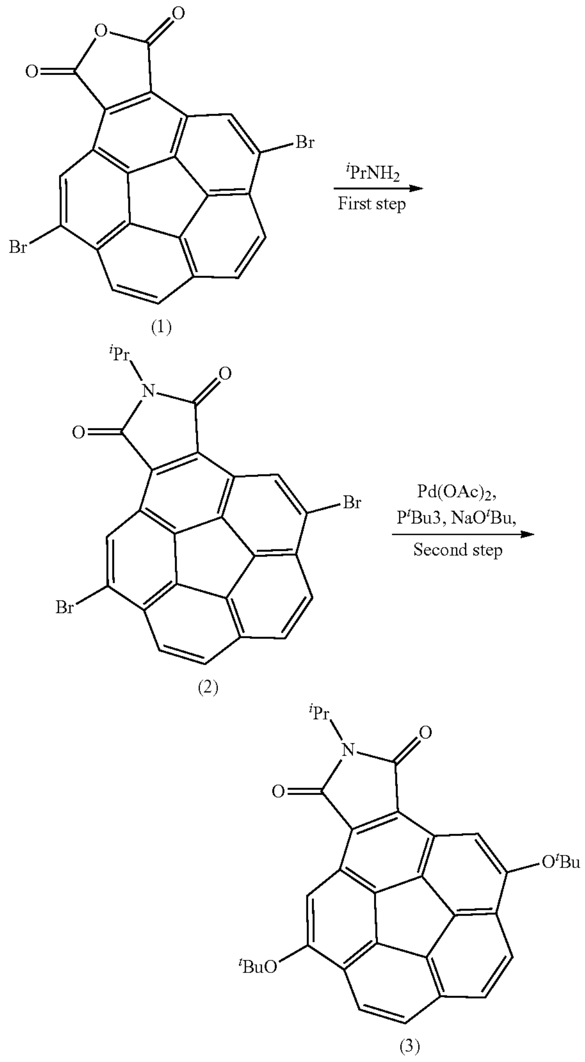

(1)

(2)

(3)

i) First Step

A suspension including a 1,8-dibromocorannulene derivative having dihydro-2,5-furandione (Compound (1), 1.8 g, 3.8 mmol), isopropylamine (0.4 ml, 4.7 mmol), and N-methylpyrrolidone (NMP, 12 ml) is prepared and put in a container of a microwave reactor. After reacting them at 180° C. for 30 minutes, a suspension in the container is mixed. Subsequently, NMP is removed under a vacuum distillation (less than or equal to 1 torr, greater than or equal to 50° C.). Then, chloroform is added to the residue and then, purified through silica gel column chromatography (an eluent: a mixture of chloroform and hexane in a volume ratio of 1:1).

After evaporating the solvent from the obtained solution, a solid therefrom is dissolved in chloroform, and a product therefrom is separated by using Recycle HPLC (Buckyprep 4.6φx250 mm; an eluent: chloroform). The solvent is evaporated from the solution to obtain an intermediate (Compound (2), 0.7 g, 1.4 mmol, yield: 36.8%).

ii) Second Step

The intermediate (Compound (2), 0.9 g, 1.7 mmol), a catalyst of $Pd(OAc)_2$ (palladium (II) acetate, 6.5 mg, 0.3 mmol), a base of $^tBuONa$ (sodium tert-butoxide, 0.7 g, 7.2 mmol), a toluene solution of $P(^tBu)_3$ (tri-tert-butylphosphine, 50 wt %, 0.3 ml, 0.6 mmol), and m-xylene (78 ml) are mixed in a flask and then, stirred by using an oil bath at 130° C. for 12 hours.

Subsequently, an evaporator (less than or equal to 300 mbar, greater than or equal to 40° C.) is used to remove the solvent. Then, chloroform is added to the residue and then, purified through silica gel column chromatography (an eluent: a mixture of chloroform and hexane in a volume ratio of 1:1).

After evaporating the solvent from the solution, a solid therefrom is dissolved in chloroform, and a product therefrom is separated by using Recycle HPLC (Buckyprep 4.6φx250 mm; an eluent: chloroform). The solvent is evaporated from the solution to obtain a compound represented by Chemical Formula A (Compound (3), 0.6 g, 1.2 mmol, yield: 69.8%).

$^1H$ NMR ($CDCl_3$): δ 7.98 (s, 1H), 7.95 (s, 1H), 7.89 (s, 2H), 7.75 (s, 1H), 7.72 (s, 1H), 4.50 to 4.60 (m, 1H), 1.70 (s, 18H), 1.54 (s, 3H), 1.52 (s, 3H)

Synthesis Example 2

[Chemical Formula B]

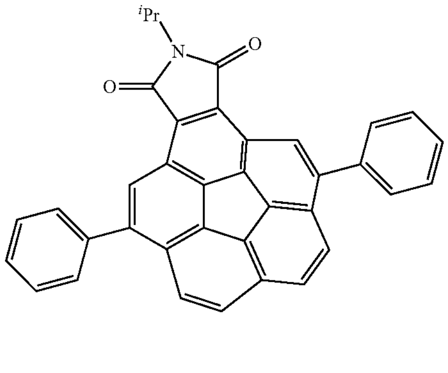

[Reaction Scheme B]

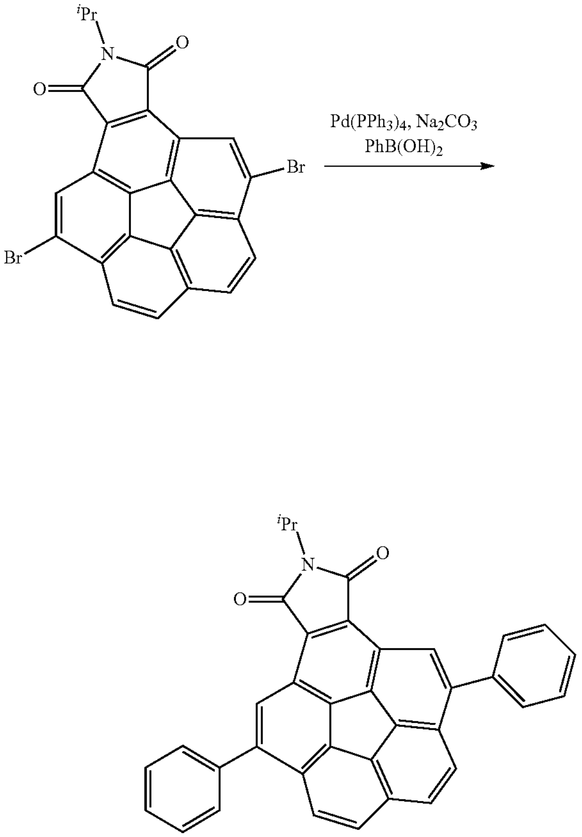

The compound (2) in Synthesis Example 1 (1.5 g, 2.9 mmol), $Pd(PPh_3)_4$ (tetrakis(triphenylphosphine)palladium (0), 0.2 g, 0.2 mmol), $Na_2CO_3$ (0.9 g, 8.7 mmol), phenyl boronic acid ($PhB(OH)_2$, 1.1 g, 8.7 mmol), and a mixed solvent (toluene (80 ml), EtOH (40 ml), and water (40 ml)) are mixed and then, stirred by using an oil bath at 90° C. for 12 hours to obtain a compound represented by Chemical Formula B (1.2 g, 2.3 mmol, yield: 78.7%).

$^1$H NMR ($CDCl_3$): δ 8.55 (s, 2H), 7.75 to 7.90 (m, 6H), 7.10 to 7.65 (m, 8H), 4.55 to 4.70 (m. 1H), 1.58 (s, 6H).

Synthesis Example 3

[Chemical Formula C]

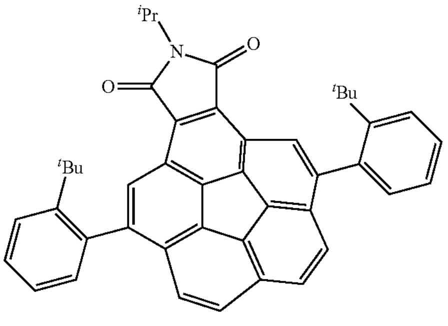

[Reaction Scheme C]

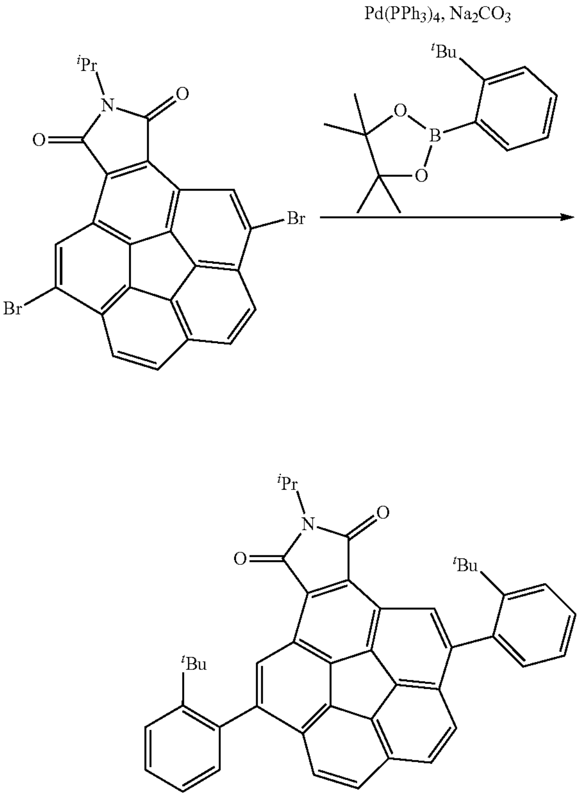

The compound (2) in Synthesis Example 1 (1.0 g, 2.0 mmol), $Pd(PPh_3)_4$ (0.2 g, 0.1 mmol), $Na_2CO_3$ (0.6 g, 5.9 mmol), phenyl boronic acid ester (2-tert-butylphenylboronic acid pinacol ester, 0.3 g, 11.8 mmol), and a mixed solvent (toluene (72 ml), EtOH (32 ml), and water (32 ml)) are mixed and then, stirred by using an oil bath at 90° C. for 12 hours to obtain a compound represented by Chemical Formula C (0.5 g, 0.8 mmol, yield: 40.6%).

$^1$H NMR ($CDCl_3$): δ 8.35 (s, 2H), 7.55 to 7.80 (m, 4H), 7.00 to 7.50 (m, 6H), 6.62 (d. 2H), 4.40 to 4.62 (m. 1H), 1.52 (s, 24H).

Synthesis Example 4

[Chemical Formula D]

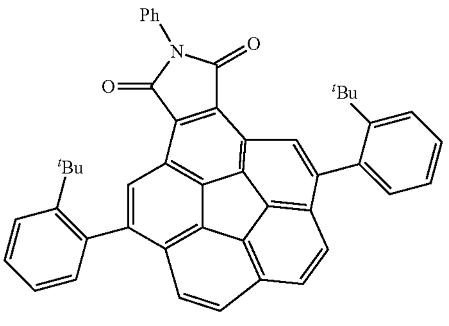

[Reaction Scheme D]

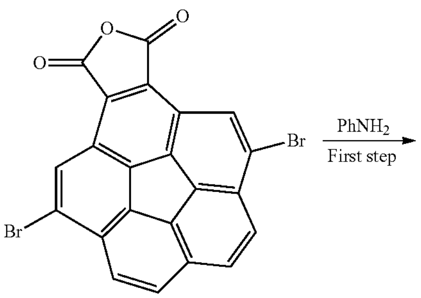

(1)

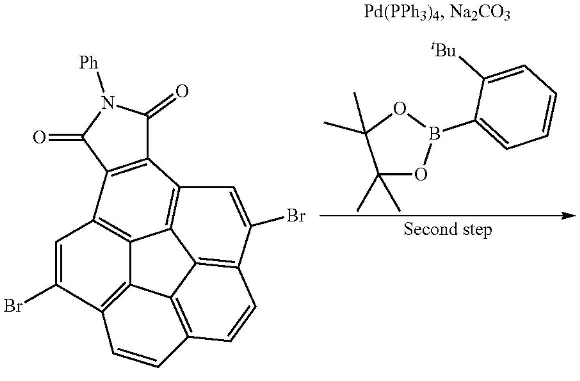

(2)

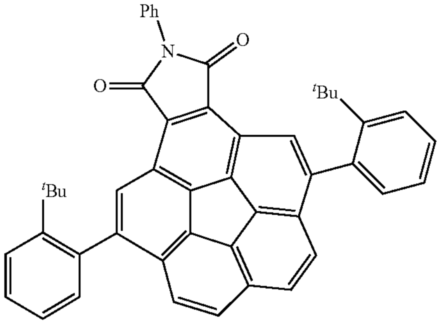

(3)

i) First Step

An intermediate (Compound (2), 0.8 g, 1.5 mmol, yield: 38.9%) is synthesized according to the same method as Synthesis Example 1 except that phenyl amine ($PhNH_2$) is used instead of the isopropylamine in the first step of Synthesis Example 1.

ii) Second Step

The intermediate (Compound (2), 0.7 g, 1.3 mmol), $Pd(PPh_3)_4$ (0.1 g, 0.1 mmol), $Na_2CO_3$ (0.4 g, 3.7 mmol), phenyl boronic acid ester (2-tert-butylphenylboronic acid pinacol ester, 1.9 g, 7.4 mmol), and a mixed solvent (toluene (44 ml), EtOH (20 ml), and water (20 ml)) are mixed and then, stirred by using an oil bath at 90° C. for 12 hours to obtain a compound represented by Chemical Formula D (Compound (3), 0.4 g, 0.6 mmol, yield: 50.1%).

$^1H$ NMR ($CDCl_3$): δ 8.35 to 8.45 (m, 2H), 7.68 to 7.79 (m, 4H), 7.43 to 7.56 (m, 9H), 7.08 to 7.20 (m, 2H), 6.60 to 6.68 (m, 2H), 1.59 (S, 9H).

Synthesis Example 5

[Chemical Formula E]

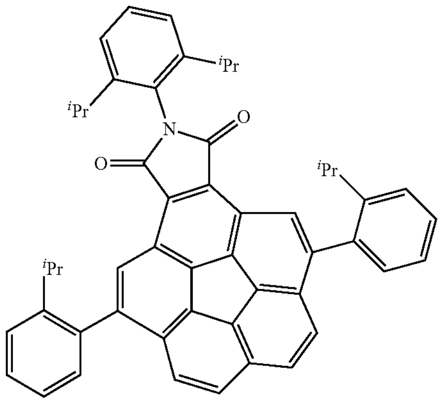

[Reaction Scheme E]

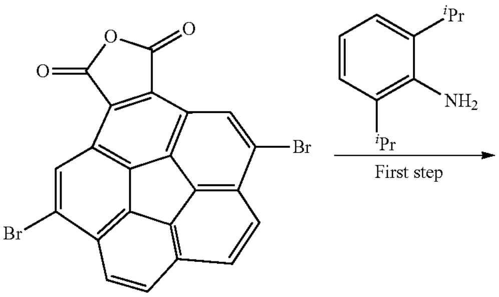

(1)

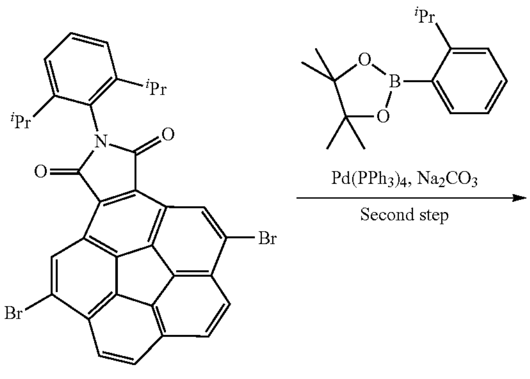

(2)

-continued

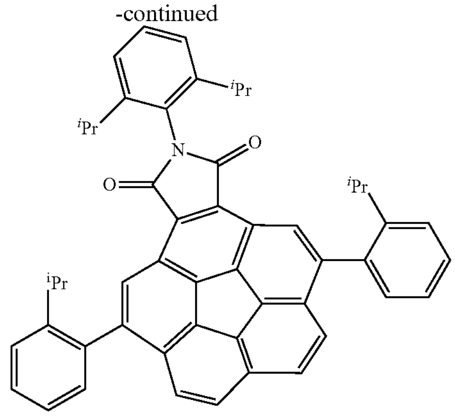

(3)

i) First Step

An intermediate (Compound (2), 0.9 g, 1.4 mmol, yield: 37.2%) is synthesized according to the same method as Synthesis Example 1 except that 2,6-diisopropylphenylamine ($(iPr)_2C_6H_3NH_2$) is used instead of the isopropylamine in the first step of Synthesis Example 1.

ii) Second Step

The intermediate (Compound (2), 1.2 g, 1.8 mmol), $Pd(PPh_3)_4$ (0.9 g, 5.5 mmol), $Na_2CO_3$ (0.6 g, 5.5 mmol), phenyl boronic acid ester (2-isopropylphenylboronic acid pinacol ester, 0.9 g, 5.5 mmol), and a mixed solvent (toluene (48 ml), EtOH (24 ml), and water (24 ml)) are mixed and then, reacted by using a microwave reactor at 155° C. for 1 hour to obtain a compound represented by Chemical Formula E (Compound (3), 1.0 g, 1.4 mmol, yield: 75.8%).

$^1H$ NMR ($CDCl_3$): δ 7.34 to 7.40 (m, 2H), 7.70-7.82 (m, 2H), 7.42 to 7.62 (m, 8H), 7.15 to 7.35 (m, 3H), 6.98 to 7.10 (m, 2H), 2.72 to 2.85 (m, 4H), 1.30 (s, 6H), 1.20 (s, 6H).

Comparative Synthesis Example 1

[Chemical Formula F]

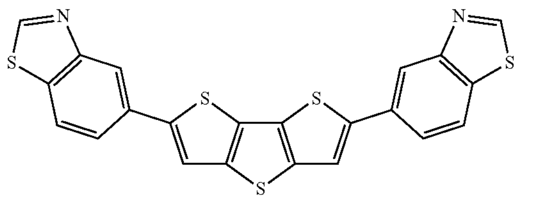

A compound represented by Chemical Formula F (0.1 g, 0.24 mmol, yield: 85%) is synthesized according to the same method as that of Scheme 2 disclosed in an article of Synthetic Metals 146 (2004) 251 to 257 except that benzo [d]thiazol-5-yl boronic acid (128.9 mg, 0.72 mmol) is used instead of the 9,9-dimethyl-fluorenyl-2-pinacolato boronic ester.

$^1H$ NMR ($CDCl_3$): δ 7.76 to 7.73 (m, 4H), 7.70 (s, 2H), 7.64 (d, J=7.92 Hz, 2H), 7.58 (s, 2H), 7.46 (d, J=6.16 Hz, 2H), 7.38 to 7.32 (m, 4H), 1.55 (s, 12H).

Comparative Synthesis Example 2

[Chemical Formula G]

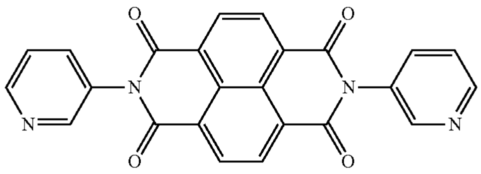

A compound represented by Chemical Formula G (1.0 g, 2.7 mmol, yield: 38.0%) is synthesized according to the same method as Synthesis Example 10 which is disclosed in a patent reference of US 2017-069690 A1.

$^1H$ NMR (DMSO-d6): δ 8.70 (d, 2H), 8.64 (s, 2H), 8.11 (t, 2H), 7.62-7.57 (m, 4H).

Comparative Synthesis Example 3

[Chemical Formula H]

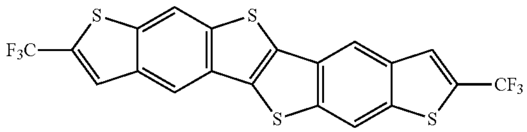

A compound represented by Chemical Formula H (4.9 g, 10.1 mmol, yield: 42.0%) is synthesized according to the same method as Preparation Example 1, which is disclosed in a patent reference of US 2008-0142792 A1, except that 2,3-dibromo-5-(trifluoromethyl)thiophene (3.1 g, 10.0 mmol) is used instead of 2,3-dibromothiophene.

$^1H$ NMR ($C_6D_5CD_3$) d 7.80 (d. 2H), 7.45 (s, 4H).

Comparative Synthesis Example 4

[Chemical Formula I]

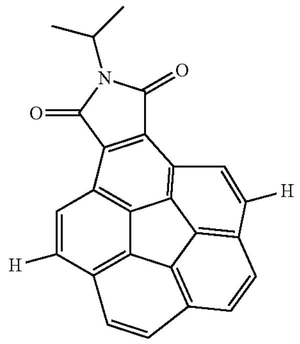

[Reaction Scheme I]

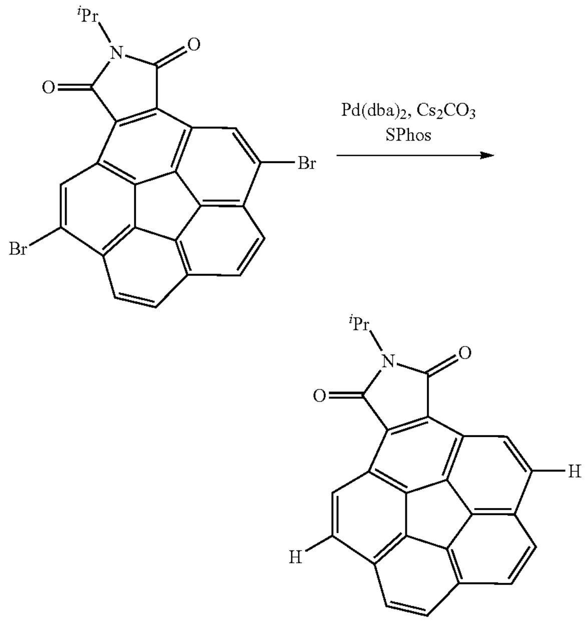

The compound (2) in Synthesis Example 1 (0.2 g, 0.3 mmol), a catalyst of $Pd(dba)_2$ (bis(dibenzylideneacetone) palladium (0), 26.4 mg, 0.1 mmol), a base of $Cs_2CO_3$ (17.8 mg, 0.8 mmol), SPhos (2-dicyclohexylphosphino-2',6'-dimethoxybiphenyl, 20.9 mg, 50.9 μmol), m-xylene (61 ml), and IPA (isopropyl alcohol, 5.0 ml) are mixed in a flask and then, stirred by using an oil bath at 80° C. for 12 hours. Subsequently, an evaporator (less than or equal to 300 mbar, greater than or equal to 40° C.) is used to remove the solvents. Then, chloroform is added to the residue and then, purified through silica gel column chromatography (an eluent: chloroform and hexane in a volume ratio of 1:1).

After evaporating the solvent from the solution, a solid therefrom is dissolved in chloroform, and a product is separated therefrom by using Recycle HPLC (Buckyprep 4.6φ×250 mm; an eluent: chloroform). The solvent is evaporated from the solution to obtain a product (0.1 g, 0.2 mmol, yield: 60.2%).

$^1$H NMR (CDCl3): δ 8.45 (d, 2H), 7.95 (d, 2H), 7.85 (d, 4H), 4.52 to 4.66 (m, 1H), 1.55 (s, 6H).

Comparative Synthesis Example 5: C60 Fullerene

[Chemical Formula J]

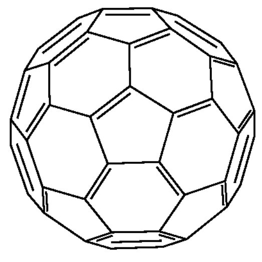

C60 fullerene (Nanom purple ST, Frontier Carbon Corp.) is used.

Example 1: Manufacture of Organic Photoelectric Device

ITO is sputtered and deposited on a glass substrate to form an about 150 nm-thick anode, and an N-type semiconductor composition including a fullerene subunit derivative represented by Chemical Formula A according to Synthesis Example 1 (an N-type semiconductor compound) and C60 fullerene represented by Chemical Formula J and a compound represented by Chemical Formula X (a P-type semiconductor compound) are codeposited thereon to form a 100 nm-thick active layer. The N-type semiconductor composition and the P-type semiconductor compound are used in a volume ratio of 1:1, and the N-type semiconductor composition includes the fullerene subunit derivative (the N-type semiconductor compound) and C60 fullerene represented by Chemical Formula J in a volume ratio of 2:3. On the active layer, a 10 nm-thick molybdenum oxide (MoOx, $0<x\leq3$) thin film is formed as a charge auxiliary layer. Subsequently, on the molybdenum oxide thin film, ITO is deposited through sputtering to form a 7 nm-thick cathode, manufacturing an organic photoelectric device.

[Chemical Formula X]

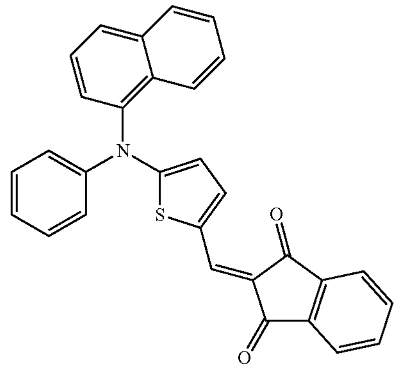

Examples 2 to 5 and Comparative Examples 4 and 5: Manufacture of Organic Photoelectric Devices Organic photoelectric devices manufactured according to the same method as Example 1 except that the fullerene subunit derivatives according to Synthesis Examples 2 to 5 and Comparative Synthesis Example 4 are respectively used instead of the fullerene subunit derivative represented by Chemical Formula A according to Synthesis Example 1.

An organic photoelectric device of Comparative Example 5 is manufactured according to the same method as Example 1 except that C60 fullerene and a P-type semiconductor compound are codeposited in a volume ration of 1:1 to form an active layer without using the fullerene derivative represented by Chemical Formula A according to Synthesis Example 1.

Examples 6 to 10 and Comparative Examples 6 and 7: Manufacture of Organic CMOS Image Sensors (OCIS)

The organic photoelectric devices according to Examples 1 to 5 and Comparative Examples 4 and 5 as an organic photoelectric device 100 for an image sensor 300 having a structure shown in FIG. 4 are respectively used to manufacture image sensors.

Evaluation 1: Deposition Temperature of Fullerene Subunit Derivative

In order to evaluate thermal stability of the fullerene subunit derivatives according to Synthesis Examples 1 to 5, deposition temperatures ($Ts_{10}$) where 10 wt % is sublimated at 10 Pa and ($Ts_{50}$) where 50 wt % is sublimated at 10 Pa are measured. In addition, the deposition temperatures of the compounds according to Comparative Synthesis Examples 1 to 5 are measured. Herein, specimens are all prepared by well drying powder purified up to high purity of greater than or equal to 99.9%, and the deposition temperatures are measured in a thermal gravimetric analysis (TGA) method. The results of the compounds according to Synthesis Examples 1 to 5 and Comparative Synthesis Examples 1 to 3 and 5 are shown in Table 1.

TABLE 1

| | Compounds | $T_s$ (−10 wt %) (° C.) | $T_s$ (−50 wt %) (° C.) |
|---|---|---|---|
| Synthesis Example 1 | Chemical Formula A | 155 | 182 |
| Synthesis Example 2 | Chemical Formula B | 235 | 260 |
| Synthesis Example 3 | Chemical Formula C | 225 | 255 |
| Synthesis Example 4 | Chemical Formula D | 260 | 290 |
| Synthesis Examples | Chemical Formula E | 198 | 228 |
| Comparative Synthesis Example 1 | Chemical Formula F | 270 | 305 |
| Comparative Synthesis Example 2 | Chemical Formula G | 266 | 301 |
| Comparative Synthesis Example 3 | Chemical Formula H (CF3-BTBTT ) | 311 | 361 |
| Comparative Synthesis Example 5 | Chemical Formula J (C60) | 445 | 500 |

* $T_s$ (−10 wt %) (° C.): a temperature where 10 wt % of a weight of a specimen is sublimated
* $T_s$ (−50 wt %) (° C.): a temperature where 50 wt % of a weight of a specimen is sublimated Referring to Table 1, the fullerene subunit derivatives according to Synthesis Example 1 to 5 exhibit a lower deposition temperature than the compounds according to Comparative Synthesis Examples 1 to 3 and 5. Accordingly, the fullerene subunit derivatives according to Synthesis Example 1 to 5 turn out to be compounds capable of being deposited through sublimation.

Evaluation 2: Energy Level of Fullerene Subunit Derivative

The fullerene subunit derivatives according to Synthesis Examples 1 to 5 are deposited to form thin films, and each thin film is measured with respect to HOMO and LUMO energy levels by using a B3LYP/6-31G(d) level theory described in [M. J. Frisch, et al., Gaussian 09, Revision D.01; Gaussian, Inc.: Wallingford, Conn. 2009] in a method of Gaussian 09 program. The results of Synthesis Examples 1 to 5 and Comparative Synthesis Example 5 are shown in Table 2. For reference, the HOMO and LUMO energy levels of the compounds represented by Chemical Formulae K and L as a P-type semiconductor compound are provided.

TABLE 2

| Compounds | HOMO (eV) | LUMO (eV) |
|---|---|---|
| Chemical Formula A (Synthesis Example 1) | −6.3 | −2.9 |
| Chemical Formula B (Synthesis Example 2) | −6.3 | −3.0 |
| Chemical Formula C (Synthesis Example 3) | −6.4 | −3.0 |
| Chemical Formula D (Synthesis Example 4) | −6.5 | −3.1 |
| Chemical Formula E (Synthesis Example 5) | −6.4 | −3.1 |
| Chemical Formula J (C60, Comparative Synthesis Example 5) | −6.4 | −3.7 |
| Chemical Formula K | −5.4 | −2.5 |
| Chemical Formula L | −5.6 | −2.6 |

Chemical Formulae K and L shown in Table 2 have the following structures.

[Chemical Formula K]

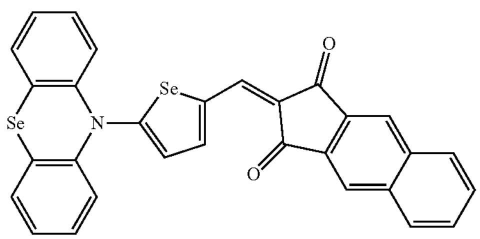

[Chemical Formula L]

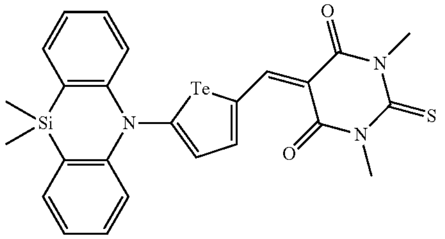

Referring to Table 2, when the compounds according to Synthesis Examples 1 to 5 are measured with B3LYP/6-31 G(d) with reference to [M. J. Frisch, et al., Gaussian 09, Revision D.01; Gaussian, Inc.: Wallingford, Conn. 2009], HOMO levels thereof are equal to that of C60, and LUMO levels are not high enough to be usable as an N-type semiconductor. Compared with the HOMO and LUMO energy levels of the compounds of Chemical Formulae K and L as a P-type semiconductor compound, the compounds of Synthesis Examples 1 to 5 may be appropriately used as an N-type semiconductor compound.

Evaluation 3: Distance Between N-Type Semiconductor and P-Type Semiconductor

A Nanomatch software is used to evaluate morphology of an active layer formed on a substrate by codepositing N-type and P-type semiconductors. Results of calculating average distances between the N-type and the P-type semiconductor (a compound represented by Chemical Formula X) in the active layer are shown in Table 3. Virtually-formed blend morphology obtained by using the software is used to calculate the average distances, and the results are shown in Table 3.

TABLE 3

| N-type semiconductor | Average distance (Å) |
|---|---|
| Chemical Formula A (Synthesis Example 1) | 4.6 |
| Chemical Formula B (Synthesis Example 2) | 2.9 |
| Chemical Formula C (Synthesis Example 3) | 3.3 |
| Chemical Formula D (Synthesis Example 4) | 4.0 |
| Chemical Formula E (Synthesis Example 5) | 2.3 |
| Chemical Formula M | 3.6 |
| Chemical Formula N | 4.6 |
| Chemical Formula O | 4.7 |

TABLE 3-continued

| N-type semiconductor | Average distance (Å) |
|---|---|
| Chemical Formula P | 4.1 |
| Chemical Formula Q | 4.3 |
| Chemical Formula I (Comparative Synthesis Example 4) | 6.9 |

The structures of Chemical Formulae M to Q shown in Table 3 are as follows.

[Chemical Formula M]

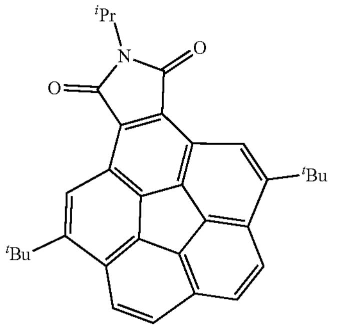

[Chemical Formula N]

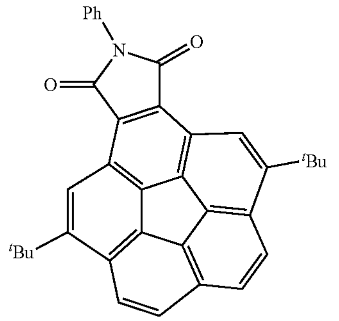

[Chemical Formula O]

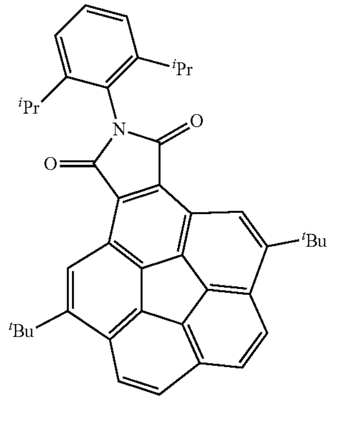

-continued

[Chemical Formula P]

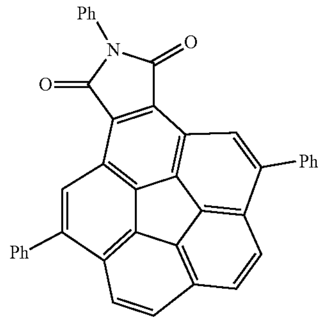

[Chemical Formula Q]

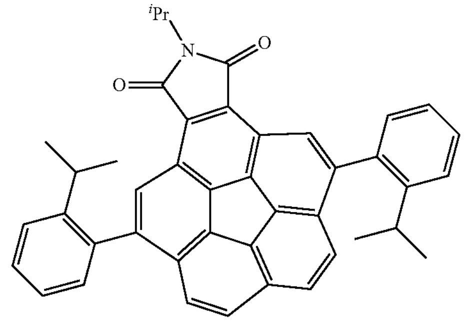

Referring to Table 3, the compounds represented by Chemical Formulae A to E and M to Q include a bulky substituent X and an additional bulky substituent at the side and thus have shorter distances with the P-type semiconductor than the compound represented by Chemical Formula I having no bulky substituent. The reason is that since crystallization of each compound represented by Chemical Formulae A to E and M to Q (the N-type semiconductor) is further reduced or suppressed, compared with that of the compound represented by Chemical Formula I, the compounds are respectively well mixed with the P-type semiconductor and form the active layers. Accordingly, crystallinity of the compounds is not only sufficiently low, but also the compounds represented by Chemical Formulae A to E and M to Q are well mixed with the P-type semiconductor.

Evaluation 4: External Quantum Efficiency Characteristics of Device

External quantum efficiency (EQE) of the organic photoelectric devices according to Examples 1 to 5 and Comparative Examples 4 and 5 is measured. The external quantum efficiency is measured by using an IPCE measurement system (McScience Inc, Korea). First, an Si photodiode (Hamamatsu Photonics K.K., Japan) is used to calibrate the system, and the organic photoelectric devices according to Examples 1 to 5 and Comparative Examples 4 and 5 are respectively mounted thereon and measured with respect to the external quantum efficiency in a wavelength range of about 350 nm to 750 nm. The results of Examples 1 to 5 and Comparative Examples 4 and 5 are shown in Table 4.

TABLE 4

| | Active layer compound | $EQE_{max}$ (3 V) room temperature Blue/Green/Red [%/%/%/] | $EQE_{max}$ (3 V) 160° C. annealing (3 h) Blue/Green/Red [%/%/%/] |
|---|---|---|---|
| Example 1 | P-type compound, Chemical Formula A, Chemical Formula J | 14/58/15 | 14/60/15 |
| Example 2 | P-type compound, Chemical Formula B, Chemical Formula J | 10/48/12 | 11/49/12 |
| Example 3 | P-type compound, Chemical Formula C, Chemical Formula J | 10/47/12 | 11/58/12 |
| Example 4 | P-type compound, Chemical Formula D, Chemical Formula J | 12/54/14 | 12/55/13 |
| Example 5 | P-type compound, Chemical Formula E, Chemical Formula J | 10/48/11 | 10/49/11 |
| Comparative Example 4 | P-type compound, Chemical Formula I, Chemical Formula J | 11/53/13 | 7/30/8 |
| Comparative Example 5 | P-type compound, Chemical Formula J | 21/63/23 | 21/66/24 |

Referring to Table 4, absorption of the organic photoelectric devices according to Examples 1 to 5 in a blue region is decreased by 30% to 50% or more, compared with that of Comparative Example 5. Absorption of C60 in the blue region (450 nm) is known due to aggregation of C60 (Journal of Molecular Structure 526 (2000) 25 to 29). In other words, the absorption decrease of the organic photoelectric devices of Examples 1 to 5 in the blue region (450 nm) means that the C60 aggregation decreases or disappears. Accordingly, abnormal light absorption properties of the organic photoelectric devices of Examples 1 to 5 in the blue region do not occur.

On the other hand, EQE of Comparative Example 4 in the blue region at room temperature is decreased before annealing like Examples 1 to 5, but EQE performance thereof after the annealing is deteriorated in the entire visible light regions (Blue/Green/Red).

Although not bound by any theory, the reason that EQE performance of the organic photoelectric devices of Examples 1 to 5 is not deteriorated after the annealing is that the fullerene subunit derivative contains three bulky substituents in corannulene and thus is not crystallized at a high temperature. On the other hand, Comparative Example 4 including one bulky substituent X in the corannulene is crystallized due to the annealing. Accordingly, the fullerene subunit derivative having one bulky substituent exhibits low thermal stability.

Evaluation 5: Absorption Coefficient in Blue Region

The organic photoelectric devices of Examples 1 to 5 and Comparative Examples 4 and 5 are measured with respect to an absorption coefficient in the blue region (450 nm). The results of Examples 1 to 5 and Comparative Example 5 are shown in Table 5.

TABLE 5

| | Active layer compound | Abs. Coeff. (450 nm) [$10^4$ $cm^{-1}$] |
|---|---|---|
| Example 1 | P-type compound, Chemical Formula A, Chemical Formula J | 1.1 |
| Example 2 | P-type compound, Chemical Formula B, Chemical Formula J | 1.1 |
| Example 3 | P-type compound, Chemical Formula C, Chemical Formula J | 1.0 |
| Example 4 | P-type compound, Chemical Formula D, Chemical Formula J | 1.1 |
| Example 5 | P-type compound, Chemical Formula E, Chemical Formula J | 1.0 |
| Comparative Example 5 | P-type compound, Chemical Formula J | 1.5 |

Referring to Table 5, absorption of the organic photoelectric devices of Example 1 to 5 in the blue region is 25% or more decreased compared with that of Comparative Example 5.

Evaluation 6: Mobility

Mobility of the organic photoelectric devices of Examples 1 to 5 and Comparative Examples 4 and 5 is measured. The mobility is measured in a Space-charge-limited current (SCLC) method disclosed in an article of Solar Energy Materials & Solar Cells 141 (2015) 87 to 92. The results of Examples 1 to 5 and Comparative Example 5 are shown in Table 6.

TABLE 6

| | Active layer compound | Electron mobility [$cm^2/Vs$] |
|---|---|---|
| Example 1 | P-type compound, Chemical Formula A, Chemical Formula J | 8.6E−6 |
| Example 2 | P-type compound, Chemical Formula B, Chemical Formula J | 9.6E−6 |
| Example 3 | P-type compound, Chemical Formula C, Chemical Formula J | 6.6E−6 |
| Example 4 | P-type compound, Chemical Formula D, Chemical Formula J | 8.0E−6 |
| Example 5 | P-type compound, Chemical Formula E, Chemical Formula J | 8.4E−6 |
| Comparative Example 5 | P-type compound, Chemical Formula J | 4.0E−6 |

Referring to Table 6, the mobility of the organic photoelectric devices of Examples 1 to 5 is 1.65 times or more as high as that of the organic photoelectric device of Comparative Example 5.

Since partial aggregation of C60 which is regarded to be present in a bulk hetero junction (BHJ) of the active layer is reduced or suppressed due to the fullerene subunit derivative, the mobility may be improved by suppressing a charge loss at aggregation points. In addition, the fullerene subunit derivative has N-type characteristics and thus may play a role of transporting charges and improve the mobility.

Evaluation 7: YSNR10

The image sensors of Examples 6 to 10 and Comparative Examples 6 and 7 respectively including the organic photoelectric devices of Examples 1 to 5 and Comparative Examples 4 and 5 are evaluated with respect to YSNR10.

YSNR10 is measured by taking a photo of an 18% gray patch of the Macbeth chart under a light source of D-65.

Herein, lens has an F value of 2.8 and transmittance of 80%, and interference-type lens are used for an infrared ray cut filter. A pixel size of the image sensors is 1.4 μm, and a frame rate of the image sensors is 15 fps.

Herein, YSNR10 is used to evaluate sensitivity of the image sensors and measured in a Juha Alakarhu's "Image Sensors and Image Quality in Mobile Phones" method disclosed in an outline of International Image Sensor Workshop (Ogunquit Me., USA) in 2007, but minimum illumination where a ratio of signal and noise becomes 10 is expressed as lux. The results of the image sensors including the organic photoelectric devices of Example 1 and Comparative Example 5 are shown in Table 7.

TABLE 7

| | Active layer compound | YSNR10 [lux] |
|---|---|---|
| Example 1 | P-type compound, Chemical Formula A, Chemical Formula J | 85 |
| Comparative Example 5 | P-type compound, Chemical Formula J | 96 |

Referring to Table 7, the image sensor including the organic photoelectric device of Example 1 exhibits 10% improved YSNR10 compared with the image sensor including the organic photoelectric device of Comparative Example 5.

While this disclosure has been described in connection with what is presently considered to be practical example embodiments, it is to be understood that inventive concepts are not limited to the disclosed embodiments. On the contrary, inventive concepts are intended to cover various modifications and equivalent arrangements included within the spirit and scope of the appended claims.

What is claimed is:

1. An organic photoelectric device comprising:

a first electrode and a second electrode facing each other, and an organic layer between the first electrode and the second electrode, wherein the organic layer includes an N-type semiconductor composition, the N-type semiconductor composition including, fullerene or a fullerene derivative; and a fullerene subunit derivative represented by Chemical Formula 1:

[Chemical Formula 1]

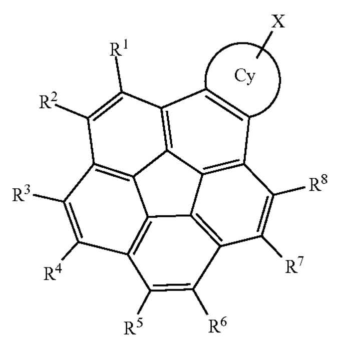

wherein, in Chemical Formula 1,

Cy is a cyclic hydrocarbon group selected from a C3 to C20 alicyclic hydrocarbon group and a C6 to C20 aromatic hydrocarbon group, or a fused cyclic group of two or more cyclic hydrocarbon groups, X is at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, and $R^1$ to $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided at least one of $R^1$ to $R^8$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

2. The organic photoelectric device of claim 1, wherein in Chemical Formula 1, at least one of $R^1$ to $R^3$ and at least one of $R^6$ to $R^8$ are the same or different, and at least one of $R^1$ to $R^3$ and at least one of $R^6$ to $R^8$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

3. The organic photoelectric device of claim 2, wherein in Chemical Formula 1, at least one bulky substituent of $R^1$ to $R^3$ and at least one bulky substituent of $R^6$ to $R^8$ are present symmetrically with respect to an axis through Cy.

4. The organic photoelectric device of claim 1, wherein in Chemical Formula 1, at least one of $R^1$ and $R^2$ and at least one of $R^7$ and $R^8$ are the same or different, and are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof.

5. The organic photoelectric device of claim 1, wherein In Chemical Formula 1, $R^2$ and $R^7$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and $R^1$, $R^3$, $R^4$, $R^5$, $R^6$, and $R^8$ are hydrogen, deuterium, a halogen, a cyano group, a C1 to C20 linear alkyl group, or a combination thereof.

6. The organic photoelectric device of claim 1, wherein in Chemical Formula 1, two adjacent substituents of $R^1$ to $R^3$ and two adjacent substituents of $R^6$ to $R^8$ are linked to each other to provide a C3 to C20 alicyclic hydrocarbon group.

7. The organic photoelectric device of claim 6, wherein in Chemical Formula 1, $R^2$ and $R^3$ are linked to each other to provide a C3 to C20 alicyclic hydrocarbon group, and $R^6$ and $R^7$ are linked to each other to provide a C3 to C20 alicyclic hydrocarbon group.

8. The organic photoelectric device of claim 7, wherein the fullerene subunit derivative represented by Chemical Formula 1 is a compound represented by Chemical Formula 1A:

[Chemical Formula 1A]

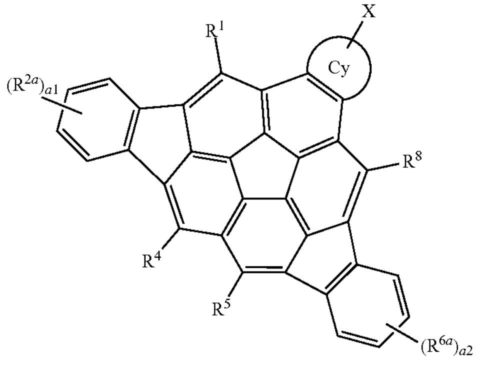

wherein, in Chemical Formula 1A,

Cy is a cyclic hydrocarbon group selected from a C3 to C20 alicyclic hydrocarbon group and a C6 to C20 aromatic hydrocarbon group, or a fused cyclic group of two or more cyclic hydrocarbon groups, X is at least one bulky substituent selected from a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, and a substituted or unsubstituted C2 to C30 heteroaryl group, $R^1$, $R^{2a}$, $R^4$, $R^5$, $R^{6a}$, and $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, and a1 and a2 are independently integers of 1 to 4.

9. The organic photoelectric device of claim 1, wherein the cyclic hydrocarbon group in Cy is a heterocyclic group including at least one functional group selected from —N═, —NR—, —O—, —S—, —Se—, —Te—, —C(═O)—, —C(═S)—, —C(═Se)—, —C(═Te)—, —C(═C$(CN)_2$)—, and —C(═NR)— wherein R is a C1 to C10 alkyl group.

10. The organic photoelectric device of claim 1, wherein in Chemical Formula 1, Cy is pyrrole, furan, pyrroline, pyrrolidinedione, cyclopentanediene, cyclopentanedione, pyrrolo imidazole, pyrrolo imidazole including ketone (C═O) group in the ring, pyridine, pyrimidine, indole, phthalimide, benzimidazole, benzothiazole, or a fused ring of the foregoing rings and benzene rings.

11. The organic photoelectric device of claim 1, wherein in Chemical Formula 1, Cy is selected from moieties represented by Chemical Formulae 2A to 2C:

[Chemical Formula 2A]

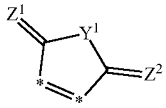

wherein, in Chemical Formula 2A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $Z^1$ and $Z^2$ are O, S, Se, Te, $C(CN)_2$, or $NR^d$, wherein $R^d$ is a C1 to C10 alkyl group or is linked to $Y^1$ of Chemical Formula 2A to provides a fused ring, and

*=* is a linking portion with Chemical Formula 1,

[Chemical Formula 2B]

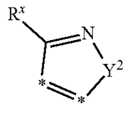

wherein, in Chemical Formula 2B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1,

[Chemical Formula 2C]

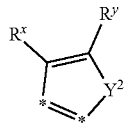

wherein, in Chemical Formula 2C, $Y^2$ is $CR^aR^b$, $NR^c$, O, S, Se, or Te, wherein $R^c$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

12. The organic photoelectric device of claim 1, wherein in Chemical Formula 1, Cy is selected from moieties represented by Chemical Formulae 3A to 3D:

[Chemical Formula 3A]

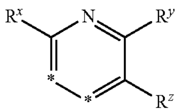

wherein, in Chemical Formula 3A, $R^x$, $R^y$, and $R^z$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$, $R^y$, and $R^z$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1,

[Chemical Formula 3B]

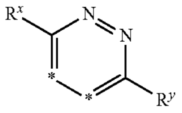

wherein, in Chemical Formula 3B, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1,

[Chemical Formula 3C]

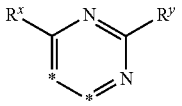

wherein, in Chemical Formula 3C, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1,

[Chemical Formula 3D]

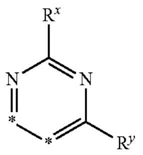

wherein, in Chemical Formula 3D, $R^x$ and $R^y$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, and

*=* is a linking portion with Chemical Formula 1.

13. The organic photoelectric device of claim 1, wherein in Chemical Formula 1, Cy is selected from moieties represented by Chemical Formulae 4A to 4C:

[Chemical Formula 4A]

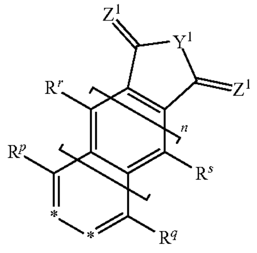

wherein, in Chemical Formula 4A, $Y^1$ is $CR^aR^b$ or $NR^c$, $R^a$ and $R^b$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided that at least one of $R^a$ and $R^b$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^c$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, $R^p$, $R^q$, $R^r$, and $R^s$ are independently hydrogen, deuterium, or a C1 to C10 alkyl group, n is an integer of 0 to 2, $Z^1$ and $Z^2$ are O, S, Se, Te, $C(CN)_2$, or $NR^d$, wherein $R^d$ is a C1 to C10 alkyl group or is linked to $Y^1$ of Chemical Formula 4A to provides a fused ring, and

*=* is a linking portion with Chemical Formula 1,

[Chemical Formula 4B]

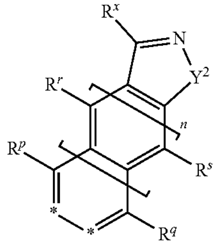

wherein, in Chemical Formula 4B, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ is hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, and $R^x$ and at least one of $R^c$ and $R^x$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, $R^x$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, n is an integer of 0 to 2, $R^p$, $R^q$, $R^r$, and $R^s$ are independently hydrogen, deuterium, or a C1 to C10 alkyl group, and

*=* is a linking portion with Chemical Formula 1,

[Chemical Formula 4C]

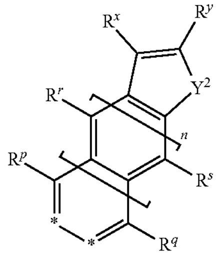

wherein, in Chemical Formula 4C, $Y^2$ is $CR^aR^b$, $NR^c$, O, S, Se, or Te, wherein $R^a$, $R^b$, and $R^c$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, $R^x$ and $R^y$ are hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, when $Y^2$ is $CR^aR^b$ or $NR^c$, at least one of $R^a$, $R^b$, $R^x$, and $R^y$ and at least one of $R^c$, $R^x$, and $R^y$ are a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, when $Y^2$ is O, S, Se, or Te, at least one of $R^x$ and $R^y$ is a bulky substituent selected from a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, and a combination thereof, n is an integer of 0 to 2, $R^p$, $R^q$, $R^r$, and $R^s$ are independently hydrogen, deuterium, or a C1 to C10 alkyl group, and

*=* is a linking portion with Chemical Formula 1.

14. The organic photoelectric device of claim 1, wherein in Chemical Formula 1, at least one of $R^1$ to $R^8$ independently are a group represented by Chemical Formula 5A:

[Chemical Formula 5A]

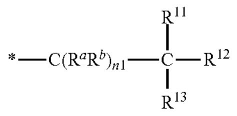

wherein, in Chemical Formula 5A, $R^a$ and $R^b$ are hydrogen, a halogen, a cyano group, or a C1 to C6 alkyl group, n1 is an integer of 0 to 10, and $R^{11}$ to $R^{13}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

15. The organic photoelectric device of claim 1, wherein in Chemical Formula 1, at least one of $R^1$ to $R^8$ independently are a group represented by Chemical Formula 5B:

[Chemical Formula 5B]

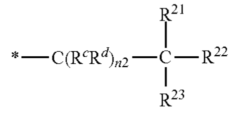

wherein, in Chemical Formula 5B, $R^c$ and $R^d$ are hydrogen, a halogen, a cyano group, a C1 to C6 alkyl group, a C1 to C6 alkoxy group, a C2 to C10 ether group, or a C2 to C10 ester group, n2 is an integer of 2 to 10, —$C(R^cR^d)$— is replaced by at least one functional group selected from —O—, —S—, —S(═O)—, —S(═O)$_2$—, —C(═O)—, —C(═O)O—, —OC(═O)—, and a combination thereof, and $R^{21}$ to $R^{23}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{21}$ to $R^{23}$ are a C1 to C10 alkyl group, a C1 to C10 alkoxy group, a C2 to C10 alkenyl group, or a C2 to C10 alkynyl group.

16. The organic photoelectric device of claim 1, wherein in Chemical Formula 1, at least one of $R^1$ to $R^8$ independently are a group represented by Chemical Formula 5C:

[Chemical Formula 5C]

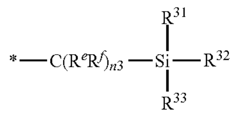

wherein, in Chemical Formula 5C, $R^e$ and $R^f$ are hydrogen, a halogen, a cyano group, or a C1 to C6 alkyl group, n3 is an integer of 0 to 10, and $R^{31}$ to $R^{33}$ are hydrogen, a halogen, a cyano group, a C1 to C10 alkyl group, a C1 to C10 alkoxy group, a C2 to C10 alkenyl group, a C2 to C10 alkynyl group, or a C1 to C10 alkylsilyl group, provided that at least two of $R^{31}$ to $R^{33}$ are a C1 to C10 alkyl group, a C1 to C10 alkoxy group, a C2 to C10 alkenyl group, or a C2 to C10 alkynyl group.

17. The organic photoelectric device of claim 1, wherein in Chemical Formula 1, at least one of $R^1$ to $R^8$ independently are an isopropyl group, a 1-methylpropyl group, an isobutyl group, a 1-methylbutyl group, a 1-ethylbutyl group, a 1-propylbutyl group, an isopentyl group, a 1-methylpentyl group, a 1-ethylpentyl group, a 1-propylpentyl group, a 2-methylpentyl group, a 2-ethylpentyl group, a 2-propylpentyl group, a 3-methylpentyl group, a 3-ethylpentyl group, a 3-propylpentyl group, an isohexyl group, a 1-methylhexyl group, a 1-ethylhexyl group, a 1-propylhexyl group, a 2-methylhexyl group, a 2-ethylhexyl group, a 2-propylhexyl group, a 3-methylhexyl group, a 3-ethylhexyl group, a 3-propylhexyl group, an isoheptyl group, a 1-methylheptyl group, a 1-ethylheptyl group, a 1-propylheptyl group, a 2-methylheptyl group, a 2-ethylheptyl group, a 2-propylheptyl group, a 3-methylheptyl group, a 3-ethylheptyl group, a 3-propylheptyl group, an isooctyl group, a 1-methyloctyl group, a 1-ethyloctyl group, a 1-propyloctyl group, a 2-methyloctyl group, a 2-ethyloctyl group, a 2-propyloctyl group, a 3-methyloctyl group, a 3-ethyloctyl group, a 3-propyloctyl group, a 1-methylnonyl group, a 1,1-dimethylnonyl group, a t-butyl group, a t-pentyl group, a t-hexyl group, a neopentyl group, or a neohexyl group.

18. An organic photoelectric device comprising:

a first electrode and a second electrode facing each other, and an organic layer between the first electrode and the second electrode, wherein the organic layer includes an N-type semiconductor composition, the N-type semiconductor composition including, fullerene or a fullerene derivative; and a fullerene subunit derivative represented by Chemical Formula 1:

[Chemical Formula 1]

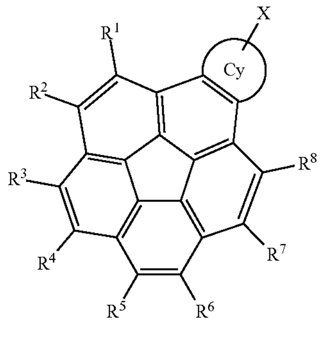

wherein, in Chemical Formula 1,

Cy includes a C3 to C20 alicyclic hydrocarbon group, a C6 to C20 aromatic hydrocarbon group, or a fused cyclic group of two or more cyclic hydrocarbon groups, X includes a substituted or unsubstituted C3 to C30 branched alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and $R^1$ to $R^8$ are independently hydrogen, deuterium, a halogen, a cyano group, a substituted or unsubstituted C1 to C20 linear or branched alkyl group, a substituted or unsubstituted C1 to C20 linear or branched alkoxy group, a substituted or unsubstituted C3 to C20 linear or branched alkylsilyl group, a substituted or unsubstituted C2 to C20 linear or branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof, provided at least one of $R^1$ to $R^8$ includes a substituted or unsubstituted C3 to C20 branched alkyl group, a substituted or unsubstituted C3 to C20 branched alkoxy group, a substituted or unsubstituted C3 to C20 branched alkylsilyl group, a substituted or unsubstituted C3 to C20 branched heteroalkyl group, a substituted or unsubstituted C6 to C30 aryl group, a substituted or unsubstituted C2 to C30 heteroaryl group, a substituted or unsubstituted C3 to C30 cycloalkyl group, a substituted or unsubstituted C3 to C30 heterocycloalkyl group, or a combination thereof.

19. The organic photoelectric device of claim 1, wherein an absorption coefficient at a wavelength of about 450 nm of a thin film including the N-type semiconductor composition is smaller than an absorption coefficient at a wavelength of about 450 nm of a thin film including unsubstituted C60 fullerene.

20. The organic photoelectric device of claim 1, wherein the organic layer includes an active layer, the active layer includes a P-type semiconductor and an N-type semiconductor forming a pn junction, and the N-type semiconductor includes the N-type semiconductor composition.

21. The organic photoelectric device of claim 20, wherein the fullerene subunit derivative has an average distance of less than or equal to about 6 Å from a P-type semiconductor.

22. An image sensor comprising:

the organic photoelectric device of claim 1.

23. An electronic device comprising:

the organic photoelectric device of claim 1.

24. An image sensor comprising:

the organic photoelectric device of claim 18.

* * * * *